United States Patent
Cozean et al.

(10) Patent No.: US 8,480,797 B2
(45) Date of Patent: Jul. 9, 2013

(54) ACTIVATED CARBON SYSTEMS FOR FACILITATING USE OF DIMETHYL SULFOXIDE (DMSO) BY REMOVAL OF SAME, RELATED COMPOUNDS, OR ASSOCIATED ODORS

(75) Inventors: Jesse Cozean, Lake Forest, CA (US); Colette Cozean, Lake Forest, CA (US); Efrain Gonzales, Mission Viejo, CA (US); Stanley W. Jacob, Portland, OR (US)

(73) Assignee: Abela Pharmaceuticals, Inc., Lake Forest, CA (US)

( * ) Notice: Subject to any disclaimer, the term of this patent is extended or adjusted under 35 U.S.C. 154(b) by 191 days.

(21) Appl. No.: 13/099,120

(22) Filed: May 2, 2011

(65) Prior Publication Data
US 2011/0203585 A1 Aug. 25, 2011

Related U.S. Application Data

(63) Continuation-in-part of application No. PCT/US2009/063006, filed on Nov. 2, 2009, and a continuation-in-part of application No. 12/066,485, filed as application No. PCT/US2006/035321 on Sep. 11, 2006, now Pat. No. 7,955,418.

(60) Provisional application No. 61/110,875, filed on Nov. 3, 2008, provisional application No. 60/716,271, filed on Sep. 12, 2005, provisional application No. 60/716,336, filed on Sep. 12, 2005, provisional application No. 60/716,278, filed on Sep. 12, 2005, provisional application No. 60/716,369, filed on Sep. 12, 2005.

(51) Int. Cl.
*A61M 16/00* (2006.01)
*A61L 9/014* (2006.01)

(52) U.S. Cl.
USPC ........................................ 96/134; 128/205.27

(58) Field of Classification Search
USPC .. 95/135, 137, 141; 96/134, 154; 128/200.24, 128/204.15, 205.12, 205.27, 206.21, 207.14; 423/244.01; 55/DIG. 33, DIG. 35
See application file for complete search history.

(56) References Cited

U.S. PATENT DOCUMENTS 3,334,012 A 8/1967 Herschler
3,361,555 A 1/1968 Herschler
(Continued)

FOREIGN PATENT DOCUMENTS

CA 2617934 2/2007
EP 0827744 3/1998
(Continued)

OTHER PUBLICATIONS

Aleksevich Ial, Piletskaia IG, Nikonorova VP. *Increase in the sensitivity of the microflora of pathological gingival pockets to streptomycin under the influence of dimexide and trypsin.* Mikrobiol Zh. Nov.-Dec. 1973; 35(6):766-9.

(Continued)

*Primary Examiner* — Frank Lawrence, Jr.
(74) *Attorney, Agent, or Firm* — Knobbe Martens Olson & Bear, LLP

(57) ABSTRACT

Several embodiments of the invention relate to systems and methods for removing compositions comprising dimethyl sulfoxide (DMSO) or related compounds, or odors associated with same. In several embodiments, the systems include activated carbon filters, adsorbents, odor adsorbing fabrics, masks, clean air members and clean air supply assemblies. Methods for reducing the concentration of a DMSO metabolite, or the odors associated with said DMSO metabolite are provided in some embodiments. In some embodiments the systems and methods facilitating the treatment of traumatic brain injury, ischemic stroke, atherosclerosis, spinal cord trauma, and neurodegenerative illnesses with compositions comprising DMSO.

16 Claims, 12 Drawing Sheets

U.S. PATENT DOCUMENTS

| | | |
|---|---|---|
| 3,393,080 A | 7/1968 | Erdi et al. |
| 3,419,619 A | 12/1968 | Soder et al. |
| 3,482,572 A | 12/1969 | Grosclaude et al. |
| 3,527,863 A | 9/1970 | Weichselbaum |
| 3,549,770 A | 12/1970 | Herschler et al. |
| 3,549,771 A | 12/1970 | Herschler |
| 3,551,554 A | 12/1970 | Herschler |
| 3,558,434 A | 1/1971 | Herschler |
| 3,573,214 A | 3/1971 | Kollonitsch |
| 3,592,936 A | 7/1971 | Marcus et al. |
| 3,654,165 A | 4/1972 | Bryant et al. |
| 3,675,654 A | 7/1972 | Baker et al. |
| 3,690,808 A | 9/1972 | St. Pierre |
| 3,711,606 A | 1/1973 | Herschler |
| 3,740,420 A | 6/1973 | Herschler et al. |
| 3,773,838 A | 11/1973 | Andruski et al. |
| 3,790,682 A | 2/1974 | Herschler et al. |
| 3,823,676 A | 7/1974 | Cook et al. |
| 3,852,408 A | 12/1974 | Ewan et al. |
| 3,861,894 A | 1/1975 | Marsh |
| 3,881,003 A | 4/1975 | Rehm |
| 3,948,617 A | 4/1976 | Withorn |
| 3,972,962 A | 8/1976 | Williams et al. |
| 3,976,747 A | 8/1976 | Shale et al. |
| 3,988,129 A | 10/1976 | Fornoff et al. |
| 3,996,295 A | 12/1976 | Goeb |
| 4,015,025 A | 3/1977 | Szczesniak |
| 4,112,946 A | 9/1978 | Herschler |
| 4,125,589 A | 11/1978 | deVries |
| 4,129,122 A | 12/1978 | Dout et al. |
| 4,169,550 A | 10/1979 | Williams |
| 4,177,267 A | 12/1979 | Herschler |
| 4,194,628 A | 3/1980 | Campos |
| 4,202,676 A | 5/1980 | Pelosi, Jr. et al. |
| 4,212,392 A | 7/1980 | McKenzie |
| 4,225,381 A | 9/1980 | Ishikawa et al. |
| 4,252,054 A | 2/1981 | Bakels |
| 4,256,728 A | 3/1981 | Nishino et al. |
| 4,277,450 A | 7/1981 | Dilworth |
| 4,296,104 A | 10/1981 | Herschler |
| 4,296,130 A | 10/1981 | Herschler |
| 4,307,067 A | 12/1981 | Tagawa et al. |
| 4,309,393 A | 1/1982 | Nguyen |
| 4,316,795 A | 2/1982 | Mooi |
| 4,333,922 A | 6/1982 | Herschler |
| 4,335,148 A | 6/1982 | Vidal et al. |
| 4,341,675 A | 7/1982 | Nakamura |
| 4,350,245 A | 9/1982 | Elstner |
| 4,357,288 A | 11/1982 | Oas et al. |
| 4,369,190 A | 1/1983 | Schulte |
| 4,372,915 A | 2/1983 | Neti et al. |
| 4,413,109 A | 11/1983 | Haas |
| 4,424,330 A | 1/1984 | Raviola |
| 4,469,702 A | 9/1984 | Schulte |
| 4,477,469 A | 10/1984 | Herschler |
| 4,491,563 A | 1/1985 | Reusser et al. |
| 4,493,930 A | 1/1985 | Klayman et al. |
| 4,497,824 A | 2/1985 | Schulte |
| 4,505,708 A | 3/1985 | Gajewski et al. |
| 4,510,292 A | 4/1985 | Chiba et al. |
| 4,512,245 A | 4/1985 | Goldman |
| 4,514,421 A | 4/1985 | Herschler |
| 4,545,414 A | 10/1985 | Baum |
| 4,550,010 A | 10/1985 | Chelu |
| 4,559,329 A | 12/1985 | Herschler |
| 4,568,547 A | 2/1986 | Herschler |
| 4,575,515 A | 3/1986 | Sandborn |
| 4,591,497 A | 5/1986 | Naito et al. |
| 4,595,102 A | 6/1986 | Cianci et al. |
| 4,600,002 A | 7/1986 | Maryyanek et al. |
| 4,616,039 A | 10/1986 | Herschler |
| 4,616,064 A | 10/1986 | Zukosky et al. |
| 4,622,221 A | 11/1986 | Schleppnik |
| 4,626,530 A | 12/1986 | Schulte |
| 4,634,588 A | 1/1987 | Moroe |
| 4,642,177 A | 2/1987 | Mester et al. |
| 4,652,557 A | 3/1987 | Sandborn |
| 4,655,148 A | 4/1987 | Winship |
| 4,656,094 A | 4/1987 | Kojima et al. |
| 4,686,204 A | 8/1987 | Mester et al. |
| 4,710,353 A | 12/1987 | Tanaka et al. |
| 4,719,105 A | 1/1988 | Schleppnik |
| 4,721,813 A | 1/1988 | Mark et al. |
| 4,725,290 A | 2/1988 | Ohlmeyer et al. |
| 4,728,712 A | 3/1988 | Singh et al. |
| 4,729,835 A | 3/1988 | McNeillie et al. |
| 4,737,173 A | 4/1988 | Kudirka et al. |
| 4,747,845 A | 5/1988 | Korol |
| 4,751,241 A | 6/1988 | Motoyama et al. |
| 4,778,697 A | 10/1988 | Genske et al. |
| 4,784,909 A | 11/1988 | Emi et al. |
| 4,796,790 A | 1/1989 | Hamilton |
| 4,797,274 A | 1/1989 | Miki et al. |
| 4,803,047 A | 2/1989 | Pluim, Jr. |
| 4,830,718 A | 5/1989 | Stauffer |
| 4,834,721 A | 5/1989 | Onohara et al. |
| 4,850,268 A | 7/1989 | Saito et al. |
| 4,863,687 A | 9/1989 | Stevens et al. |
| 4,863,748 A | 9/1989 | Herschler |
| 4,887,751 A | 12/1989 | Lehman |
| 4,902,489 A | 2/1990 | Watanabe |
| 4,902,558 A | 2/1990 | Henriksen |
| 4,904,520 A | 2/1990 | Dumas et al. |
| 4,910,803 A | 3/1990 | Cukier |
| 4,911,691 A | 3/1990 | Aniuk et al. |
| 4,914,135 A | 4/1990 | Herschler |
| 4,916,767 A | 4/1990 | Uetake et al. |
| 4,919,925 A | 4/1990 | Ueda et al. |
| 4,931,276 A | 6/1990 | Franco et al. |
| 4,937,115 A | 6/1990 | Leatherman |
| 4,940,405 A | 7/1990 | Kelly |
| 4,940,658 A | 7/1990 | Allen et al. |
| 4,941,991 A | 7/1990 | Rajamannan |
| 4,946,720 A | 8/1990 | Oishi et al. |
| 4,948,643 A | 8/1990 | Mueller |
| 4,948,787 A | 8/1990 | Chen et al. |
| 4,956,183 A | 9/1990 | Miki et al. |
| 4,973,605 A | 11/1990 | Herschler |
| 4,978,687 A | 12/1990 | Pascuchi |
| 4,980,045 A | 12/1990 | Krishna et al. |
| 4,988,505 A | 1/1991 | Watanabe et al. |
| 4,990,311 A | 2/1991 | Hirai et al. |
| 4,994,245 A | 2/1991 | Murray et al. |
| 5,001,794 A | 3/1991 | Uetake et al. |
| 5,006,510 A | 4/1991 | Ellis |
| 5,007,999 A | 4/1991 | Chin |
| 5,032,613 A | 7/1991 | Watson |
| 5,041,273 A | 8/1991 | Rock |
| 5,049,159 A | 9/1991 | Yamaji et al. |
| 5,049,163 A | 9/1991 | Huang et al. |
| 5,055,279 A | 10/1991 | Hirt et al. |
| 5,059,477 A | 10/1991 | Henriksen |
| 5,070,597 A | 12/1991 | Holt et al. |
| 5,071,622 A | 12/1991 | Dunson, Jr. |
| 5,071,686 A | 12/1991 | Genske et al. |
| 5,071,878 A | 12/1991 | Herschler |
| 5,083,558 A | 1/1992 | Thomas et al. |
| 5,086,804 A | 2/1992 | Ngai |
| 5,087,673 A | 2/1992 | Watanabe et al. |
| 5,091,180 A | 2/1992 | Walker et al. |
| 5,117,821 A | 6/1992 | White |
| 5,133,788 A | 7/1992 | Backus |
| 5,135,904 A | 8/1992 | Kamiya et al. |
| 5,139,831 A | 8/1992 | Mueller |
| 5,145,657 A | 9/1992 | Kobayashi et al. |
| 5,149,576 A | 9/1992 | Potts et al. |
| 5,152,814 A | 10/1992 | Nelson |
| 5,160,707 A | 11/1992 | Murray et al. |
| 5,169,217 A | 12/1992 | Orchard et al. |
| 5,183,656 A | 2/1993 | Uesaka et al. |
| 5,190,640 A | 3/1993 | Roof et al. |
| 5,192,272 A | 3/1993 | Faure |
| 5,192,342 A | 3/1993 | Baron et al. |
| 5,192,498 A | 3/1993 | Chen et al. |
| 5,199,263 A | 4/1993 | Green et al. |
| 5,207,303 A | 5/1993 | Oswalt et al. |
| 5,213,680 A | 5/1993 | Kremer et al. |

| Patent No. | Date | Name |
|---|---|---|
| 5,218,036 A | 6/1993 | Kagawa et al. |
| 5,218,147 A | 6/1993 | Shaw |
| 5,240,478 A | 8/1993 | Messina |
| 5,260,090 A | 11/1993 | Isao |
| 5,269,294 A | 12/1993 | Rogozinski |
| 5,290,331 A | 3/1994 | Miles et al. |
| 5,336,431 A | 8/1994 | Richards et al. |
| 5,344,529 A | 9/1994 | Stauffer |
| 5,356,709 A | 10/1994 | Woo et al. |
| 5,358,443 A | 10/1994 | Mitchell et al. |
| 5,409,769 A | 4/1995 | Fukumoto et al. |
| 5,415,180 A | 5/1995 | Horan |
| 5,419,812 A | 5/1995 | Beal |
| 5,439,454 A | 8/1995 | Lo et al. |
| 5,441,729 A | 8/1995 | Salce et al. |
| 5,458,848 A | 10/1995 | Burgaud |
| 5,458,861 A | 10/1995 | Buchanan et al. |
| 5,460,625 A | 10/1995 | Johnson |
| 5,466,757 A | 11/1995 | Watanabe et al. |
| 5,480,860 A | 1/1996 | Dillon |
| 5,486,387 A | 1/1996 | Mueller |
| 5,487,766 A | 1/1996 | Vannier |
| 5,494,587 A | 2/1996 | Morlec et al. |
| 5,512,144 A | 4/1996 | Stauffer |
| 5,516,526 A | 5/1996 | De la Torre |
| 5,521,268 A | 5/1996 | Ghyzel et al. |
| 5,531,987 A | 7/1996 | Bauer et al. |
| 5,538,545 A | 7/1996 | Dauber et al. |
| 5,562,127 A | 10/1996 | Fanselow et al. |
| 5,569,679 A | 10/1996 | Jacob |
| 5,578,540 A | 11/1996 | Banzi et al. |
| 5,584,986 A | 12/1996 | Bartholic |
| 5,603,696 A | 2/1997 | Williams et al. |
| 5,605,635 A | 2/1997 | David |
| 5,616,408 A | 4/1997 | Oleszczuk et al. |
| 5,620,760 A | 4/1997 | Galimberti et al. |
| 5,624,649 A | 4/1997 | Gal |
| 5,650,329 A | 7/1997 | Warner |
| 5,654,061 A | 8/1997 | Visioli |
| 5,658,801 A | 8/1997 | Poissant et al. |
| 5,667,799 A | 9/1997 | Caldwell et al. |
| 5,703,152 A | 12/1997 | Ohama |
| 5,712,044 A | 1/1998 | Fanselow et al. |
| 5,725,893 A | 3/1998 | Pittet et al. |
| 5,753,696 A | 5/1998 | Shealy et al. |
| 5,761,362 A | 6/1998 | Yang et al. |
| 5,779,679 A | 7/1998 | Shaw |
| 5,783,269 A | 7/1998 | Heilmann et al. |
| 5,789,046 A | 8/1998 | Mueller |
| 5,792,505 A | 8/1998 | Fulger et al. |
| 5,803,130 A | 9/1998 | Robben et al. |
| 5,803,249 A | 9/1998 | Harsanyi, Jr. et al. |
| 5,843,420 A | 12/1998 | Bauer et al. |
| 5,849,846 A | 12/1998 | Chen et al. |
| 5,861,096 A | 1/1999 | Mason et al. |
| 5,871,562 A | 2/1999 | Culoso |
| 5,885,566 A | 3/1999 | Goldberg |
| 5,891,508 A | 4/1999 | Barnum |
| 5,919,877 A | 7/1999 | Tanaglia |
| 5,928,744 A | 7/1999 | Heilmann et al. |
| 5,931,303 A | 8/1999 | Salvadori |
| 5,935,412 A | 8/1999 | Brainard, II |
| 5,935,547 A | 8/1999 | LeComte et al. |
| 5,948,398 A | 9/1999 | Hanamoto et al. |
| 5,958,502 A | 9/1999 | Fulger et al. |
| 5,967,061 A | 10/1999 | Ashworth et al. |
| 5,972,993 A | 10/1999 | Ptchelintsev |
| 5,989,497 A | 11/1999 | Labonte, Jr. |
| 5,998,019 A | 12/1999 | Rosenbaum et al. |
| 6,007,520 A | 12/1999 | Sudo |
| 6,010,666 A | 1/2000 | Kurokawa et al. |
| 6,012,586 A | 1/2000 | Misra |
| 6,015,536 A | 1/2000 | Lokkesmoe et al. |
| 6,030,494 A | 2/2000 | Hupa et al. |
| 6,042,640 A | 3/2000 | Isganitis et al. |
| 6,045,596 A | 4/2000 | Holland, Jr. et al. |
| 6,048,733 A | 4/2000 | Machino et al. |
| 6,057,018 A | 5/2000 | Schmidt |
| 6,060,083 A | 5/2000 | Dorr et al. |
| D427,299 S | 6/2000 | Haslebacher |
| 6,070,578 A | 6/2000 | Baughman et al. |
| 6,077,335 A | 6/2000 | Schneider et al. |
| 6,090,076 A | 7/2000 | Lane, Jr. |
| 6,094,549 A | 7/2000 | Hiraoka et al. |
| 6,099,607 A | 8/2000 | Haslebacher |
| 6,106,502 A | 8/2000 | Richmond |
| 6,106,596 A | 8/2000 | Haramoto et al. |
| 6,110,176 A | 8/2000 | Shapira |
| 6,114,586 A | 9/2000 | Devaux et al. |
| D431,353 S | 10/2000 | Mellin |
| D431,902 S | 10/2000 | Mellin |
| 6,183,708 B1 | 2/2001 | Hei et al. |
| 6,183,758 B1 | 2/2001 | Scott |
| 6,197,288 B1 | 3/2001 | Mankoo |
| 6,207,106 B1 | 3/2001 | Kurokawa et al. |
| 6,221,325 B1 | 4/2001 | Brown et al. |
| 6,228,960 B1 | 5/2001 | Tanaglia |
| 6,238,767 B1 | 5/2001 | McCormack et al. |
| 6,248,733 B1 | 6/2001 | Landgrebe et al. |
| 6,261,655 B1 | 7/2001 | Rosenbaum et al. |
| 6,267,941 B1 | 7/2001 | Sata |
| 6,277,344 B1 | 8/2001 | Hei et al. |
| 6,294,161 B1 | 9/2001 | Hiramoto et al. |
| 6,303,200 B1 | 10/2001 | Woo et al. |
| 6,312,713 B1 | 11/2001 | Korol et al. |
| 6,318,075 B1 | 11/2001 | Gunther et al. |
| 6,348,177 B1 | 2/2002 | Bartley et al. |
| 6,349,826 B1 | 2/2002 | Kapik et al. |
| 6,365,099 B1 | 4/2002 | Castrantas et al. |
| 6,403,642 B1 | 6/2002 | Berg |
| 6,403,739 B1 | 6/2002 | Tanaglia et al. |
| 6,406,767 B1 | 6/2002 | Mueller |
| 6,412,639 B1 | 7/2002 | Hickey |
| 6,414,194 B1 | 7/2002 | Bloom, Jr. et al. |
| 6,416,772 B1 | 7/2002 | Van Engelen et al. |
| 6,418,932 B2 | 7/2002 | Paschal, Jr. et al. |
| 6,426,112 B1 | 7/2002 | Boatright |
| 6,426,370 B1 | 7/2002 | Hofschneider |
| 6,432,891 B1 | 8/2002 | O'Connor |
| 6,440,391 B1 | 8/2002 | Jacob |
| 6,454,097 B1 | 9/2002 | Blanco |
| 6,458,828 B1 | 10/2002 | Sakurai et al. |
| 6,460,702 B2 | 10/2002 | Hammond |
| 6,461,631 B1 | 10/2002 | Dunn et al. |
| 6,465,068 B1 | 10/2002 | Patel et al. |
| 6,468,259 B1 | 10/2002 | Loretti et al. |
| 6,475,466 B1 | 11/2002 | Ricci et al. |
| 6,479,150 B1 | 11/2002 | Liu et al. |
| 6,479,488 B1 | 11/2002 | Di-Fabio et al. |
| 6,482,377 B2 | 11/2002 | Bartley et al. |
| 6,495,096 B1 | 12/2002 | Hamaguchi et al. |
| 6,528,080 B2 | 3/2003 | Dunn et al. |
| 6,531,111 B1 | 3/2003 | Whalen, II et al. |
| 6,552,231 B2 | 4/2003 | Jones et al. |
| 6,562,447 B2 | 5/2003 | Wu et al. |
| 6,579,444 B2 | 6/2003 | Feimer et al. |
| 6,579,543 B1 | 6/2003 | McClung |
| 6,599,472 B1 | 7/2003 | Hudson |
| 6,620,911 B1 | 9/2003 | Pettit et al. |
| 6,638,605 B1 | 10/2003 | Ankuda, Jr. et al. |
| 6,639,110 B2 | 10/2003 | Fremy |
| 6,649,193 B1 | 11/2003 | Colic |
| 6,652,845 B2 | 11/2003 | Hu et al. |
| 6,653,352 B2 | 11/2003 | Barr et al. |
| 6,656,723 B1 | 12/2003 | Phillips |
| 6,663,679 B1 | 12/2003 | Duncan |
| 6,680,194 B1 | 1/2004 | Turner |
| 6,706,257 B1 | 3/2004 | McCook et al. |
| 6,718,914 B2 | 4/2004 | Riddles |
| 6,722,295 B2 | 4/2004 | Zauderer |
| 6,723,349 B1 | 4/2004 | Hill et al. |
| 6,723,399 B2 | 4/2004 | Chundury et al. |
| 6,734,263 B2 | 5/2004 | Eadara et al. |
| 6,737,031 B2 | 5/2004 | Beal et al. |
| 6,737,089 B2 | 5/2004 | Wadsworth et al. |
| 6,743,523 B1 | 6/2004 | Woo et al. |
| 6,743,951 B2 | 6/2004 | Fremy |
| 6,761,169 B2 | 7/2004 | Eswarappa |

| | | |
|---|---|---|
| 6,761,912 B2 | 7/2004 | Forusz et al. |
| 6,764,566 B1 | 7/2004 | Griesbach, III et al. |
| 6,783,004 B1 | 8/2004 | Rinner |
| RE38,597 E | 9/2004 | Lane, Jr. |
| 6,796,958 B2 | 9/2004 | Chen et al. |
| 6,822,015 B2 | 11/2004 | Muraki |
| 6,830,794 B2 | 12/2004 | Cartledge et al. |
| 6,844,430 B2 | 1/2005 | Pesce et al. |
| 6,846,535 B2 | 1/2005 | De Groot et al. |
| 6,858,192 B2 | 2/2005 | Graham et al. |
| 6,872,241 B2 | 3/2005 | Soane et al. |
| 6,881,419 B2 | 4/2005 | Lovett |
| 6,884,797 B2 | 4/2005 | Hofmann |
| 6,890,373 B2 | 5/2005 | Nemoto et al. |
| 6,902,714 B2 | 6/2005 | Skaarup Jensen et al. |
| 6,908,885 B2 | 6/2005 | Bengs et al. |
| 6,927,305 B2 | 8/2005 | Choudary et al. |
| 7,057,016 B2 | 6/2006 | Cerletti |
| 7,203,974 B2 | 4/2007 | Jones et al. |
| 7,282,224 B1 | 10/2007 | Roederer |
| 7,371,407 B2 | 5/2008 | Farmer |
| 7,381,521 B2 | 6/2008 | Whitaker |
| 2001/0005766 A1 | 6/2001 | Fremy |
| 2001/0047038 A1 | 11/2001 | Moorman et al. |
| 2002/0015762 A1 | 2/2002 | Quinlan |
| 2002/0025983 A1 | 2/2002 | Horrobin |
| 2002/0032131 A1 | 3/2002 | O'Connor |
| 2002/0043501 A1 | 4/2002 | Irvine |
| 2002/0090398 A1 | 7/2002 | Dunn et al. |
| 2002/0110549 A1 | 8/2002 | Till |
| 2002/0115729 A1 | 8/2002 | Yang |
| 2002/0131933 A1 | 9/2002 | Delmotte |
| 2002/0133100 A1 | 9/2002 | Paschal, Jr. et al. |
| 2002/0151753 A1 | 10/2002 | Fremy |
| 2002/0156326 A1 | 10/2002 | Fremy |
| 2002/0182263 A1 | 12/2002 | Stenti et al. |
| 2003/0017183 A1 | 1/2003 | Pollock |
| 2003/0082321 A1 | 5/2003 | Kennedy et al. |
| 2003/0085170 A1 | 5/2003 | Scranton et al. |
| 2003/0108810 A1 | 6/2003 | Williamson et al. |
| 2003/0118672 A1 | 6/2003 | McPeak et al. |
| 2003/0133959 A1 | 7/2003 | Shacknai et al. |
| 2003/0152862 A1 | 8/2003 | Williamson et al. |
| 2003/0157006 A1 | 8/2003 | Hei et al. |
| 2003/0167033 A1 | 9/2003 | Chen et al. |
| 2003/0190266 A1 | 10/2003 | Tsurumi |
| 2003/0203009 A1 | 10/2003 | MacDonald |
| 2003/0203484 A1 | 10/2003 | Black et al. |
| 2004/0016410 A1 | 1/2004 | Riddles |
| 2004/0039066 A1 | 2/2004 | Crea |
| 2004/0048376 A1 | 3/2004 | Chabot et al. |
| 2004/0057972 A2 | 3/2004 | Shacknai et al. |
| 2004/0074212 A1 | 4/2004 | Yachi et al. |
| 2004/0081673 A1 | 4/2004 | Rayner et al. |
| 2004/0082667 A1 | 4/2004 | McCadden et al. |
| 2004/0086888 A1 | 5/2004 | Kornblith et al. |
| 2004/0087669 A1 | 5/2004 | Hausmanns et al. |
| 2004/0115818 A1 | 6/2004 | Puri et al. |
| 2004/0131806 A1 | 7/2004 | Barmore et al. |
| 2004/0137136 A1 | 7/2004 | Zheng et al. |
| 2004/0151826 A1 | 8/2004 | Milligan |
| 2004/0154220 A1 | 8/2004 | Holcomb |
| 2004/0156742 A1 | 8/2004 | Milan et al. |
| 2004/0157802 A1 | 8/2004 | Horwitz et al. |
| 2004/0186316 A1 | 9/2004 | Choudary et al. |
| 2004/0197339 A1 | 10/2004 | Brown |
| 2004/0213755 A1 | 10/2004 | Hochwalt et al. |
| 2004/0213774 A9 | 10/2004 | Till |
| 2004/0219126 A1 | 11/2004 | Seto et al. |
| 2004/0242818 A1 | 12/2004 | Williamson et al. |
| 2004/0265291 A1 | 12/2004 | Drake et al. |
| 2005/0025840 A1 | 2/2005 | Revnolds |
| 2005/0031651 A1 | 2/2005 | Gervais et al. |
| 2005/0031761 A1 | 2/2005 | Brucker et al. |
| 2005/0035062 A1 | 2/2005 | Hiltzik et al. |
| 2005/0054875 A1 | 3/2005 | Hei et al. |
| 2005/0058630 A1 | 3/2005 | Harris et al. |
| 2005/0069598 A1 | 3/2005 | Ribnicky et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0092070 A1 | 5/2005 | Bhatti |
| 2005/0092761 A1 | 5/2005 | Marganski et al. |
| 2005/0095653 A1 | 5/2005 | Goldstein et al. |
| 2005/0112085 A1 | 5/2005 | MacDonald et al. |
| 2005/0112176 A1 | 5/2005 | Dopson et al. |
| 2005/0112177 A1 | 5/2005 | Dopson et al. |
| 2005/0115895 A1 | 6/2005 | Simpson et al. |
| 2005/0136082 A1 | 6/2005 | Soane et al. |
| 2005/0136125 A1 | 6/2005 | Roth |
| 2005/0142096 A1 | 6/2005 | Wegner |
| 2005/0147692 A1 | 7/2005 | Roth |
| 2005/0158406 A1 | 7/2005 | McPeak et al. |
| 2005/0158424 A1 | 7/2005 | Nakano et al. |
| 2005/0169826 A1 | 8/2005 | Li et al. |
| 2005/0176778 A1 | 8/2005 | Vermeer |
| 2005/0181048 A1 | 8/2005 | Romero |
| 2005/0182076 A1 | 8/2005 | Pacheco et al. |
| 2005/0187124 A1 | 8/2005 | Li et al. |
| 2005/0191343 A1 | 9/2005 | Liang |
| 2005/0215515 A1 | 9/2005 | Bucolo et al. |
| 2005/0222275 A1 | 10/2005 | Gabizon et al. |
| 2005/0224409 A1 | 10/2005 | Harshman et al. |
| 2005/0226827 A1 | 10/2005 | Ho |
| 2005/0227910 A1 | 10/2005 | Yang et al. |
| 2005/0260306 A1 | 11/2005 | Baldus |
| 2005/0261257 A1 | 11/2005 | Vermeer |
| 2005/0265979 A1 | 12/2005 | Aoki et al. |
| 2005/0266064 A1 | 12/2005 | McCarthy |
| 2005/0281883 A1 | 12/2005 | Daniloff et al. |
| 2006/0003069 A1 | 1/2006 | Zheng et al. |
| 2006/0006120 A1 | 1/2006 | Chen et al. |
| 2006/0006121 A1 | 1/2006 | Simpson et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0052438 A1 | 3/2006 | Ho et al. |
| 2006/0127508 A1 | 6/2006 | Larkins |
| 2006/0166948 A1 | 7/2006 | Vermeer |
| 2006/0177398 A1 | 8/2006 | McCook et al. |
| 2006/0194759 A1 | 8/2006 | Eidelson |
| 2006/0210646 A1 | 9/2006 | Oku et al. |
| 2006/0281822 A1 | 12/2006 | Appleton |
| 2007/0025950 A1 | 2/2007 | Elson |
| 2007/0028772 A1 | 2/2007 | Jain et al. |
| 2007/0048386 A1 | 3/2007 | Mallozzi, Sr. et al. |
| 2007/0183936 A1 | 8/2007 | Newsam et al. |
| 2007/0243146 A1 | 10/2007 | Klock |
| 2007/0264212 A1 | 11/2007 | Ho |
| 2007/0270358 A1 | 11/2007 | de Paoliambrosi |
| 2007/0292493 A1 | 12/2007 | Brierre |
| 2008/0038219 A1 | 2/2008 | Mosbaugh et al. |
| 2008/0076831 A1 | 3/2008 | Goetz |
| 2008/0102107 A1 | 5/2008 | Lewellyn et al. |
| 2008/0146458 A1 | 6/2008 | Hollingsworth et al. |
| 2008/0193427 A1 | 8/2008 | Kaesler et al. |
| 2008/0228161 A1 | 9/2008 | Claussen et al. |
| 2008/0251081 A1 | 10/2008 | Claussen et al. |
| 2008/0260871 A1 | 10/2008 | Fruitman |
| 2008/0274153 A1 | 11/2008 | Farmer |
| 2008/0275015 A1 | 11/2008 | Potter |
| 2008/0300311 A1 | 12/2008 | Kisak et al. |
| 2008/0317680 A1 | 12/2008 | Dueva-Koganov et al. |
| 2008/0319092 A1 | 12/2008 | Singh |
| 2009/0215888 A1 | 8/2009 | Jagat et al. |
| 2009/0312273 A1 | 12/2009 | De La Torre |

FOREIGN PATENT DOCUMENTS

| | | |
|---|---|---|
| EP | 0976726 | 2/2000 |
| GB | 2028162 | 12/1979 |
| JP | 2005330199 | 12/2005 |
| WO | WO 85/00108 | 1/1985 |
| WO | WO 94/05272 | 3/1994 |
| WO | WO 00/64868 | 11/2000 |
| WO | WO 01/73096 | 10/2001 |
| WO | WO 03/015760 | 2/2003 |
| WO | WO 03/101415 | 12/2003 |

| | | |
|---|---|---|
| WO | WO 2004/064877 | 8/2004 |
| WO | WO 2004/093541 | 11/2004 |
| WO | WO 2005/054553 | 6/2005 |
| WO | WO 2005/115546 | 12/2005 |
| WO | WO 2005/117913 | 12/2005 |
| WO | WO 2006/129149 | 12/2006 |
| WO | WO 2006/135854 | 12/2006 |
| WO | WO 2007/009245 | 1/2007 |
| WO | WO 2007/016766 | 2/2007 |
| WO | WO 2007/033082 | 3/2007 |
| WO | WO 2007/033083 | 3/2007 |
| WO | WO 2007/033180 | 3/2007 |
| WO | WO 2007/056205 | 5/2007 |
| WO | WO 2007/098591 | 9/2007 |
| WO | WO 2007/126191 | 11/2007 |
| WO | WO 2008/049020 | 4/2008 |
| WO | WO 2008/098871 | 8/2008 |
| WO | WO 2010/054093 | 5/2010 |
| WO | WO 2010/062721 | 6/2010 |

OTHER PUBLICATIONS

Baer P, Thomas L, Shainhouse JZ. Treatment of osteoarthritis of the knee with a topical diclofenac solution: a randomized, controlled 6-week trial. BMC Musculoskeletal Disord. 2005; 6:44.

Barrager, et al. A Multicentered, Open-Label Trial on the Safety and Efficacy of Methylsulfonylmethane in the Treatment of Seasonal Allergic Rhinitis, The Journal of Alternative and Complementary Medicine, vol. 8, No. 2, 2002, pp. 167-173.

Berry et al. Natural Gas Odorants Desulfurization, (2004) AIChE Annual National Meeting, Austin, Texas, Nov. 7-12.

Blumenthal L, Fuchs M. *The Clinical Use of Dimethyl Sulfoxide on Various Headaches, Musculoskeletal and Other General Medical Disorders*. Annals New York Academy of Sciences 1967:572-585.

Bookman A, Williams S, Shainhouse J. *Effect of a topical diclofenac solution for relieving symptoms of primary osteoarthritis of the knee: a randomized controlled trial*. CMAJ Aug. 17, 2004; 171(4):333-338.

Brayton CF. *Dimethyl Sulfoxide (DMSO); A Review*. The Cornel Veterinarian. Jan. 1986; 76(1):61-90.

Brechner V, Cohen D, Pretsky I. *Dermal Anesthesia by the Topical Application of Tetracaine Base Dissolved in Dimethyl Sulfoxide*, Annals New York Academy of Sciences. 1967:524-531.

Brien et al. *Systematic review of the nutritional supplements dimethyl sulfoxide (DMSO) and methylsulfonylmethane (MSM) in the treatment of osteoarthritis*. Osteoarthritis and Cartilage (2008) 16:1277-1288.

Brien S, Prescott P, Lewith G. *Meta-analysis of the Related Nutritional Supplements Dimethyl Sulfoxide and Methylsulfonlymethane in the Treatment of Osteoarthritis of the Knee*. eCAM Advance Access published May 27, 2009 in 10 pages.

Brown JH. *Clinical Experience with DMSO in Acute Musculoskeletal Conditions, Comparing a Noncontrolled Series with a Controlled Double Blind Study*. Ann NY Acad Sci 1967; 141(1):496-505.

Cherian L, Robertson C. *L-Arginine and Free Radical Scavengers Increase Cerebral Blood Flow and Brain Tissue Nitric Oxide Concentrations after Controlled Cortical Impact Injury in Rats*. Journal of Neurotrauma, vol. 20, No. 1, 2003; (Jan. 2003), pp. 77-85.

Debi R, et al. *The Role of MSM in Knee Osteoarthritis: A Double Blind, RandomizedProspective Study*. Osteoarthritis and Cartilage (2008) 15 Supplemental C:C231 (426).

Demos C et al. *Dimethyl Sulfoxide in Musculoskeletal Disorders*. Ann Ny Acad Sci 1967:517-523.

Eberhardt et al. *DMSO in patients with Active Gonarthrosis. A double-blind, placebo-controlled Phase III Study*. Fortschr Med, Nov. 10, 1995: 113(31):446-450.

Evans MS, Reid KH, Sharp JB. *Dimethylsulfoxide (DMSO) blocks conduction in peripheral nerve C fibers: a possible mechanism of analgesia*. Neuroscience Letters, 150 (1993):145-148.

Feldman WE, Punch JD, Holden PC. *In vivo and in vitro effects of dimethyl sulfoxide on streptomycin-sensitive and -resistant Escherichia coli*. Ann NY Acad Sci, Jan. 27, 1975; 243:269-77.

Florain, The Solid State Structures of the Dimethylformamide and Dimethylsulfoxide Complexes of Dioxodichloromolybdenum (VI), ProQuest, 30-07B (1969), pp. 66.

Glasser D. *Dimethylsulfoxide (DMSO) "resensibilization" as potential chemotherapy for opportunistic mycobacterial disease*. Am Rev Respir Dis. Nov. 1978; 118(5):969-70.

Gorbach IN, Samtsov VS. *Therapeutic possibilities of inhalation of rifampicin with dimexide in phthisiopulmonology*. Probl Tuberk. 1991; (3):34-6.

Haigler HJ et al. *Comparison of the Analgesic Effects of Dimethyl Sulfoxide and Morphine*, Ann NY Acad Sci 1983; (411):19-27.

Hasegawa T, *Suppressive Effects of Methylsulfonylmethane (MSM) on Type II Collagen-induced Arthritis in DBA/1J Mice*. Jpn Pharmacol Ther 2004; 32 (7):421-427.

Jacob S, Appleton J. *MSM: The Definitive Guide—Chapter 6, 45-54, Part II, Chapter 7, 57-68, Chapter 8, 69-76, Chapter 10, 84-90, Chapter 21, 181-186*. California: Freedom Press, 2003.

Jacob S, Lawrence R, Zucker M, *The Miracle of MSM—The Natural Solution for Path*. New York: Library of Congress Cataloging-in-Publication Data, 1999.

Jacob SW, Herschler R. *Pharmacology of DMSO*, Cryobiology, 1985, 23(1):14-27.

Jacob, S.W. and Wood, D.C. *Dimethyl sulfoxide (DMSO): Toxicology, pharmacology, and clinical experience*. Am. J. Surg. 1967; 114(3):414-426.

Jacob et al., Interstitial Cystitis Network—Char Log, Topic: Understanding DMSO; Mar. 28, 2000; The IC Network.

Jagannath C, Reddy VM, Gangadharam PR. *Enhancement of drug susceptibility of multi-drug resistant strains of Mycobacterium tuberculosis by ethambutol and dimethyl sulphoxide*. J Antimicrob Chemother. Mar. 1995; 35(3):381-90.

Jimenez RA, Willkens RF. *Dimethyl Sulphoxide: a perspective of its use in rheumatic diseases*. J Lab Clin Med 1982; 100(4):489-500.

John, H., Laudahn, G. *Clinical Experiences with the Topical Application of DMSO in Orthopedic Diseases: Evaluation of 4,180 Cases*, Annals New York Academy of Sciences, 1967; vol. 141:506-516.

Karlson AG, Ulrich JA, *Stock solutions of rifampin remain stable in dimethylsulfoxide for at least 8 months*, Appl Microbiol. Oct. 1969; 18(4):692-3.

Kim, et al. *Efficacy of Methylsulfonylmethane (MSM) in Osteoarthritis Path of the Knee: A Pilot Clinical Trial*. Osteoarthritis and Cartilage (2006) 14:286-294.

Knowles R. *Clinical Experience with DMSO in Small Animal Practice*, Annals New York Academy Sciences (1967) 141:478-483.

Koenen NJ, Haag RF, BiaP, RoseP. *Perkutane therapie bei aktivierter Gonarthrose*. Munch Med Wochenschr 1996; 138 (31-32):534-538.

Kubota et al. *Beneficial effect of L-Arginine for Stroke-like episode in MELAS* Brain and Development, Amsterdam, JL, vol. 26, No. 7, Oct. 1, 2004; pp. 481-483.

Liubinets VI, Kruk MV. *Dimexide in the treatment of endobronchitis in patients with destructive forms of pulmonary tuberculosis*, Zh Ushn Nos Gorl Bolezn. Nov.-Dec. 1969; 29(6):68-71.

Lockie and Norcross. *A Clinical Study on the Effects of Dimethyl Sulfoxide in 103 Patients with Acute and Chronic Musculoskeletal Injuries and Inflammations*, Annals New York Academy Sciences (1967) 141:599-602.

Martin D. and Hauthal H., *Dimethyl Sulfoxide—Chapter 12*. New York: John Wiley & Sons, 1971.

Matsumoto, J. *Clincal Trials of Dimethyl Sulfoxide in Rheumatoid Arthritis Patients in Japan*, Annals New York Academy Sciences. 1967; vol. 141:560-568.

Mitinskaia LA, Iukhimenko NV, Kamaeva VF. *BCG vaccination and increasing the effectiveness of treatment of post-vaccination complications by the use of rifampicin and dimexide*. Probl Tuberk. 1994; (5):4-7.

Mohamaddi F, O'Mara K, Unusual Patient Odor Interfering with Care, Resurrection Medical Center, Chicago, Ill. (1996).

Muller U, Urbanczik R. *Influence of dimethyl sulfoxide (DMSO) on restoring sensitivity of mycobacterial strains resistant to chemotherapeutic compounds*, J Antimicrob Chemother. May 1979; 5(3):326-7.

Murav'ev IuV, Venikova MS, Peskovskaia GN, Riazantseva TA, Sigldin IaA. *Effect of dimethylsulphoxide and dimethyl sulfone*. Patol Fiziol Eksp Ter Mar.-Apr. 1991; (2):37-39.

Nash DR, Steingrube VA. *In vitro drug sensitivity of M. avium-intracellulare complex in the presence and absence of dimethyl sulfoxide*. Microbios. 1982; 35(140):71-8.

Oshima Y, Theodosakis J, Amiel D. *The Effect of Distilled Methylsulfonylmethane (MSM) on Human Chondrocytes in vitro*. World Congress on Osteoarthritis, Ft. Lauderdale, Florida; Osteoarthritis and Cartilage 2007; vol. 15 Supplemental C123:213.

Ostojic et. al. *Laboratory Testing of Cabin Air Filters for the Removal of Reduced-Sulfur Odors*. New Engine Design and Automotive Filtration SAE Special Publications 1998; 1362:41-58.

Paul M. *Interval Therapy with Dimethyl Sulfoxide*. Ann NY Acad Sci Mar. 1967; 1(141):586-598.

Paulus E. *FDA advisory committee meeting: methotrexate; guidelines for the clinical evaluation of anti-inflammatory drugs; DMSO in scleroderma*. Arthritis & Rehumatism Oct. 1986; 10(29):1289-1290.

Pennsaid Monograph, Nuvo Research, 2010.

Penrod, D., Bacharach, B., Templeton, J. *Dimethyl Sulfoxide for Incisional Path after Thoracotomy: Preliminary Report*. Annals New York Academy Sciences Mar. 15, 1967; vol. 141(1):493-495.

Potzz GE, Rampey JH, Bejamin F. *The effect of dimethyl sulfoxide (DMSO) on antibiotic sensitivity of a group of medically important microorganisms: preliminary report*. Ann NY Acad Sci. Mar. 15, 1967; 141(1):261-72.

Robertson et al. "*L-Arginine reduces neuronal damage after traumatic brain injury in the mouse*" Journal of Neurotrauma, vol. 17, No. 10, Oct. 2000, p. 945.

Ropek M, Pawlowska I, Szydlowska T. *Effects of dimethyl sulfoxide on tubercle bacilli resistant to INH*. Gruzlica. Aug. 1971; 39(8):738-41.

Rosenbaum WM, Rosenbaum EE, Jacob S. The use of dimethyl sulfoxide (DMSO) for the treatment of intractable pain in surgical patients. Surgery 1965: 58.

Roth SH, Shainouse JZ, Efficacy of Safety of a topical diclofenac solution (Pennsaid) in the treatment of primary osteoarthritis of the knee: a randomized, double-blind, controlled clinical trial. Arch Intern Med. Oct. 11, 2004;164(18):2017-23.

Seibert F, Farrelly F, Shepherd C. *DMSO and other combatants against bacteria isolated from leukemia and cancer patients*. Ann NY Acad Sci Mar. 1967; 1(141):175-201.

Shainhouse JZ, Grierson L, Naseer Z, A long-term, open-label study to confirm the safety of topical diclofenac solution containing dimethyl sulfoxide in the treatment of the osteoarthritic knee, American Journal of Therapeutics 0(0) 2010.

Shaklee Health Network, "Methyl Sulfonyl Methane," [online], 2006 [retrieved on Dec. 16, 2010]. Retrieved from the internet: <URL:http://content.hbiondemand.com/shap/monoVMN.asp?objID=100028]: p. 1-4, especially p. 1, para 1 to p. 2, para 1.

Simon L, et. al. *Efficacy and Safety of Topical Diclofenac containing Dimethyl Sulfoxide (DMSO) compared with those of Topical Placebo, DMSO Vehicle and Oral Diclofenac for Knee Osteoarthritis*. Pain, 143(2009):238-245.

Smith G, Bertone AL, Kaeding C, et al. *Anti-Inflammatory effects of topically applied dimethyl sulphoxide gel on endotoxin-induced synovitis in horses*. Am J Vet Res Sep. 1998; 59(9):1149-52.

Steinberg, A. *The employment of DMSO as an anti-inflammatory agent and steroid transporter in diversified clinical diseases*. Ann NY Acad Sci 1967, 141(1):532-550.

Szydlowska T. *In Vitro and In Vivo Studies on the role of Dimethylsulfoxide (DMSO) in Resensibilization of Bacterial Strains Resistant to Antibiotics and Chemotherapeutic Agents*. Zbl. Bakt. Hyg., I. Abt. Orig. A 239, 270-274 (1977).

Szydlowska T, Pawlowska I. *Comparative Studies on the Influence of Dimethylsulfoxide (DMSO) on Reversion to Sensitivity to Isonicotinic Acid Hydrazide (INH) and Rifampicin (RMP) in Resistant Strains of Tubercle Bacilli*. Arch Immunol Ther Exp (Warsz). 1976; 24(4):575-77.

Szydlowska T, Pawlowska I. *In vivo studies on reversion to sensitivity of INH-resistant tubercle bacilli under the influence of dimethylsulfoxide (DMSO)*. Arch Immunol Ther Exp (Warsz). 1974; 22(4):559-61.

Szydlowska T. *Studies on the role of dimethylsulfoxide in resensibilization of antibiotic-resistant bacterial strains*. Arch Immunol Ther Exp (Warsz). 1972; 20(2):193-202.

Szydlowska T. *Studies on the role of dimethylsulfoxide in resensibilization of bacterial strains resistant to sulfonamides*. Arch Immunol Ther Exp (Warsz). 1972; 20(2):203-207.

Teigland MB, Saurino V. *Clinical Evaluation of Dimethyl Sulfoxide in Equine Applications*. Ann NY Acad Sci Mar. 1967; 141(1):471-7.

Tugwell PS, Wells GA, Shainhouse JZ. Equivalence study of a topical diclofenac solution (Pennsaid) compared with oral diclofenac in symptomatic treatment of osteoarthritis of the knee: a randomized, controlled trial. J Rheumatol. Oct. 2004; 31(10):1893-5.

Usha PR, Naidu MUR. *Randomized, double-blind, parallel, placebo-controlled study of oral glucosamine, methylsulfonylmethane and their combination in osteoarthritis*. Clin Drug Invest 2004; 24(6):353-63.

Vuopala U, et. al. *The Analgesic action of DMSO ointment in arthrosis*. Acta Rheum Scand 1971; 17(1):57-60.

Wierzbicki, Homocysteine and cardiovascular disease: a review of the evidence; Diabetes and Vascular Disease Research; Jun. 2007; pp. 143-149; vol. 4, Iss 2; The British Library.

Wood, DC, Wood, J. *Pharmacologic and Biochemical Considerations of Dimethyl Sulfoxide*. Ann NY Acad Sci Jan. 1975; 243:7-19.

Zuckner, J. Uddin, J., Gantner, G.*Local Application of Dimethyl Sulfoxide and DMSO Combined with Triamcinolone Acetonide in Rheumatoid Arthritis*. Ann NY Acad. Sci. Mar. 1967; 1(141):555-9.

"Guidance on Medical Device Patient Labeling" accessed Mar. 10, 2010. http://www.fda.gov/MedicalDevices/DeviceRegulationandGuidance/GuidanceDocuments/ucm070782.htm.

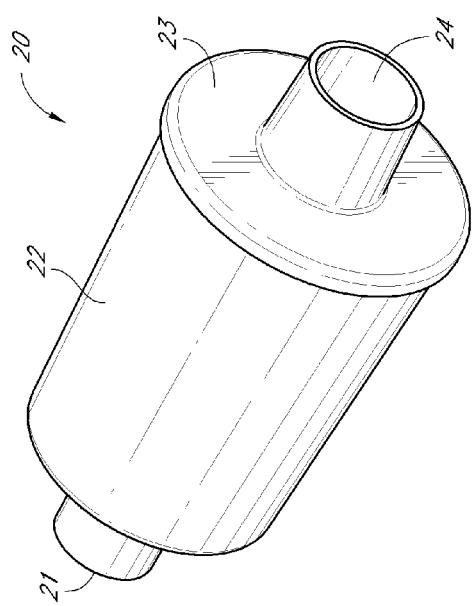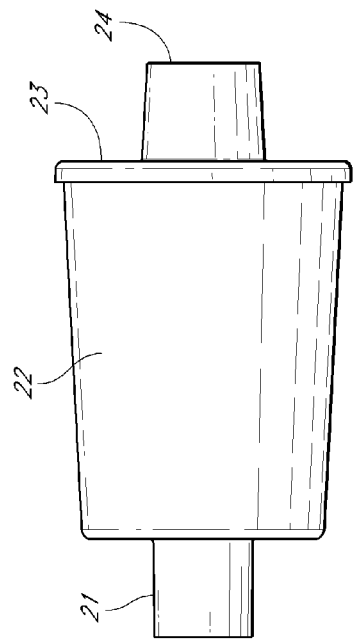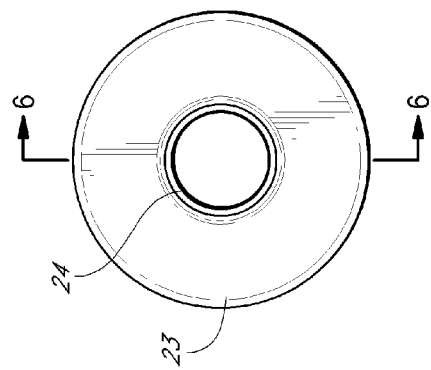

|  | Color of fiber substrate Odor eliminating power (%) | | Visibility of display part Odor eliminating power (%) | | | | | Color difference on saturated adsorption |
| --- | --- | --- | --- | --- | --- | --- | --- | --- |
|  | 100 | 0 | 100 | 75 | 50 | 30 | 0 | (grade) |
| Example 1 | light beige | light umber | 1 | 1 | 2 | 3 | 4 | — |
| Comparative Example 1 | — | white | no odor eliminating power | | | | | — |
| Example 2 | light beige | light umber | 4 | 3 | 3 | 2 | 1 | 4–5 |
| Example 3 | light dark green | brown | 4 | 3 | 2 | 2 | 1 | 4–5 |
| Example 4 | Beige | umber | 4 | 3 | 2 | 2–1 | 1 | 4–5 |
| Example 5 | very light beige | beige | 3 | 3 | 2 | 2 | 1 | 4–5 |

FIG. 14

|  | P (max) | P (mean) | PEEP | Inh:Exh | F (tot) | V (te) | VE(tot) |
| --- | --- | --- | --- | --- | --- | --- | --- |
| No Filter | 24 | 7.6 | 5.1 | 1 : 5.0 | 10 | 389 | 3.89 |
| Filter first configuration 50 (Immediately) | 24 | 7.7 | 5.0 | 1 : 5.0 | 10 | 387 | 3.88 |
| Filter first configuration 50 (10 minutes) | 23 | 7.6 | 5.0 | 1 : 5.0 | 10 | 388 | 3.87 |
| Filter second configuration 52 (Immediately) | 23 | 8.0 | 5.4 | 1 : 5.0 | 10 | 369 | 3.65 |
| Filter second configuration 52 (10 minutes) | 23 | 8.0 | 5.4 | 1 : 5.0 | 10 | 369 | 3.68 |

*Puritan Unit. Settings: V(t) =365, V(max) = 22 L/min, Square Function, PEEP = 5.0, with humidifier

FIG. 15

|  | P (max) | P (mean) | PEEP | Inh:Exh | F (tot) | V (te) | VE(tot) |
|---|---|---|---|---|---|---|---|
| No Filter | 22 | 9.5 | 5.1 | 1 : 2.3 | 10 | 381 | 3,81 |
| Filter first configuration 50 (Immediately) | 22 | 9.6 | 5.1 | 1 : 2.3 | 10 | 380 | 3.80 |
| Filter first configuration 50 (10 minutes) | 22 | 9.7 | 5.0 | 1 : 2.3 | 10 | 380 | 3.80 |
| Filter second configuration 52 (Immediately) | 21 | 9.8 | 5.5 | 1 : 2.3 | 10 | 336 | 3.27 |
| Filter second configuration 52 (10 minutes) | 21 | 9.8 | 5.4 | 1 : 2.3 | 10 | 342 | 3.42 |

*Puritan Unit. Settings: V(t) =365, V(max) = 22 L/min, Ramp Function, PEEP = 5.0, with humidifier

FIG. 16

|  | P (max) | P (mean) | PEEP | Inh:Exh | F (tot) |
|---|---|---|---|---|---|
| No Filter | 25 | 10 | 5.0 | 1 : 1.8 | 18 |
| Filter first configuration 50 (Immediately) | 18 | 9.8 | 5.0 | 1 : 1.8 | 19 |
| Filter first configuration 50 (2 minutes) | 18 | 10 | 5.2 | 1 : 2.3 | 17 |
| Filter first configuration 50 (5 minutes) | 19 | 9.7 | 5.1 | 1 : 2.1 | 13 |
| Filter first configuration 50 (10 minutes) | 16 | 9.6 | 5.1 | 1 : 1.9 | 18 |

*Puritan Unit.

FIG. 17

|  | P (max) | P (mean) | PEEP | Inh:Exh | F (tot) | V (te) | VE(tot) |
|---|---|---|---|---|---|---|---|
| No Filter | 28 | 8.1 | 5.2 | 1 : 5.0 | 10 | 369 | 3.69 |
| Filter first configuration 50 (after 10 minutes) | 28 | 8.1 | 5.2 | 1 : 5.0 | 10 | 374 | 3.74 |
| Filter second configuration 52 (after 10 minutes) | 26 | 8.5 | 5.4 | 1 : 5.0 | 10 | 347 | 3.40 |

*Puritan Unit. Settings: V(t) =365, V(max) = 22 L/min, Square Function, PEEP = 5.0

FIG. 18

| Time | P(max) | P(mean) | PEEP | Filter Status |
|---|---|---|---|---|
| 0 min | 11 | 4 | 5 | No filter |
| 1 min | 11 | 4 | 5 | No filter |
| 2 min | 11 | 4 | 5 | Filter first configuration 50 |
| 5 min | 10 | 5 | 5 | Filter first configuration 50 |
| 6 min | 10 | 5 | 5 | Filter first configuration 50 |
| 7 min | 10 | 5 | 5 | Filter first configuration 50 |
| 10 min | 10 | 6 | 5 | Filter first configuration 50 |
| 11 min | 9 | 5 | 3 | Filter second configuration 52 |
| 12 min | 10 | 5 | 3 | Filter second configuration 52 |
| 15 min | 10 | 5 | 3 | Filter second configuration 52 |
| 16 min | 10 | 4 | 5 | Filter first configuration 50 |
| 17 min | 11 | 4 | 5 | Filter first configuration 50 |

*Drager Unit. PEEP = 5

FIG. 19

| | P (max) | P (mean) | PEEP | Inh:Exh | F (tot) | V (te) | DMS |
|---|---|---|---|---|---|---|---|
| Pre-Filter | 23 | 7.3 | 5.0 | 1 : 5.0 | 10 | 361 | |
| Post-Filter | 22 | 7.4 | 4.9 | 1 : 5.0 | 10 | 355 | 0.4 mL |
| 15 | 21 | 7.2 | 5.1 | 1 : 5.0 | 10 | 359 | |
| 30 | 21 | 7.2 | 5.0 | 1 : 5.0 | 10 | 358 | |
| 60 (1 hour) | 21 | 7.2 | 5.0 | 1 : 5.0 | 10 | 359 | |
| 90 | 21 | 7.1 | 5.0 | 1 : 5.0 | 10 | 354 | |
| 120 (2 hour) | 20 | 7.1 | 5.0 | 1 : 5.0 | 10 | 362 | 0.4 mL |
| 150 | 20 | 7.0 | 5.0 | 1 : 5.0 | 10 | 353 | |
| 180 (3 hour) | 20 | 7.0 | 5.0 | 1 : 5.0 | 10 | 355 | |
| 210 | 20 | 7.0 | 5.0 | 1 : 5.0 | 10 | 360 | |
| 240 (4 hour) | 20 | 7.0 | 4.9 | 1 : 5.0 | 10 | 353 | 0.4 mL |
| 270 | 20 | 7.0 | 5.0 | 1 : 5.0 | 10 | 353 | |
| 300 (5 hour) | 20 | 7.0 | 5.0 | 1 : 5.0 | 10 | 357 | |
| 330 | 20 | 7.0 | 5.1 | 1 : 5.0 | 10 | 357 | |
| 360 (6 hour) | 20 | 7.0 | 5.0 | 1 : 5.0 | 10 | 356 | |

*Settings: V(max) = 22 L/min, f =10, V(t) = 365, T(pl) = 0, V(sens) = 0, PEEP = 5.0, Square function

FIG. 20

ACTIVATED CARBON SYSTEMS FOR FACILITATING USE OF DIMETHYL SULFOXIDE (DMSO) BY REMOVAL OF SAME, RELATED COMPOUNDS, OR ASSOCIATED ODORS

RELATED CASES

This application is a continuation-in-part of International Application PCT/US2009/063006, filed on Nov. 2, 2009, which claims the benefit of U.S. Provisional Application No. 61/110,875, filed on Nov. 3, 2008. This application is also a continuation-in-part of U.S. patent application Ser. No. 12/066,485, filed on Mar. 11, 2008, which is the United States National Phase under 35 U.S.C. §371 of International Application No. PCT/US2006/035321, filed on Sep. 11, 2006, which claims the benefit of United States Provisional Application Nos. 60/716,271, filed on Sep. 12, 2005; 60/716,336, filed on Sep. 12, 2005; 60/716,278, filed on Sep. 12, 2005; 60/716,369, filed on Sep. 12, 2005. The contents of all of the above applications are expressly incorporated in their entirety by reference herein.

BACKGROUND OF THE INVENTION

1. Field of the Invention

Embodiments of the present invention relate generally to materials for facilitating the administration of dimethyl sulfoxide (DMSO). In one embodiment, carbon filters are used in conjunction with the administration of DMSO to facilitate the administration of DMSO. Other embodiments of the present invention relate generally to materials for facilitating the administration of DMSO and associated compounds. In some embodiments, these materials comprise adsorbents for the removal of the odors and compounds resulting from the metabolism or degradation of DMSO and associated compounds. In other embodiments, these materials comprise clean air members and fabrics that absorb odors or compounds. In further embodiments, these materials comprise a clean air supply assembly for removing odors and compounds. In yet other embodiments, these materials comprise indicators to reveal the presence or absence of DMSO and associated compounds.

2. Description of the Related Art

Traumatic brain injury and stroke generally cause a reduction in cerebral blood flow (CBF), which may cause additional damage to the brain. Applicant believes that there are presently no known therapeutic agents which increase CBF in a sustained fashion (for at least several days) after traumatic brain injury. (Narayan K, and NIH Collaborative Committee. Clinical trials in head injury. J. Neurotrauma. 2002; 19(5): 503-57, herein incorporated by reference).

DMSO has been shown to increase CBF in a variety of brain injuries including stroke and head trauma in animals and humans. The combination of DMSO with fructose 1,6-diphosphate has been reported to of benefit to victims of acute and chronic human stroke. The mechanism of DMSO action for increasing CBF after brain injury is not clear but may be due to its ability to: i) reduce cerebrovascular reactivity, ii) disaggregate platelets in blood vessels thus augmenting blood fluidity by decreasing blood viscosity and iii) reducing intracranial pressure, thus allowing compressed blood vessels in brain tissue to return to a more normal hemodynamic state. DMSO is not known to affect vascular nitric oxide, ADMA or endothelin-1. (See de la Torre, J. C. and Surgeon, J. W.: Dexamethasone and DMSO in cerebral infarction. Stroke, 7:577-583, 1976; de la Tone, J. C., Kawanaga, H. M., Goode, D. J., Johnson, C. M., Kajihara, K., Rowed, D. W. Mullan, S.: *Dimethyl sulfoxide in CNS trauma.* Ann. N.Y. Acad. Sci., 243:362-389, 1975; Brown F D, Johns L M, Mullan S. *Dimethyl sulfoxide in experimental brain injury, with comparison to mannitol.* J. Neurosurg. 1980 July; 53(1):58-62; Karaca M, Kilic E, Yazici B, Demir S, de la Torre J C. *Ischemic stroke in elderly patients treated with a free radical scavenger-glycolytic intermediate compound.* Neurol Res, 24:73-80, 2002; Karaca, M., Bilgin, U., Akar, M. and de la Torre, J. C.: *Dimethyl sulfoxide lowers ICP after closed head trauma.* Eur. J. Clin. Pharmacol., 40:113-114, 1991, each of which is incorporated by reference in its entirety, herein).

Ischemia has been proposed to cause an excess increase in the extracellular concentration of glutamate, an excitotoxic amino acid, in the central nervous system. (Benveniste H, Drejer J, Schousboe A, Diemer NH: *Elevation of the extracellular concentrations of glutamate and aspartate in rat hippocampus during transient cerebral ischemia monitored by intracerebral microdialysis.* J Neurochem 1984; 43: 1369-74, herein incorporated by reference in its entirety).

Although DMSO has been shown to be safe and provide good results for the treatment of patients with head trauma (among other indications) it has never been accepted as a standard treatment because of the extremely offensive odor produced by the treatment. Odors and chemicals resulting from the treatment of patients with DMSO and related compounds can be so oppressive as to diminish the effectiveness and receptiveness of the medical staff. (Prior, D. et al, 2000, *Oncology Nurses' Experience of Dimethyl Sulfoxide Odor, Cancer Nursing*; vol. 23, No. 2, herein incorporated by reference in its entirety). Such odors may be likened to the smell of rotten eggs. Doctors have reported DMSO related odors as "evocative of rotten oysters and garlic" that cause nausea, dizziness, and revulsion because of a strong, penetrating and highly unpleasant odor preventing care workers from staying in DMSO treated patient rooms for more than several seconds. (Mohamaddi, F., M. D. and O'Mara, K. D O, March 1996 *Correspondence to the Editor, "Unusual Patient Odor Interfering with Care,"* Annals of Emergency Medicine, herein incorporated by reference in its entirety). DMSO-related odors can be smelled several yards from patients' rooms and can last two days (or longer) after treatment. Thus, DMSO-related odors are a significant barrier to the use of DSMO in clinical settings.

SUMMARY

New procedures are emerging which require the treatment of seriously ill persons by using far larger volumes of DMSO than at present. The resulting highly oppressive odors may emanate from any part of the patient's body. The capture of these odors can be crucial to the success of the new medical procedures.

Prior to Applicant's discoveries, Applicant is aware of no known effective methods currently in use for the successful removal of noxious odors associated with DMSO administration. Previous odor collecting disposables containing activated carbon for other applications have been directed toward specific bodily areas and fluids, but not for removal of metabolites of DMSO. In addition, the need for compact, easily positioned air cleaning devices has not been fully addressed. Currently, the intravenous administration of DMSO has been limited by side effects associated with the noxious odors. To facilitate access to DMSO treatments for seriously ill or injured patients, the use (and ultimate success) of these treatment methods will depend on the availability of highly effective air cleaning devices for the comfort and protection of the medical staff and visitors. Thus, there is a need for compositions, devices, and methods for the removal of DMSO metabolites and related compounds which will remove these chemicals and/or their noxious odors, as well as indicators to determine the presence of these compounds.

DMSO and its related compounds are highly promising therapeutic agents for use in the treatment of head injuries. The phrases "DMSO associated compounds", "associated compounds", or "related compounds" as used herein shall be given their ordinary meaning and shall include degradation compounds, derivatives, precursors, and metabolites of DMSO, such as methylsulfonylmethane (MSM or $DMSO_2$) and dimethyl sulfide or methylthiomethane (DMS). Metabolites include compounds to which DMSO is converted within the cells of a mammal. For example, the pharmaceutical compositions of several embodiments of the present invention may include a metabolite of DMSO instead of DMSO.

To date, DMSO related compounds have been under-utilized due the extremely offensive odor associated with its use. This vast potential but lack of use in the market is directly attributable to the odors associated with DMSO use. Thus, a system to facilitate the use of DMSO as a method to treat patients (by reducing the odors associated with DMSO) is a long felt, but unsolved need in the treatment of patients. Despite the failure of others attempting to resolve the odor associated with DMSO, there is a need for compositions, devices, and methods for the removal of DMSO metabolites and related compounds which will remove these chemicals and/or their noxious odors.

In several embodiments, there is provided a system for reducing the concentration of a dimethyl sulfoxide (DMSO) metabolite having an undesired odor, wherein the system comprises a breathing system suitable for placement in fluid communication with a subject, wherein the breathing system comprises a first filter, a ventilator, and a HEPA filter, wherein each of the filters is suitable for placement in fluid communication with one another, wherein the first filter comprises an adsorber and at least one sieve screen and the filter causes no more than a 10% decrease in air flow and no more than a 10% change in pressure in the ventilator, wherein the adsorber comprises about 10 grams to about 100 grams of activated carbon, wherein the ventilator is suitable for transporting moist air comprising the DMSO metabolite from a subject to an exhaust port and wherein contact of the DMSO metabolite with the first filter allows the first filter to capture at least 75% of the DMSO metabolite, thereby reducing the concentration of the DMSO metabolite having an undesired odor. In some embodiments, the adsorber further comprises copper oxide. In several embodiments, the DMSO metabolites are produced by an individual receiving DMSO treatment. In some embodiments, an individual is receiving DMSO treatment for one or more of traumatic brain injury, ischemic stroke, atherosclerosis, neurodegeneration, and spinal cord trauma.

In several embodiments, there is provided a system for reducing the concentration of a dimethyl sulfoxide (DMSO) metabolite having an undesired odor, wherein the system comprises a gas-line configured for fluid communication with the lungs of a patient, wherein the gas-line comprises a filter suitable for fluid connection to a gas exchange device; and at least one accessory. In several embodiments, the filter comprises an adsorber comprising about 10 g to 100 g of activated carbon. In some embodiments, the adsorber further comprises copper oxide. In some embodiments, the filter causes no more than a 10% decrease in flow in the fluid-line.

In several embodiments, there is provided a method for reducing the concentration of a dimethyl sulfoxide (DMSO) metabolite having an undesired odor, comprising passing a DMSO metabolite through a breathing system in fluid communication with a subject wherein the breathing system comprises a first filter, a ventilator and a HEPA filter in fluid communication, wherein the ventilator is configured for transporting moist air comprising the DMSO metabolite from a subject to an exhaust port, and contacting the DMSO metabolite with the first filter to capture at least 75% of the DMSO metabolite, thereby reducing the concentration of the DMSO metabolite. In several embodiments, the first filter absorbs at least 90% of the DMSO metabolite. In several embodiments, the first filter causes no more that a 5 mm Hg change in pressure in the ventilator. In several embodiments, the methods are used to reduce the concentration of DMSO metabolites that, in several embodiments, are produced by an individual receiving DMSO treatment, for treatment of, for example, a head-injury, neurodegeneration, ischemic stroke, atherosclerosis, and spinal cord trauma.

In still additional embodiments, there is provided a method for reducing the concentration of a dimethyl sulfoxide (DMSO) metabolite having an undesired odor, comprising conveying a DMSO metabolite through a breathing system in fluid communication with a subject, wherein the breathing system comprises a first filter, a ventilator and a HEPA filter in fluid communication, wherein the ventilator is configured for transporting moist air comprising the DMSO metabolite from a subject to an exhaust port, wherein the first filter comprises an adsorber and at least one sieve screen, and reducing the concentration of the DMSO metabolite at least 75% by capturing the DMSO metabolite with the first filter.

In several embodiments that comprise a HEPA filter, the HEPA filter is positioned between the subject and the filter. In several embodiments, the first filter is positioned downstream of the HEPA filter. In other embodiments, other filter positions are used (e.g., HEPA filter positioned after the first filter or in parallel with the first filter). In additional embodiments, other filters are used (either in place of or in addition to the HEPA filter). For example, an ionic filter is used in some embodiments. Electrostatic filters are used in some embodiments. Molecular sieves are also used in several embodiments. Combinations of various types of filters are also used, depending on the embodiment.

In some embodiments, the at least one sieve screen is configured to allow the DMSO metabolite to flow through the first filter while containing the adsorber within the filter. In some embodiments, the sieve screen(s) functions to remove particulate (e.g., moisture droplets or dust particles) from the system, thereby increasing the efficiency of DMSO (or related compound or related odor removal). In several embodiments, the sieve screen(s) comprises polyester. In some embodiments, the sieve screen(s) comprises a polyester-based lofted material. In still additional embodiments, the sieve screen(s) further comprises a tackifier applied to at least a portion of one side of the at least one sieve screen. In some embodiments, tackifier increases the adsorber containment efficiency of the sieve screen. Additionally, in some embodiments, the tackifier further improves the removal of DMSO (or related compounds or related odors).

In one embodiment, the first filter causes no more than 5 mm Hg change in pressure in the ventilator. In several embodiments, the minimized change in pressure provides an increased degree of comfort to a subject whose breathing is being assisted by the ventilator (reduces the feel of "breathing against" a device). Moreover, in several embodiments, the generally constant pressure in the system reduces the likelihood of pressure-spike-induced damage to the components of the system, thereby increasing the durability of the system for long-term use. Additionally, the generally constant pressure in the system advantageously allows the system to be used for a range of patients having a wide range of tidal volumes.

In several embodiments, the breathing system is suitable for placement in fluid communication with the lungs of the subject. In some embodiments, fluid communication is accomplished through fitting a subject with a face mask. In some embodiments, fluid communication is accomplished through the introduction of an endotracheal tube. In some embodiments, the general condition of the subject may define what mode of fluid communication with the lungs is used. For example, a subject who is being treated with DMSO, but is conscious may only need to be outfitted with a face mask. In contrast, those patients who are unconscious and/or in respiratory distress may be outfitted with an endotracheal tube.

In several embodiments, the systems provided herein comprise at least one accessory. In some embodiments, such accessories include but are not limited to specialized filters. For example, in some embodiments, the accessory is a biological filter configured to reduce viruses or bacteria. Such accessories are particularly advantageous when the systems are employed in hospital settings. In such cases, the reduction of viral or bacterial load may assist in preventing transfer of an illness from the subject being treated to other persons in the hospital or care facility (e.g., visitors, nurses, doctors etc.). Likewise, if a subject is immune compromised, the accessory may reduce the risk of the subject acquiring an illness. In some embodiments, the accessory is a liquid trap to remove liquid from the breathing system. While in some cases, humidified air is preferable, excess liquid (saliva or condensation from expired air) may increase the risk of mold or fungus growth within the components of the system. In some embodiments, the accessory is a heat sink configured to cool the breathing system. In some embodiments, this is advantageous because there may be a buildup of heat due to one or more of re-circulating air, increased moisture in the breathing system, heat transfer from the active components of the breathing system, and the like. Increased temperatures may cause de-humidification of the airways of a subject using the breathing system. Increased temperatures may also increase risk of hyperthermia, which could in turn induce increases in breathing and/or heart rate, either of which could lead to complications for a subject receiving treatment. In some embodiments, the heat sink functions in an inverse fashion (e.g., to provide heat to a subject, for example to reduce risk of hyperthermia). The relative position of the accessory may be determined by the systems or methods in use. For example, a biological filter may be positioned upstream of the filter in some embodiments. However, in other embodiments, it may be preferable to position other accessories in other locations.

In one embodiment, the invention comprises a method for treating a patient with DMSO, wherein the patient is connected to a ventilator. The ventilator comprises a carbon filter to capture odors associated with DMSO administration and/or metabolism. In one embodiment, the carbon filter contains about 10 g to about 100 g of activated carbon. In one embodiment, the carbon filter contains about 10 g to about 100 g of activated carbon for use in fluid communication, or in line, with an odor source. In some embodiments a fluid can be or relate to a gas or a liquid, and fluid communication or fluid connection can refer to the fluid being able to flow between points in fluid communication or fluid connection. In one embodiment, the carbon filter contains about 200 g of activated carbon. In one embodiment, the carbon filter contains about 200 g of activated carbon for use with two lines or IVs. In one embodiment, the housing is about 2¼ inches in diameter, has a chamber length of about 3¼ inches, and an overall length of about 4 inches including the housing port. In one embodiment, the cap is about 2½ inches in diameter and has a length of about 1 inch including the cap port. In one embodiment, the housing port has in inner diameter of about ¾ of an inch. In one embodiment, the housing port has in outer diameter of about 0.85 inches. In one embodiment, the cap port has in inner diameter of about 0.88 inches. In one embodiment, the cap port 24 has in outer diameter of about 1 inch.

In several embodiments, multiple filters are used (e.g., simultaneously or sequentially). For example, in one embodiment, two, three or four filters are used, wherein each filter has about 30-100 g activated carbon. In some embodiments, each filter has the same amount of carbon. In other embodiments, the amount of carbon in at least one filter is different than the others. In several embodiments, more than four filters are used in a system.

Activated carbon, as used herein, may be used interchangeably with activated charcoal, or coal. The effective use of a carbon filter in ventilators according to several embodiments of the present invention has surprising advantages. Typically, the amount of carbon needed to capture the odors associated with DMSO would have been prohibitive to make a filter that would be small enough to fit into a standard sized ventilator. The ability of a filter according to one or more embodiments herein to be used effectively in a standard hospital ventilator is also unexpected because such ventilators are extremely sensitive to pressure variations. Filters according to several embodiments herein do no cause significant pressure disruptions.

In one embodiment, the invention comprises a device to purify the air at a DMSO delivery or metabolism site. For example, a clean air device that removes DMSO metabolites and/or DMSO odors may be well-suited for hospital rooms where a patient is receiving DMSO or in a room where a patient is recovering after receiving DMSO therapy. In one embodiment, the clean air device comprises a portable, collapsible, adjustably directable clean air delivery supply assembly and enclosure for use in DMSO treated medical patient environments to provide localized clean air free of the odors, DMS, and/or compounds resulting from the metabolism of DMSO and DMSO associated compounds, including, but not limited to, hydrogen sulfide and potentially methyl mercaptan. In one embodiment, the clean air device comprises a portable air filtration unit comprising a carbon filter. In one embodiment, the clean air device comprises a tent.

In one embodiment, a collection device to funnel odor associated with treatment of a patient with DMSO includes an adsorber comprising activated carbon and an endotracheal tube. In one embodiment, a collection device to funnel odor associated with treatment of a patient with DMSO includes an adsorber comprising activated carbon and an oxygen mask. In one embodiment, a collection device to funnel odor associated with treatment of a patient with DMSO includes an adsorber comprising activated carbon and a bladder device with an exhaust tube and a plug to seal an orifice. In one embodiment, a collection device to funnel odor associated with treatment of a patient with DMSO includes an adsorber comprising activated carbon and a tent over the patient's head.

In one embodiment, a system to remove odor includes an adsorber, a collection device to funnel the majority of the odor to the adsorber, and an air filtration system to remove any remaining odor from surrounding air.

In one embodiment, an air filtration system includes a portable canister sized and configured to be small enough to place near a patient for ease of use in movement with a patient, a battery, a fan configured to collect odor, and a replaceable adsorber configured to remove an amount of odor anywhere within a range of 10%-50% DMSO IV. In various embodiments, the range can be 15-40% DMSO IV, 20-35% DMSO IV, 25-30% DMSO IV, or 28% DMSO IV.

In one embodiment, a method for facilitating treatment of a patient with DMSO includes providing a patient ventilation system and providing a filter configured for placement in the ventilation system. In one embodiment the ventilation system comprises a contained fluid-line. In one embodiment, the fluid-line is a tube. In one embodiment, the filter comprises activated carbon. In one embodiment, the filter comprises between about 10 g to 100 g of the activated carbon and absorbs at least 75% of all odors associated with the administration of DMSO to the patient. In one embodiment, the filter absorbs at least 90% of all odors associated with the administration of DMSO to the patient. In one embodiment, the filter does not cause significant pressure disruption in the ventilation system. In one embodiment, the filter causes no more than a 5% decrease in flow in the ventilation system.

In one embodiment, a method for facilitating treatment of a patient with DMSO includes providing one or more patient ventilation systems and providing a filter configured for placement in communication with the one or more ventilation systems. In one embodiment, the filter comprises activated carbon. In one embodiment, the filter comprises about 200 g of the activated carbon and absorbs at least 75% of all odors associated with the administration of DMSO to the patient.

In one embodiment, a method for reducing the concentration of a DMSO metabolite, or the odors associated with the DMSO metabolite, includes passing a DMSO metabolite or associated odor in to a filter, the filter comprising activated carbon; and contacting the DMSO metabolite or associated odor with the filter. In one embodiment, the DMSO metabolites are produced by an individual receiving DMSO treatment. In one embodiment, the filter is a mesh filter. In one embodiment, the filter is coupled to a face mask. In one embodiment, the filter is in fluid communication with an endotracheal tube. In one embodiment, the filter is in fluid communication with a ventilator. In one embodiment, the filter is in fluid communication with a bladder device with an exhaust tube and a plug to seal an orifice. In one embodiment, the filter can be in one or more canisters in a room.

In one embodiment, a method of treating a patient with brain injury or a patient who has suffered a stroke includes providing a composition comprising DMSO in a therapeutically effective dose, administering the composition to the patient, and passing breath exhaled by the patient through a filter containing an adsorbent, the adsorbent comprising activated carbon.

In one embodiment, a collection device to funnel odor associated with treatment of a patient with DMSO includes an adsorber comprising activated carbon, and an endotracheal tube. In one embodiment, a collection device to funnel odor associated with treatment of a patient with DMSO includes an adsorber comprising activated carbon, and an oxygen mask. In one embodiment, a collection device to funnel odor associated with treatment of a patient with DMSO includes an adsorber comprising activated carbon, and a bladder device with an exhaust tube and a plug to seal an orifice. In one embodiment, a collection device to funnel odor associated with treatment of a patient with DMSO includes an adsorber comprising activated carbon, and a tent over the patient's head.

In one embodiment, a system to remove odor includes an adsorber, a collection device to funnel the majority of the odor to the adsorber, and an air filtration system to remove any remaining odor from surrounding air.

In one embodiment, an air filtration system includes a portable canister sized and configured to be small enough to place near a patient for ease of use in movement with a patient, a battery, a fan configured to collect odor, and a replaceable adsorber configured to remove an amount of odor at 28% DMSO IV.

Specifically, in one embodiment, a method for reducing the concentration of a dimethyl sulfoxide (DMSO) metabolite having an undesired odor, includes passing a DMSO metabolite through a breathing system in fluid communication with a subject. In one embodiment, the breathing system includes a filter, a ventilator and a HEPA filter in fluid communication. In one embodiment, the ventilator is configured for transporting moist air including the DMSO metabolite from a subject to an exhaust port. In one embodiment, the HEPA filter is positioned between the subject and the filter.

In one embodiment, the method also includes positioning the filter downstream of the HEPA filter. In one embodiment, the filter includes an adsorber and at least one sieve screen. In one embodiment, the adsorber includes about 10 grams to about 100 grams of activated carbon. In one embodiment, at least one sieve screen is configured to allow the DMSO metabolite to flow through the filter while containing the adsorber within the filter. In one embodiment, the at least one sieve screen includes polyester. In one embodiment, the filter causes no more than a 10% decrease in air flow and no more than a 10% change in pressure in the ventilator. In one embodiment, the method also includes contacting the DMSO metabolite with the filter to capture at least 75% of the DMSO metabolite, thereby reducing the odor associated with the DMSO metabolite.

In one embodiment, the at least one sieve screen includes a polyester-based lofted material. In one embodiment, the at least one sieve screen further includes a tackifier applied to at least a portion of one side of the at least one sieve screen. In one embodiment, the filter is in fluid communication with a face mask. In one embodiment, the filter is in fluid communication with an endotracheal tube. In one embodiment, the filter is in fluid communication with a device placed in a bladder including an input line for instilling DMSO, an exhaust tube and a plug to seal a urethra. In one embodiment, the ventilator further includes an accessory in fluid-communication with the filter, the filter placed downstream of the accessory. In one embodiment, the filter causes no more than 5 mmHg change in pressure in the ventilator. In one embodiment, the adsorber further includes copper oxide. In one embodiment, the DMSO metabolites are produced by an individual receiving DMSO treatment.

In one embodiment, a collection device to funnel odor associated with treatment of a patient with dimethyl sulfoxide (DMSO), includes a contained fluid-line and a filter. The contained fluid-line extends from an odor-source. The fluid-line includes a filter fluidly connected to a gas exchange device. In one embodiment, the filter includes an adsorber including activated carbon and at least one sieve screen. In one embodiment, the sieve screen is configured to allow an odor to flow to pass through the filter while preventing the adsorbent from entering or exiting the filter. In one embodiment, the at least one sieve screen includes a polyester based lofted material. In one embodiment, the filter causes no more than a 10% decrease in flow in the fluid-line.

In one embodiment, the collection device also includes a mask in fluid connection with the filter. In one embodiment, the collection device also includes an endotracheal tube in fluid connection with the filter. In one embodiment, the collection device also includes a bladder device with an exhaust tube and a plug to seal an orifice, the bladder device in fluid connection with the filter. In one embodiment, the at least one sieve screen further includes a tackifier applied to at least a portion of one side of the at least one sieve screen. In one embodiment, the fluid-line further includes an accessory, the filter placed downstream of the accessory with respect to the odor-source. In one embodiment, the filter includes between about 10 g to 100 g of the activated carbon. In one embodiment, the collection device also includes a collection device to funnel the majority of the odor to the adsorber and an air filtration system to remove any remaining odor from surrounding air.

In one embodiment, an air filtration system, includes a portable canister sized and configured to be small enough to place near a patient for ease of use in movement with a patient, a battery, a fan configured to collect odor, and a replaceable adsorber configured to remove an amount of odor at a range of 20-35% DMSO IV.

In one embodiment, a method for facilitating treatment of a patient with dimethyl sulfoxide (DMSO) includes the steps of providing a patient breathing system and providing a filter configured for placement in the breathing system and passing odors associated with the administration of DMSO to the patient through the filter. In one embodiment, the filter includes activated carbon. In one embodiment, the filter includes between about 10 g to 100 g of the activated carbon and absorbs at least 75% of all odors associated with the administration of DMSO to the patient.

In one embodiment, the filter absorbs at least 90% of all odors associated with the administration of DMSO to the patient. In one embodiment, the filter does not cause significant pressure disruption in the breathing system. In one embodiment, the filter causes no more than a 5% decrease in flow in the breathing system.

In one embodiment, a method for facilitating treatment of a patient with dimethyl sulfoxide (DMSO), including the steps of providing one or more patient gas exchange systems, providing a filter configured for placement in communication with the one or more gas exchange systems, and passing odors associated with the administration of DMSO to the patient through the filter. In one embodiment, the filter includes activated carbon. In one embodiment, the filter includes about 200 g of the activated carbon and absorbs at least 75% of all odors associated with the administration of DMSO to the patient.

In one embodiment, a method of treating a patient with brain injury or a patient who has suffered a stroke, includes the steps of providing a composition including dimethyl sulfoxide in a therapeutically effective dose, administering the composition to the patient; and passing breath including a dimethyl sulfoxide metabolite exhaled by the patient through a filter containing an adsorbent, the adsorbent including activated carbon.

In one embodiment, a method for reducing the concentration of a dimethyl sulfoxide (DMSO) metabolite having an undesired odor, includes the steps of passing a DMSO metabolite through a ventilator, providing a filter for adsorbing at least 90% of the DMSO metabolite, positioning the filter downstream of the at least one accessory, and contacting the DMSO metabolite with the filter to capture at least 90% of the DMSO metabolite, thereby reducing the odor associated with the DMSO metabolite. In one embodiment, the ventilator includes at least one accessory. In one embodiment, the ventilator is configured for transporting air including the DMSO metabolite from a subject to an exhaust port. In one embodiment, the at least one accessory is positioned between the subject and the exhaust port. In one embodiment, the at least one accessory is in fluid communication with the subject and the exhaust port. In one embodiment, the filter is in fluid communication with the ventilator. In one embodiment, the filter includes an adsorber. In one embodiment, the adsorber includes activated carbon, In one embodiment, the filter causes no more than a 10% decrease in air flow in the ventilator.

In one embodiment, an odor collection system to contain odor associated with treatment of a patient with dimethyl sulfoxide (DMSO) includes a contained gas-line in fluid communication with the lungs of a patient, a filter and at least one accessory. In one embodiment, the gas-line includes the filter fluidly connected to a gas exchange device. In one embodiment, the filter includes an adsorber including activated carbon and at least one sieve screen. In one embodiment, the sieve screen is configured to allow an odor to flow to pass through the filter while preventing the adsorbent from entering or exiting the filter. In one embodiment, the at least one sieve screen includes a polyester based lofted material. In one embodiment, the filter causes no more than a 10% decrease in flow in the fluid-line.

In one embodiment, the at least one accessory is a biological filter configured to reduce viruses. In one embodiment, the at least one accessory is a biological filter configured to reduce bacteria. In one embodiment, the at least one accessory is a liquid trap to remove liquid from the gas-line. In one embodiment, the at least one accessory is a heat sink configured to cool the gas-line.

BRIEF DESCRIPTION OF THE DRAWINGS

FIG. 3 is a schematic isometric side view of a filter containing adsorbent according to one embodiment of the invention.

FIG. 4 is a schematic side view of the filter containing adsorbent according to the embodiment of FIG. 3.

FIG. 5 is a schematic front view of the filter containing adsorbent according to the embodiment of FIG. 3.

FIG. 14 is a table reflecting various color change indications with respect to adsorption according to various embodiments of the present invention.

FIG. 15 is a table reflecting experimental measurements in relation to a Test Lung-Square Function according to one embodiment of the present invention.

FIG. 16 is a table reflecting experimental measurements in relation to a Test Lung-Ramp Function according to one embodiment of the present invention.

FIG. 17 is a table reflecting experimental measurements in relation to a Human Trial according to one embodiment of the present invention.

FIG. 18 is a table reflecting experimental measurements in relation to a Humidifier according to one embodiment of the present invention.

FIG. 19 is a table reflecting experimental measurements in relation to a Drager Human Test according to one embodiment of the present invention.

FIG. 20 is a table reflecting experimental measurements in relation to a DMS Six-Hour Test according to one embodiment of the present invention.

DETAILED DESCRIPTION

Figure 1:
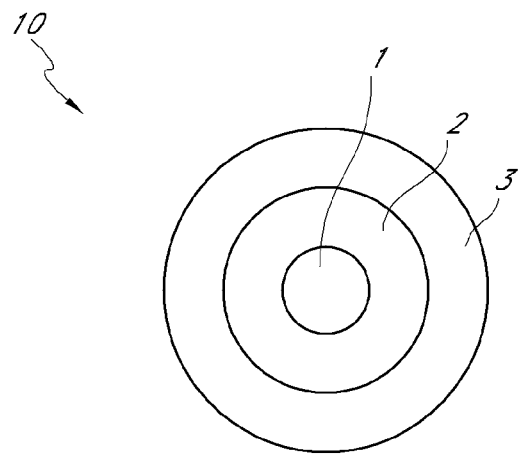
FIG. 1 is a schematic cross-sectional side view of one embodiment of adsorbent.

Several embodiments of the present invention relate generally to materials for facilitating the administration of DMSO and associated compounds. In some embodiments, these materials comprise adsorbents for the removal of the odors and compounds resulting from the metabolism or degradation of DMSO and associated compounds. In other embodiments, these materials comprise clean air members, masks, filters and fabrics that capture (absorb or adsorb) odors or compounds. In further embodiments, these materials comprise a clean air supply assembly for removing odors and compounds. In some embodiments, these materials comprise indicators to reveal the presence of these compounds. In some embodiments DMSO related odors are passed through a filter.

In several embodiments, the present invention provides compositions, pharmaceutical compositions and medicaments comprising DMSO, alone or in combination with one or more DMSO associated compounds (such as MSM) combined with one or more of the following: L-arginine, L-fructose 1, 6-diphosphate, L-lysine, L-aspartate, urea or a metabolite or derivative thereof.

The phrases "DMSO associated compounds", "associated compounds", or "related compounds" as used herein shall be given their ordinary meaning and shall include degradation compounds, derivatives, precursors, and metabolites of DMSO, such as methylsulfonylmethane (MSM or $DMSO_2$) and dimethyl sulfide or methylthiomethane (DMS). Metabolites include compounds to which DMSO is converted within the cells of a mammal. For example, the pharmaceutical compositions of several embodiments of the present invention may include a metabolite of DMSO instead of DMSO. The scope of the methods of several embodiments of the present invention includes those instances where DMSO is administered to the patient, yet the metabolite is the bioactive entity. In some embodiments, a filter removes odor from DMSO associated compounds (such as, in particular, DMS). In some embodiments, a filter allows odor reduction with application of DMSO associated compounds (such as DMSO and/or MSM). In some embodiments, a filter allows odor reduction with application of DMSO associated compounds (such as DMS).

The terms "pharmaceutical composition" or "formulation" as used herein shall be given their ordinary meaning, be used interchangeably, and shall include a mixture of the components listed herein, or a pharmaceutically acceptable salt, prodrug, ester or amide thereof, with other chemical components, such as diluents or carriers. The pharmaceutical composition may facilitate administration of the compound to an organism. Multiple techniques of administering a compound exist in the art including, but not limited to, oral, rectal, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" as used herein shall be given its ordinary meaning and shall include a compound that facilitates the incorporation of a compound into cells or tissues.

The term "treating" or "treatment" does not necessarily mean total cure. Any alleviation, amelioration, prevention, or reversal any undesired signs or symptoms of the disease to any extent or the slowing down of the progress of the disease can be considered treatment. Furthermore, treatment may include acts that may worsen the patient's overall feeling of well being or appearance. Treatment may also include lengthening the life of the patient, even if the symptoms are not alleviated, the disease conditions are not ameliorated, or the patient's overall feeling of well being is not improved.

DMSO Odor Reduction Systems And Methods

It is believed that when DMSO is administered to a mammal, roughly 15-20% of the DMSO is absorbed by the mammal's body and metabolized while roughly 80-85% of the DMSO is excreted. The most significant source of the unpleasant odor associated with the use of DMSO is caused by DMS, a metabolite of DMSO. Generally, when DMSO is given to a patient the human body metabolizes it into several different forms. It is believed that about 3% is converted into dimethyl sulfide (DMS), which is emitted through the both respiration of the patient (95%) and through the pores (5%) and has an overpowering, distinctively unpleasant odor. In several embodiments, use of DMSO is particularly effective for treating severe closed head injuries. Patients who have sustained such injuries are often incapable of regulating their own breathing, and are put on a ventilator until they recover sufficiently to be able to breathe for themselves. In one embodiment of a DMSO related odor reduction system, an activated carbon filter is fluidly attached to a ventilation or other breathing system, and in several embodiments, is particularly advantageous for DMSO treatment regimes for severe closed head injuries.

In one embodiment, DMSO related odors are reduced by passing the odor into contact with an adsorbent 10. In one embodiment, an adsorbent 10 includes, but is not limited to, activated carbon. In one embodiment, an adsorbent 10 is adapted for the partial or complete removal of the metabolites of DMSO and other compounds, and/or related odors. In one embodiment, an adsorbent 10 according to any one of the embodiments described herein captures (absorbs or adsorbs) DMS. In another embodiment, the adsorbent 10 captures MSM. In other embodiments, the adsorbent 10 captures all odor causing compounds related to DMSO. In one embodiment, absorbent 10 comprises one body. In other embodiments, absorbent 10 comprises two or more bodies. In one embodiment, adsorbent 10 comprises one layer. In some embodiments, the adsorbent 10 may comprise two or more layers. In one embodiment, at least one of the layers comprises core particles containing at least one adsorbing material. In one embodiment (an example of which is illustrated at FIG. 1), the adsorbent 10 comprises three layers: an inner layer 1; an optional intermediate layer 2, and an outer layer 3. In another embodiment, the adsorbent 10 may comprise one, two, or three of the layers. In other embodiments, additional layers are provided. Layers can be fixed or otherwise coupled to one another or to other materials (using, for example, adhesives, sealants, stitches, etc). Additional details associated with embodiments of adsorbents 10 are discussed below.

Figure 2:
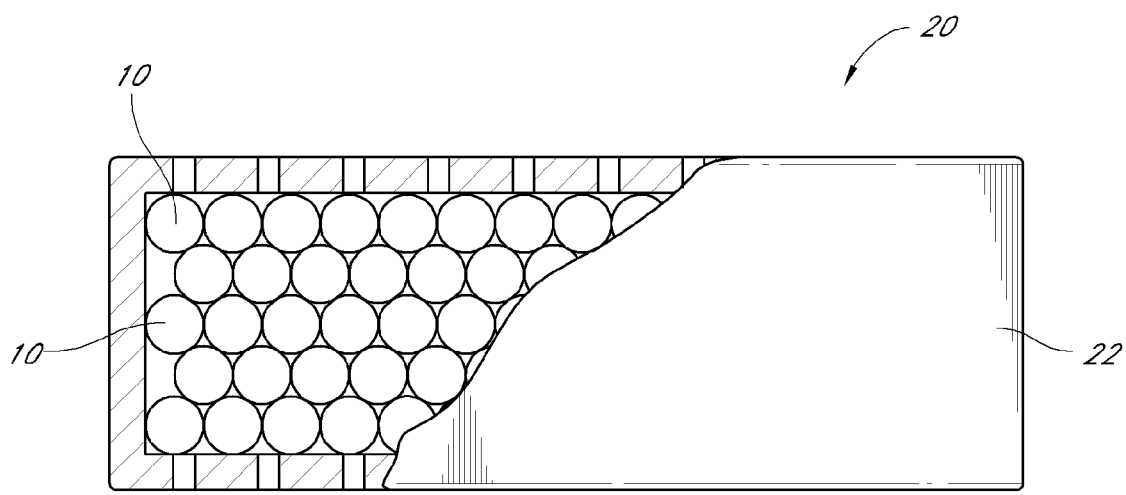
FIG. 2 is a schematic partial cross-sectional side view of a filter containing adsorbent according to one embodiment of the invention.

In one embodiment, DMSO related odors are reduced by passing the air containing said odor through a cartridge or filter containing the adsorbent 10. In one embodiment, as illustrated in FIG. 2, the invention comprises a filter 20 containing an embodiment of adsorbent 10. The size, scale, and shape of adsorbent 10 is not necessarily as illustrated in FIG. 2, and can be any variety of sizes, scales, or shapes. The filter 20, in some embodiments, functions as a holder for the adsorbent material. The adsorbent 10 may be incorporated into the filter for containment of the adsorbent material. In one embodiment, the adsorbent 10 is packed in filter 20. In one embodiment, the adsorbent 10 is loosely packed in filter 10. The filter 20 may be in the form of a rectangular, cylindrical or otherwise shaped vessel. The filter 20 may be provided in conjunction with a device for introducing air into said rectangular, cylindrical or otherwise shaped vessel, wherein the adsorbent 10 is partially or completely contacted when the air is introduced therein. Other shapes may also be used according to alternative embodiments of the invention.

In one embodiment, the filter 20 comprises an outer housing 22. In one embodiment, the housing 22 is plastic. In one embodiment, the housing 22 is elastic. In one embodiment, the housing 22 is rigid. In one embodiment, the housing 22 is flexible. In one embodiment, the filter 20 is configured to pass 120-180 l/min of air flow without a significant decrease (e.g., <10%, or <5% decrease) or significant loss of pressure (e.g. <10%, or <5%). In one embodiment, the filter 20 comprises a HEPA filter. In one embodiment, the filter 20 does not contain a HEPA filter. In several embodiments, a ventilation unit comprises one or more of the filters 20, at least one filter 20 and a HEPA filter, or at least one filter 20 and at least one non-carbon based filter.

In one embodiment, the adsorbent 10 is activated carbon. In one embodiment the activated carbon has a pore size equal to the size of a sulfur molecule for preferred bonding. In one embodiment, the pore size is about 0.01 μm to about 500 μm (e.g., about 0.1 μm-1 μm, 1 μm-10 μm, 10 μm-50 μm, 50 μm-100 μm, 100 μm-200 μm, 200 μm-300 μm, and 400 μm-500 μm). In one embodiment a small particle size increases rate of adsorption. In one embodiment, the adsorbent 10 is loosely packed activated carbon in granules. The carbon granules may be contained within the housing 22 in one or more locations. The carbon granules may be contained within the housing 22 on each end of the filter 20. In one embodiment, the adsorbent 10 is loosely packed activated carbon in a fabric mesh. The activated carbon according to several embodiments herein may be used to remove odorous compounds, acidic gases, and volatile organic compounds from a gas.

In one embodiment, the amount of activated carbon in the filter 20 is designed to capture all or a significant amount of the DMS (or DMSO or other DMSO associate compounds) emitted from one or more doses of DMSO (e.g., odors emanating from a patient's breath or pores). For example, for a 28% dosage of DMSO in 5% D5W of 200 ml, the amount of DMS removed is approximately 1.36 grams. In one embodiment, the amount of activated carbon used to remove DMS uses a ratio of 30 grams of carbon to 1 gram of DMS. In one embodiment, a ratio of 100 grams of carbon to 1 gram of DMS is used to include a safety margin or to be able to remove multiple DMSO doses at a time. In several embodiments, the ratio of the amount of carbon used to remove DMS (or DMSO or other DMSO associated compounds) to said DMS (or DMSO or other DMSO associate compounds) is about 5:1, 10:1, 20:1, 30:1, 50:1 or 100:1.

In various embodiments of the invention, one gram of activated carbon has a surface area greater than 500 $m^2$, greater than 1000 $m^2$, greater than 1500 $m^2$, or greater than 2500 $m^2$. In some embodiments, about 25-50 grams of activated carbon are used to remove at least 75% (e.g. at least 85%, or at least 95%) of all the odors associated with DMSO administration, particularly odors emanating with a patient's exhalation. This relatively small amount of carbon is surprisingly effective at removing the odor.

In one embodiment, a carbon filter according to several embodiments herein is able to reactivate after a certain period of time. For example, in one embodiment, the filter is able to capture a certain quantity of DMSO or associated compounds, and achieves a "saturation" point. In various embodiments, after a period of 12, 24, 36 or 48 hours, the same filter is capable of being reused. In some embodiments, the filter is reactivated (or recharged) using ambient light, sunlight or artificial UV light. In some embodiments, the filter is reactivated using heat.

In one embodiment, the invention comprises reducing DMSO related odor by passing it through a filter 20 containing an embodiment of adsorbent 10. In one embodiment, the invention comprises capturing the breath of the patient treated with DMSO upon exhalation and passing the breath containing the odor through a filter 20 containing an adsorbent 10. In one embodiment, the invention comprises capturing odor emanating from pores from the skin of a patient treated with DMSO with a filter 20 containing an adsorbent 10.

In one embodiment, illustrated at FIGS. 3-6, the invention comprises a filter 20 containing an embodiment of adsorbent 10. The embodiment of the filter 20 in FIGS. 3-6 can be similar to the embodiment of the filter 20 illustrated in FIG. 2. In one embodiment, the filter 20 comprises a housing 22 connectable to a cap 23. In one embodiment, the housing 22 has a housing port 21. In one embodiment, the cap 23 has a cap port 24. In various embodiments, the housing port 21 and/or the cap port 24 are configured to attach to tubing, ventilation tubes, luer connections, masks, pipes, or other mechanisms for directing or containing fluid and/or gas flow. In some embodiments, a fluid can be or relate to any gas or any liquid, and fluid communication or fluid connection can refer to the fluid being able to flow between points in fluid communication or fluid connection. In one embodiment, the housing port 21 is externally tapered. In one embodiment, the housing port 21 is internally tapered. In one embodiment, the cap port 24 is externally tapered. In one embodiment, the cap port 24 is internally tapered.

In various embodiments, the housing 22 and cap 23 are attachable with a mechanical connection, threading, snap-fit, unitary construction, bonding, ultrasonic welding, gluing adhesive, or other means for attaching bodies. In one embodiment, the housing 22 and cap 23 are configured to take a fluid or gas flow from the housing port 21, pass it through an adsorbent 10 contained in a chamber between the housing 22 and cap 23, and remove certain odors, and pass a reduced-amount of odor in the fluid or gas out through the cap port 24.

Figure 6A:
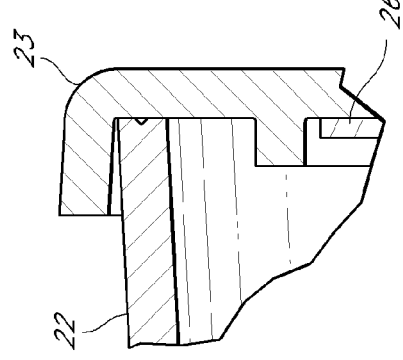
FIG. 6A is an enlarged schematic cross-sectional side view of a portion of the filter containing adsorbent according to the embodiment of FIG. 6.
Figure 6B:
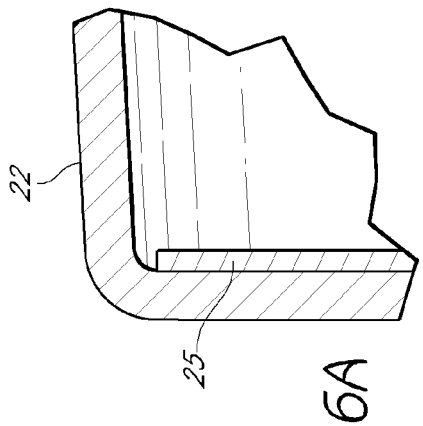
FIG. 6B is an enlarged schematic cross-sectional side view of a portion of the filter containing adsorbent according to the embodiment of FIG. 6.
Figure 6:
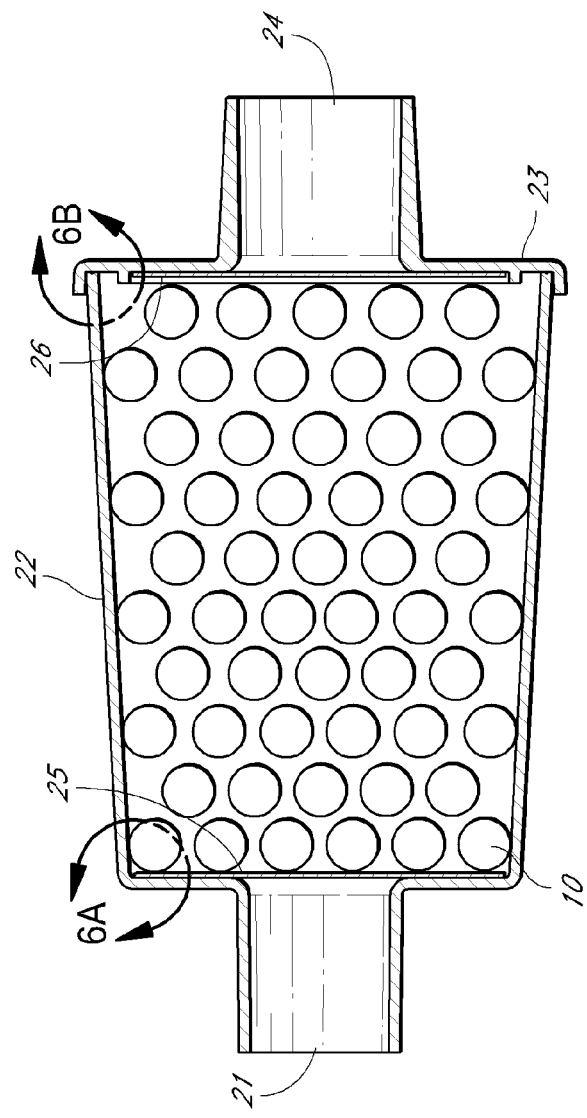
FIG. 6 is a schematic cross-sectional side view of the filter containing adsorbent according to the embodiment of FIG. 5.

In one embodiment, the housing 22 and cap 23 are configured to take a fluid or gas flow from the cap port 24, pass it through an adsorbent 10 contained in the housing 22 and cap 23, and remove certain odors, and pass a reduced-amount of odor in the fluid or gas out through the housing port 21. The size, scale, density, packing and shape of adsorbent 10 is not necessarily as illustrated in FIG. 6, and can be any variety of sizes, scales, densities, packing patterns or shapes.

In one embodiment, a housing sieve screen 25 is attachable to housing port 21 to allow a fluid or gas flow to pass through the housing port 21 while preventing larger particles from entering or exiting the housing port 21. In one embodiment, the housing sieve screen 25 prevents the adsorbent 10 from exiting the housing 22. In various embodiments, the housing sieve screen 25 is a mesh, fabric, porous material. In various embodiments, the housing sieve screen 25 can be attached to the housing port 21 with adhesive, hot melt, glue, or other fixing means.

In one embodiment, the housing sieve screen 25 is polyester based. In one embodiment, the housing sieve screen 25 is lofted material. In one embodiment, the housing sieve screen 25 has a tackifier (not illustrated) applied to at least one side. In various embodiments, a tackifier is an adhesive that can be applied in a spray or aerosol, or can be applied through contact, extrusion, printing process or other application techniques to place the adhesive on the sieve screen. In one embodiment the tackifier is uniformly placed on at least a portion of the sieve screen. In one embodiment the tackifier is non-uniformly placed on at least a portion of the sieve screen. In one embodiment the tackifier is placed on an entire side of a sieve screen. In one embodiment the tackifier is placed on a portion of the sieve screen configured to adhere the sieve screen to the housing port 21. In one embodiment, the housing sieve screen 25 is a polyester based lofted material with a tackifier applied to one side.

In one embodiment, a cap sieve screen 26 is attachable to cap port 24 to allow a fluid or gas flow to pass through the cap port 24 while preventing larger particles from entering or exiting the cap port 24. In one embodiment, the cap sieve screen 26 prevents the adsorbent 10 from exiting the cap 23. In various embodiments, the cap sieve screen 26 is a mesh, fabric, porous material. In various embodiments, the cap sieve screen 26 can be attached to the cap port 24 with adhesive, hot melt, glue, or other fixing means. In one embodiment, the cap sieve screen 26 is polyester based. In one embodiment, the cap sieve screen 26 is lofted material. In one embodiment, the cap sieve screen 26 has a tackifier applied to at least one side. In one embodiment, the cap sieve screen 26 is a polyester based lofted material with a tackifier applied to one side.

In one embodiment, the housing 22 is about 2.0-2.75 inches in diameter, has a chamber length of about 3.0-3.5 inches, and an overall length of about 3.0-5.0 inches including the housing port 21. In one embodiment, the cap 23 is about 2.0-3.0 inches in diameter and has a length of about 0.75-1.25 inches including the cap port 24. In one embodiment, the housing port 21 has an inner diameter of about 0.5 to 1.0 inches. In one embodiment, the housing port 21 has an outer diameter of about 0.5 to 1.0 inches. In one embodiment, the cap port 24 has an inner diameter of about 0.5 to 1.0 inches. In one embodiment, the cap port 24 has an outer diameter of about 0.5 to 1.5 inches.

In another embodiment, the housing 22 is about 2¼ inches in diameter, has a chamber length of roughly 3¼ inches, and an overall length of roughly 4 inches including the housing port 21. In one embodiment, the cap 23 is roughly 2½ inches in diameter and has a length of roughly 1 inch including the cap port 24. In one embodiment, the housing port 21 has in inner diameter of roughly ¾ of an inch. In one embodiment, the housing port 21 has in outer diameter of roughly 0.85 inches. In one embodiment, the cap port 24 has in inner diameter of roughly 0.88 inches. In one embodiment, the cap port 24 has in outer diameter of roughly 1 inch.

In yet another embodiment, the housing 22 is about 2.38 inches in diameter, has a chamber length of about 3.255 inches, and an overall length of about 4.19 inches including the housing port 21. In one embodiment, the cap 23 is about 2.523 inches in diameter and has a length of about 1.055 inch including the cap port 24. In one embodiment, the housing port 21 has in inner diameter of about 0.745 of an inch. In one embodiment, the housing port 21 has in outer diameter of about 0.865 inches. In one embodiment, the cap port 24 has in inner diameter of about 0.880 inches. In one embodiment, the cap port 24 has in outer diameter of about 1.000 inch.

As discussed in more detail below, one or more filters described herein can be used by canisters, masks or both. In one embodiment, the invention comprises a mask containing a thin layer of activated carbon mesh. In another embodiment, the invention comprises a canister having a battery powered fan pulling air away from the patient that then passes the air through an activated carbon mesh.

Several embodiments of the invention are particularly advantageous because DMSO metabolites and/or associated odors are removed by compact filters that are sized to fit ventilators, tubing, vents, and small spaces. Thus, in several embodiments, large fans, full room deodorizers, and/or chemical deodorizers are not needed. In some embodiments of the invention, the filters and other systems disclosed herein are used for capturing undesired odors and compounds other than those related to DMSO.

Adsorbents

In one embodiment, the invention comprises an adsorbent 10 adapted for the partial or complete removal of the metabolites of DMSO and other compounds, and/or related odors. In one embodiment, an adsorbent 10 according to any one of the embodiments described herein captures (absorbs or adsorbs) DMS. In another embodiment, the adsorbent 10 captures MSM. In other embodiments, the adsorbent 10 captures all odor causing compounds related to DMSO. In one embodiment, absorbent 10 comprises one body. In other embodiments, absorbent 10 comprises two or more bodies.

In one embodiment, adsorbent 10 comprises one layer. In some embodiments, the adsorbent 10 may comprise two or more layers. In one embodiment, at least one of the layers comprises core particles containing at least one adsorbing material. In one embodiment illustrated at FIG. 1, the adsorbent 10 comprises three layers: an inner layer 1; an optional intermediate layer 2, and an outer layer 3. In another embodiment, the adsorbent 10 may comprise any one, two, or three of the layers. In other embodiments, additional layers are provided. Layers can be fixed or otherwise coupled to one another or to other materials (using, for example, adhesives, sealants, stitches, bonding, weaving, etc).

In one embodiment, the adsorbent 10 comprises at least one porous coating layer including a polymer material that coats the core particles. In one embodiment, the intermediate layer of the adsorbent comprises the porous coating layer. In some embodiments, the inner or outer layer comprises the porous coating layer. In still additional embodiments, one or more of the layers of the adsorbent comprise the porous coating layer. The adsorbent 10 may comprise a metal compound and a water-soluble organic material disposed between the core particles and a porous coating layer. The water-soluble organic material is selected from the group consisting of one or more of the following: polymers of sugar, cellulose derivatives, alginic acid, methacrylic acid, acrylic acid, vinylpyrrolidone, vinyl alcohol, oxyolefins, and organic sulfur oxides such as $DMSO_2$ (dimethyl sulfone).

In one embodiment, the adsorbent 10 comprises a coating, such as a porous coating layer. In one embodiment, the coating layer may be formed by spraying and applying a suspension or a solution containing a polymer material over the adsorbing material, or by immersing the adsorbing material into the suspension or the solution. In one embodiment, the coating layer is formed on the outer layer of the adsorbent. In one embodiment, the coating layer is formed on the inner layer of the adsorbent. In one embodiment, the coating layer is formed on the intermediate layer of the adsorbent. In still additional embodiments, the coating layer is formed on one or more of the layers of the adsorbent.

In one embodiment, the adsorbent 10 comprises a material for adsorbing DMSO and associated compounds, and/or the odors related to same which comprises core particles. In one embodiment, the inner layer comprises core particles. The core particles may or may not represent the entire adsorbent material and may comprise one or more of the following: activated carbon, an inorganic oxide, a compound having ion exchange capacity, a modified compound thereof, an ion exchange resin, a chemical deodorizer, silica gel, alumina gel, zeolite, a molecular sieve, diatomaceous earth, inorganic oxide (e.g., copper oxide, iron oxide), chitosan, dextran sulfate, polyallylamine, sulfonated polystyrene resins, polyacrylic acid, polymethacrylic acid or a derivative thereof. Combinations of two or more of these compounds are used in some embodiments.

In one embodiment, the compound having ion exchange capacity is selected from the group consisting of one or more of the following: chitosan, dextran sulfate, polyallylamine, sulfonated polystyrene resins, polyacrylic acid, polymethacrylic acid and a derivative thereof.

In various embodiments, mechanisms of adsorption include chemical oxidation or reduction and/or mechanical entrapment. Thus, in some embodiments, the adsorbent 10 adsorbs odors or compounds by physically trapping, enclosing, or isolating said odors and compounds. In some embodiments, the adsorbent 10 comprises core particles, which adsorb odors or compounds by chemically oxidizing or reducing said odors and compounds. In some embodiments, undesired odors and compounds are reduced or eliminated because the core particles chemically react with said odors and compounds to render them inert or inactive.

In one embodiment, the core particles have an average particle size of about 0.01 mm to about 100 mm In one embodiment, the inner layer 1 has a thickness of about 0.1 μm to 1,000 μm. In one embodiment, the core particles are formed by a tableting process. In one embodiment, the core particles are coated. In one embodiment, the core particles have a porous coating layer having an average pore size of 0.001 μm to 50 μm. In another embodiment, the core particles are fixed on or otherwise coupled to a member having a one-dimensional structure or a two-dimensional structure. In one embodiment, the core particles are fixed onto the member having the two-dimensional structure at a density of about 0.1 to about 100,000 particles per 1 $cm^2$ of a surface of said member having the two-dimensional structure (e.g., about 0.1-10, 10-100, 100-1000, 1000-5000, 5000-10000, 10000-25000, 25000-50000, 50000-75000, or 75000-100000 particles per $cm^2$, or overlapping ranges thereof).

In one embodiment, the particles having said porous coating layer formed thereon are fixed on one surface of said member having the two-dimensional structure, and an adhesive is applied on another surface of said member having the two-dimensional structure.

In one embodiment, the particles having said porous coating layer formed thereon are fixed on a member having a three-dimensional structure. In various embodiments, the core particles are fixed onto said three-dimensional structure at a density of about 1 to about 1,000,000 particles per 1 $cm^3$ of a volume of said member having the three-dimensional structure (e.g., about 1-100, 100-1000, 1000-5000, 5000-10000, 10000-25000, 25000-50000, 50000-75000, 75000-100000, 100000-500000, or 500000-1000000 particles per $cm^3$, or overlapping ranges thereof).

In one embodiment, the core particles having said porous coating layer formed thereon are fixed to a member in a state of a layer having a thickness of a single particle to about 1,000 particles (about 1-10, 10-50, 50-100, 100-250, 250-500, or 500-1000 particles, or overlapping ranges thereof). In certain embodiments relating to use as a visual indicator, greater density may provide greater adsorbency but lesser sensitivity, and lower density may give inadequate visual indication at some point.

In one embodiment, the core particles having said porous coating layer formed thereon are fixed to the member with an adhesive. The adhesive may comprise an organic solvent type adhesive, a water type adhesive, a hot melt type adhesive, or combinations thereof. The member may comprise a portion covered by an air permeable sheet. The member may be entirely wrapped with an air permeable sheet. The member may be contained in an air permeable container. The air permeable container may comprise an unwoven cloth, a woven cloth, a mesh, a net, or combinations thereof.

In one embodiment, the core particles having said porous coating layer formed thereon are wrapped with an air permeable sheet. In one embodiment, the core particles having said porous coating layer formed thereon are contained in the air permeable sheet in a number of about 1 to about 100,000,000 particles (e.g., about 1-100, 100-1000, 1000-5000, 5000-10000, 10000-25000, 25000-50000, 50000-75000, 75000-100000, 100000-500000, or 500000-1000000, 1000000-10,000,000, or 10,000,000-100,000,000 particles, or overlapping ranges thereof). In certain embodiments, greater density may provide greater adsorbency but lesser sensitivity, and lower density may give inadequate visual indication. In certain embodiments relating to use of the core particles as an indicator, greater size may provide greater adsorbency but lesser sensitivity, and smaller size may give inadequate visual indication at some point.

In several embodiments, a material for adsorbing DMSO and associated compounds, and/or the odors related to same comprises an intermediate layer, which, in some embodiments, comprises a porous coating. The intermediate layer of the adsorbent may comprise one or more of the following: the oxide, hydroxide, carbonate, sulfates, phosphate, metasilicate, borate, oxalate, tungstate, molybdate, vanadate, chromate, selenate, and manganate of a metal or the metal itself. The metal may also include titanium, zirconium, silicon, zinc, iron, manganese, aluminum, magnesium, nickel, copper, silver, barium, calcium, scandium, bismuth, molybdenum, niobium, neodymium, antimony, selenium, stannum, strontium, terbium, tellurium, thorium, and yttrium.

In another embodiment, the metal compound has a particulate shape having an average particle size of about 0.001 μm to about 50 μm Other shapes and sizes may be used.

In one embodiment, the intermediate layer has a thickness of about 1 μm to about 10,000 μm. In one embodiment, the greater number lending toward more adsorbency but less efficiency of coating use while the lower number contributes to high efficiency of coating use but lower volumetric adsorbency. In certain embodiments, too thin a coating may result in poor indication due to lack of color, and too thick a coating may result in too much adsorption and loss of sensitivity.

In several embodiments, a material for adsorbing DMSO and associated compounds, and/or the odors related to same comprises a porous coating layer. In some embodiments, the outer layer of the adsorbent comprises a porous coating layer. The porous coating layer may comprise one or more of the following: a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin and a copolymer thereof, and a derivative thereof or polytetrafluoroethylene, polyhexafluoropropylene, polydifluoroethylene, polyvinyliden fluoride, polyvinyl fluoride, and a copolymer or derivative thereof. Combinations of two or more of these materials are used in some embodiments.

In one embodiment, the porous coating layer has a thickness of about 0.01 µm to about 1,000 µm (e.g., about 0.01-1, 1-10, 10-50, 50-100, 100-250, 250-500, or 500-1000 µm, or overlapping ranges thereof). In one embodiment, the greater number lending toward more adsorbency but less efficiency of coating use while the lower number contributes to high efficiency of coating use but lower volumetric adsorbency.

In some embodiments, the porous coating layer has an average pore diameter of about 0.01 µm to about 500 µm (e.g., about 0.01-1, 1-10, 10-50, 50-100, 100-250, or 250-500 µm, or overlapping ranges thereof) and/or has a porosity of about 3% to about 90% (e.g., about 3-15%, 15-30%, 30%-60% or 60-90%, or overlapping ranges thereof). In one embodiment, the porous coating layer is colored.

In one embodiment, a method for producing the adsorbent, or indicating adsorbent, is provided. In an embodiment, the method comprises forming the coating layer by applying a liquid containing said polymer material onto a surface of said core particles. The coating layer may be formed by spraying said liquid over said core particles and/or immersing said core particles into said liquid. In one embodiment, the liquid comprises a suspension of said polymer material and/or a solution of said polymer material.

In one embodiment, during said step of forming the coating layer or after said step of forming the coating layer, at least one of a step of heating and a step of decreasing a pressure is carried out to draw said porous coating layer.

In one embodiment, during said step of forming the coating layer or after said step of forming the coating layer, a heating process is carried out so that said coating layer partially shrinks and partially expands.

In one embodiment, the core particles in said step of forming the coating layer are in a water-containing state, in an oil-containing state, or in a frozen state thereof.

In one embodiment, the liquid comprises a pore-forming agent. The pore-forming agent may comprise a water-soluble polymer or oligomer. The water-soluble polymer or oligomer may be selected from the group consisting of one or more of the following: cellulose, poly(oxyolefin), polyvinylpyrrolidone, polyvinyl alcohol, a saponification compound of polyvinyl acetate, polyacrylic acid, polymethacrylic acid, and derivatives thereof. In another embodiment, the water-soluble polymer or oligomer is selected from the group consisting of one or more of the following: methyl cellulose, hydroxymethyl cellulose, hydroxyethyl cellulose, hydroxypropyl cellulose, polyvinylpyrrolidone, polyvinyl alcohol, polyethylene glycol, polypropylene glycol, and derivative thereof.

In one embodiment, the pore-forming agent comprises an oil soluble polymer or oligomer. The oil soluble polymer may comprise liquid paraffin.

In one embodiment, the pore-forming agent is removed during or after the step of forming said coating layer. In another embodiment, the pore-forming agent is removed by one or more of the following processes: extraction, evaporation, sublimation or combustion.

In some embodiments, a packed bed containing the adsorbent as disclosed herein is provided. The packed bed, in some embodiments, functions as a holder for the adsorbent material. The packed bed of adsorbent may be incorporated into a cartridge for containment of the adsorbent material. The cartridge may be in the form of a rectangular, cylindrical or otherwise shaped vessel. The cartridge may be provided in conjunction with a device for introducing air into said rectangular, cylindrical or otherwise shaped vessel, wherein the adsorbent is partially or completely contacted when the air is introduced therein. One of skill in the art will understand that other shapes may also be used according to additional embodiments of the invention.

Masks

In one embodiment, the invention comprises a mask 30 that is designed to reduce, eliminate or shield the user from odors associated with DMSO and related compounds. Embodiments described below that relate to various embodiments of fabrics may be used to construct some embodiments of the mask. See the Fabrics section, below.

Figure 7:
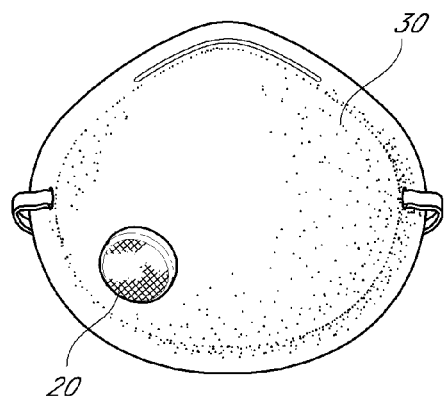
FIG. 7 is a schematic front view of a mask with a filter according to one embodiment of the invention.
Figure 8:
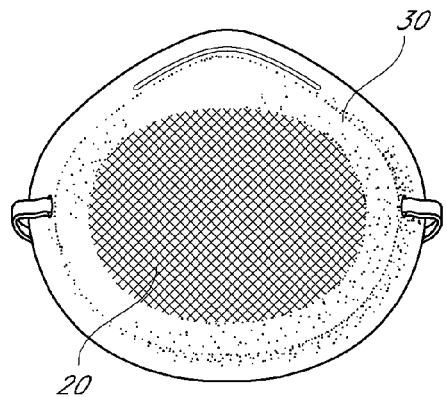
FIG. 8 is a schematic front view of a mask with a mesh filter according to one embodiment of the invention.

FIG. 7 illustrates one embodiment of a mask 30 with a filter 20 in fluid communication with the inside of the mask 30. In one embodiment, the odor is captured in a mask 30 with a filter 20 in fluid communication with the outside of the mask 30. FIG. 8 illustrates one embodiment of a mask 30 comprising a mesh filter 20 integrated into the mask. In another embodiment illustrated at FIG. 9, the odor is captured by a mask 30, passed through a hose 35 to the filter 20. In one embodiment, the mask 30 is an oxygen mask. In one embodiment illustrated at FIG. 10, the mask 30 is attached to a ventilator 40. In various embodiments, a ventilator 40 can be exchanged with a powered gas extraction device, a breathing system, a gas exchange device, an exchange oxygenator, an oxygen system, a system in fluid communication with an air or oxygen exhaust system, or a wall air system. The output of the filter 20 can be attached to any gas collection vessel, to the oxygen container or to the outside. In one embodiment, the filter 20 is located within the ventilator 40. In one embodiment, the filter 20 is external to the ventilator and located near or in line with the mask tube.

In some embodiments, the filter 20 can be used in fluid communication with a ventilator 40 to help remove or reduce the odor associated with the flow of a fluid, such as air or the breath from a subject. In some embodiments, accessories can be used in fluid communication with the filter 20 and/or the ventilator 40 to assist in the comfort or treatment of a subject. Some subjects receiving therapeutic treatments are in a weakened state and may need the air they breathe cleaned to remove germs or viruses, or could need heating of the air, or could need moisture or humidification of the air, or other modifications to the air. In some embodiments, accessories can be used to modify the air that is breathed by a subject. In one embodiment, a contaminant filter can be used as an accessory to help reduce particles or contaminant in the air flow to and/or from a subject. In one embodiment, a bio-filter can be used as an accessory to help reduce germs or viruses in the air flow to and/or from a subject. In one embodiment, a HEPA filter can be used as an accessory, such as a contaminant filter and/or as a bio-filter.

In one embodiment, a heating element can be used as an accessory to warm the air flow to and/or from a subject. In one embodiment, a cooling element or heat sink can be used as an accessory to help reduce the temperature of the air flow to and/or from a subject. In various embodiments, accessories can include an electrical heating element, a radiator, air conditioning, cooling coils, a flow meter, sensors, and other devices for monitoring or altering the air or fluid. In one embodiment, a humidifier can be used as an accessory to add, remove or modify moisture in the air flow to and/or from a subject. In one embodiment, a water trap can be used as an accessory to remove or modify moisture in the air flow to and/or from a subject.

In one embodiment, the odor is captured from an endotracheal tube by a hose 35 that is attached to a filter 20. In one embodiment, the odor is captured from an endotracheal tube by a hose 35 that is attached on its proximal end to a filter 20 and a ventilator 40. In one embodiment, the filter 20 can be placed in any one or more positions or configurations with respect to any accessories or components. For example, in one embodiment, an odor-source can be fluidly connected to an accessory, and distal to the accessory along the fluid connection line or tube, a filter 20 can be placed downstream of the accessory. In an embodiment, a filter 20 is placed downstream of one or more accessories or components. In some embodiments, the filter 20 can be placed upstream of one or more accessories. In one embodiment, a filter 20 can be placed in any location (upstream or downstream) with respect to a ventilator 40, while the filter 20 is placed downstream of other accessories. In one embodiment, the filter 20 is placed after (or downstream of) a contaminant or bio-filter with respect to an odor-source. In various embodiments, the contaminant or bio-filter can be a HEPA filter, and the odor-source can be a subject or a patient. In one embodiment, the filter 20 is placed after (or downstream of) a water trap. In one embodiment, the filter 20 is placed between an exhalation hose 35 and a ventilator 40. In one embodiment, placement of the filter 20 includes disconnecting exhalation hose 35, attaching the filter 20 to the exhalation hose 35, and connecting the filter 20 to the ventilator 40. In one embodiment, placement of the filter 20 includes disconnecting exhalation hose 35, attaching a male end of filter 20 to the exhalation hose 35, and connecting a female end of filter 20 to the ventilator 40. In one embodiment, the filter 20 can be placed at the exhaust port of the ventilator 40. In one embodiment, placement of the filter 20 includes disconnecting the exhalation hose 35, attaching the filter 20 to the exhaust port and attaching the filter 20 to tubing. In one embodiment, placement of the filter 20 includes disconnecting the exhalation hose 35, attaching a male end of 6" tubing to the exhaust port and attaching the male end of filter 20 to the 6" tubing. In one embodiment, the filter 20 can be replaced every 6 hours just prior to initiation of new intravenous therapy.

Figure 11A:
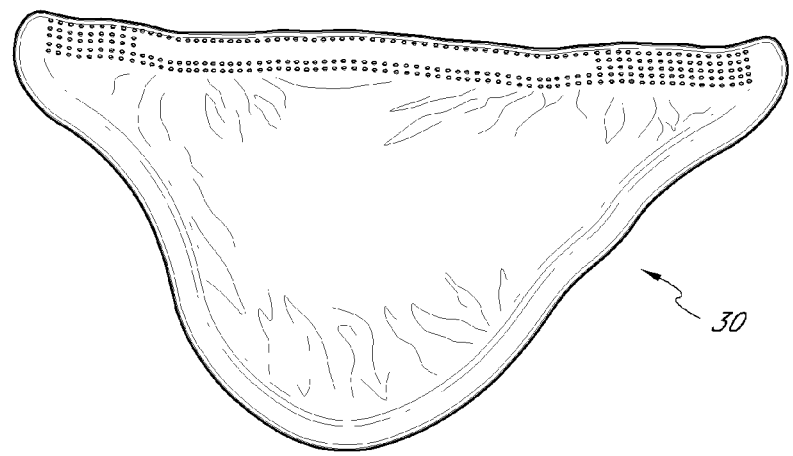
FIG. 11A shows a schematic front view of a "duckbill" type odor-absorbing mask according to one embodiment.
Figure 11B:
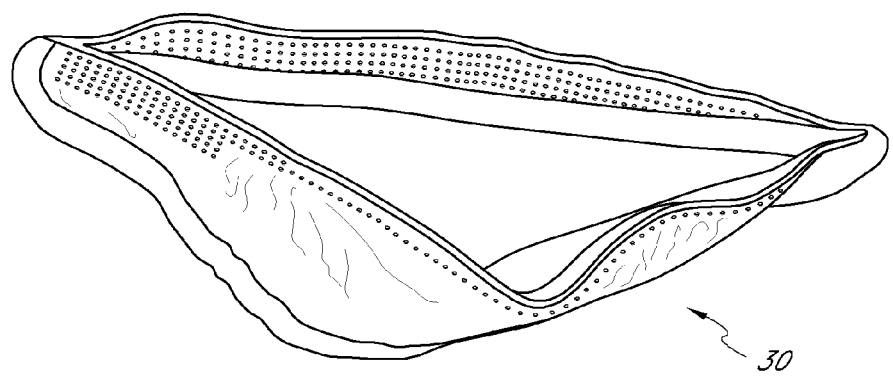
FIG. 11B shows a schematic front view of a "duckbill" type mask according to one embodiment, showing the mask partially open.
Figure 12:
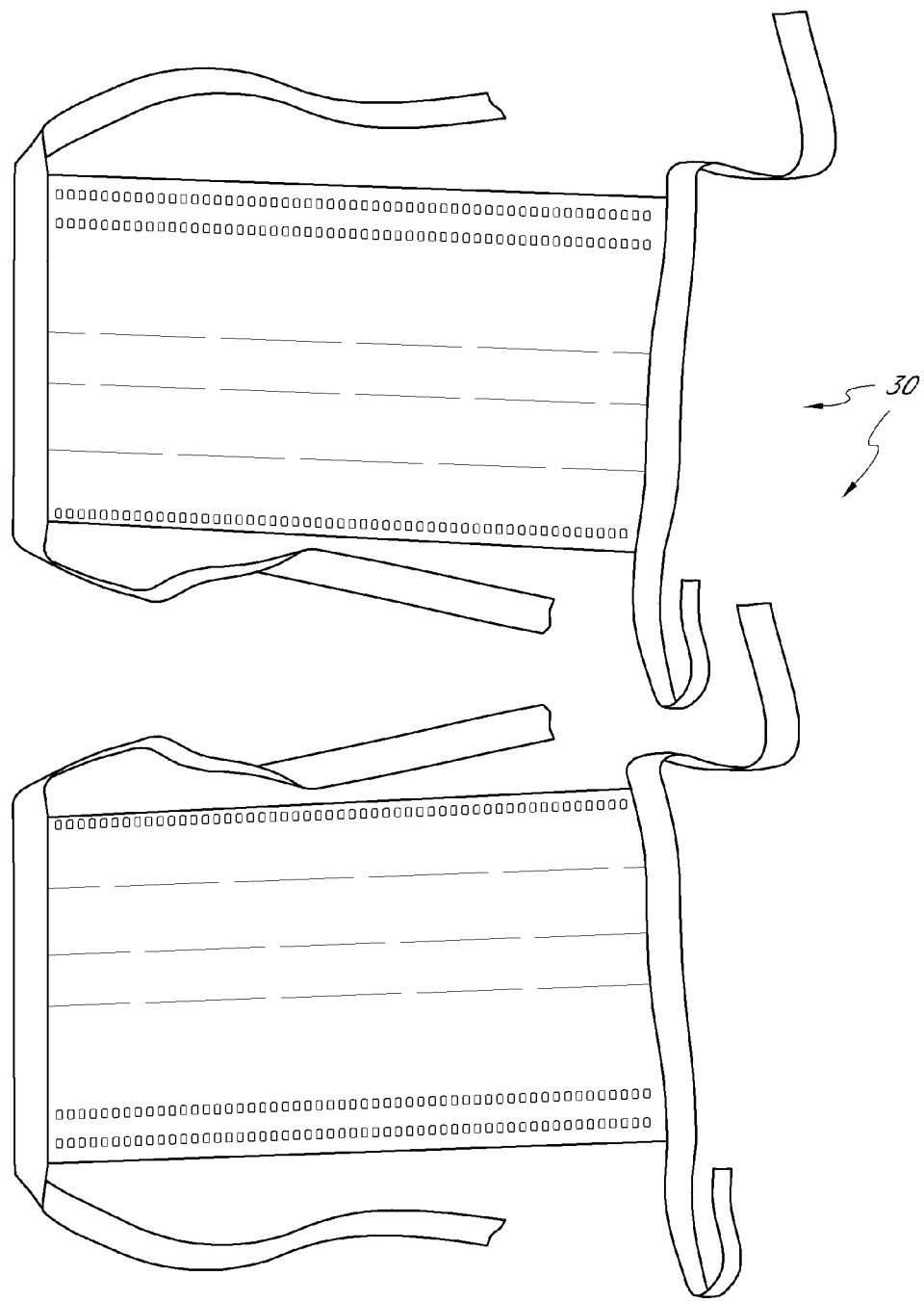
FIG. 12 shows a schematic surgical mask according to one embodiment.

In one embodiment, the mask 30 comprises one or more layers. However, in many embodiments, the mask contains only a single layer of activated carbon. The face mask may be a "duckbill" type mask 31 (FIGS. 11A, 11B), or surgical mask 32 (FIG. 12). In one embodiment, an exhale valve comprising two flat strips of elastomer is installed in place of the entire seam at the bottom of the duckbill mask which has a large cross-sectional area when open. In one embodiment, a surgical mask 30 may also comprise one or more odor-masking "scratch and sniff" patches which release one or more pleasant odors when abraded. Such odors include lemon, perfume, peppermint, vanilla and the like. Various embodiments of patches may be square, circular rectangular or any other desired shape.

In one embodiment, the mask layers include from outer (distal to the face) to inner (proximal to the face): 1) outer shield; 2) copper layer; 3) carbon layer; 4) chemical layer; and 5) facial layer. In another embodiment, the mask comprises one or more of these layers. The layers need not be present in the order identified above. In several embodiments, the mask contains only an activated carbon layer for odor capture.

The outer shield may provide N95 or N99 filtration. In one embodiment, the mask filters at least about 75%, 80%, 85%, 90%, 95%, 97%, 99%, 99.9%, or 100% of airborne particles. The outer shield layer may comprise 100% synthetic fiber. Examples of synthetic fibers include those described herein, and other synthetic fibers well known in the art (e.g., polyester, rayon, acrylic, nylon, dacron).

The copper layer may act as a catalytic converter. The copper layer may comprise one or more fibers and powdered copper. In one embodiment, the fiber comprises about 40% wood pulp and about 60% synthetic fiber. The powdered copper may be present on the fiber in an amount ranging from about 100% w/w to about 500% w/w, e.g., from about 200% w/w to about 400% w/w or about 250% w/w.

The carbon layer may comprise activated carbon (charcoal) and act as an odor adsorber. In one embodiment, the carbon layer comprises two sub-layers: activated charcoal adsorber I and activated charcoal adsorber II. The carbon layer may comprise one or more fibers and activated carbon. In one embodiment, the fiber comprises about 40% wood pulp and about 60% synthetic fiber. The activated carbon may be present on the fiber in an amount ranging from about 100% w/w to about 500% w/w, e.g., about 200% w/w to about 400% w/w or about 250% w/w. One or more types of activated carbon may be incorporated into the carbon layer. In one embodiment, the following Chemsorb activated carbon compositions are used: 1202-70 G12 (for acid gases), 620-70 G12 (for ammonia and amines), 1505-70 G12 (for aldehydes) and 1000-70 (for organic vapors).

The chemical layer may allow breath-activated odor removal in one embodiment. In one embodiment, the chemical layer comprises one or more fibers and one or more odor-removing chemicals, which may be breath-activated, such as citric acid, chitosan, MSM and other compounds. In one embodiment, the chitosan, citric acid and MSM may be present on the fiber in amounts of about 50% w/w, about 40% w/w and about 30% w/w, with the remainder being one or more other compounds.

The facial layer may provide soft facial protection in one embodiment. The facial layer may comprise 100% synthetic fiber. In one embodiment, natural fibers are used, alone or in combination with synthetic fibers.

In one embodiment, the mask is made by placing the coatings on separate layers prior to forming the masks on the same multi-sheet airlay machine.

Some DMSO related odor is released in the breath, and some is produced through the pores of the skin. This odor can be removed or reduced by filters, masks, fabrics, air treatment canisters or any combination of devices or methods.

Clean Air Members

In one embodiment of the invention, a device and method for cleaning air comprising contacting air with an indoor ambient air cleaning member (such as a cartridge or an embodiment of a filter 20). In one embodiment, the clean air member comprises an embodiment of adsorbent 10 (e.g., activated carbon) as described above. In one embodiment, the clean air member adsorbs DMSO and/or DMSO related compounds, and/or odors associated with the adsorbent 10. In some embodiments, the clean air member additionally removes one or more undesired compounds from the air that are unrelated to DMSO (e.g., toxic fumes or gases).

In one embodiment, the clean air member (such as a cartridge or filter) comprises an inner layer, an intermediate layer, and an outer layer, as described above.

The clean air member may be contained in a rectangular, cylindrical or otherwise shaped vessel, and said indoor ambient air cleaning member is freely convected when the air is introduced therein. The vessel may be tilted.

In several embodiments of the invention, the clean air member according to any one of the embodiments described herein is an ambiance odor or sulfur chemical regulating member.

In one embodiment, the clean air member (such as a cartridge or filter) comprises core particles comprising at least one odor or sulfur chemical regulating material of an acid or acid salt, and a porous coating layer including a polymer material that coats the core particles. In one embodiment, the acid is selected from the group consisting of one or more of the following: lactic acid, malic acid, tartaric acid, oxalic acid, chromic acid, dichromic acid, manganic acid, permanganic acid, thiocyanic acid, cyanic acid, carbonic acid, hydrochloric acid, perchloric acid, chloric acid, chlorous acid, hypochlorous acid, hydriodic acid, periodic acid, iodic acid, iodous acid, hypoiodous acid, sulfuric acid, sulfurous acid, nitric acid, nitrous acid, and phosphoric acid.

In one embodiment, the clean air member comprises an odor or sulfur chemical regulating material selected from the group consisting of one or more of the following: sodium sulfate, an alkali metal salt of phosphoric acid, an alkali metal salt of hydrogenphosphate, an ammonium salt of phosphoric acid, and an ammonium salt of hydrogen phosphate.

In one embodiment, the clean air member comprises core particles that comprises a hydrophilic polymer compound. The hydrophilic polymer compound may be selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the clean air member comprises core particles that have an average particle size of about 0.01 mm to about 100 mm (e.g., about 0.01 mm to about 1 mm, about 1 mm to about 10 mm, about 10 mm to about 25 mm, about 25 mm to about 50 mm, about 50 mm to about 75 mm, about 75 mm to about 100 mm, and overlapping ranges thereof).

In one embodiment, the clean air member comprises core particles comprising at least one odor or sulfur chemical regulating material of an acid salt, and a porous coating layer comprising a polymer material that coats said core particles is provided. The acid salt may be selected from the group consisting of one or more of the following: an alkali metal salt, an alkaline earth metal salt, and an ammonium salt.

In one embodiment, the core particles further comprises a hydrophilic polymer compound. The hydrophilic polymer compound may be selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the clean air member comprises a porous coating layer having a thickness of about 0.1 µm to about 1,000 µm and/or average pore size of about 0.001 µm to about 50 µm. The porous coating layer of the clean air member may comprise a silver deposit layer.

In one embodiment, the clean air member comprises a porous coating layer that comprises material selected from the group consisting of one or more of the following: a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin, copolymers thereof, and derivative thereof. The porous coating layer may be colored.

In a further embodiment, an adsorbent for removal of respiratory exhalation from a patient treated with DMSO is provided. In yet another embodiment, an adsorbent for removal of DMSO metabolites from a respiratory ventilator or an isolation room ventilator is provided. The adsorbent may be part of the clean air member.

In one embodiment, the clean air member comprises an oxidizing agent. The oxidizing agent is selected from the group consisting of one or more of the following: a mixture of ascorbic acid and an iron-containing compound, permanganates, manganese dioxide, chromates, dichromates, osmium tetraoxide, ruthenium tetraoxide, silver oxide and palladium chloride. In one embodiment, the iron-containing compound is selected from the group consisting of one or more of the following: iron chloride, iron bromide, iron iodide, iron oxide, iron perchlorate, iron thiocyanate, iron sulfate, iron sulfide, iron acetate, iron oxalate, Mohr's salt, di-iron monophosphide and tri-iron monophosphide.

In one embodiment, the clean air member comprises, a canister, a fan configured to pull air away from the patient, and a filter 20. In one embodiment, the clean air member comprises, a canister, a fan configured to pull air away from the patient, and a mesh. In one embodiment, the mesh comprises an activated carbon mesh. In one embodiment, the canister can exchange the air in the average hospital room in 15 minutes. In one embodiment, two canisters can be placed in a room to exchange the room air in 7.5 minutes. In various embodiments, other exchange and flow rates are possible.

Clean Air Supply Assembly

In one embodiment, the invention comprises a system for removing odors and chemicals resulting from the treatment of patients with DMSO and related compounds. In one embodiment, this system is a clean air supply assembly comprising one or more of the activated carbon filters described herein.

In one embodiment, the invention comprises a rollably positionable, adjustably directable clean air supply assembly and enclosure for use in DMSO treated medical patient environments. The clean air supply assembly provides, in some embodiments, localized clean air free of the odors, DMS (dimethyl sulfide) and compounds resulting from the metabolism of DMSO and DMSO associated compounds including, but not limited to, hydrogen sulfide and methyl mercaptan.

In one embodiment, the clean air supply assembly comprises a fully portable device providing for the effective capture and movement of room air through an adsorbent material suitable for the complete removal of the metabolites of DMSO and other related compounds. This device may have battery power for backup or for use while moving a patient. In one embodiment, the device is capable of turning any hospital room into a virtual clean room.

In another embodiment of the present invention, a portable curtaining containment system which may encompass the patient's upper torso or the entire patient bed area with provisions for caregiver access is provided.

In one embodiment, the invention comprises a rollably positioned, passable through doorways, adjustably directable clean air supply assembly which provides air free of the metabolites of DMSO and others for use in an area where a patient is being treated using DMSO and associated compounds. The clean air supply assembly may comprise one or more of a base module, a powered air moving assembly and a filtration system.

Figure 9:
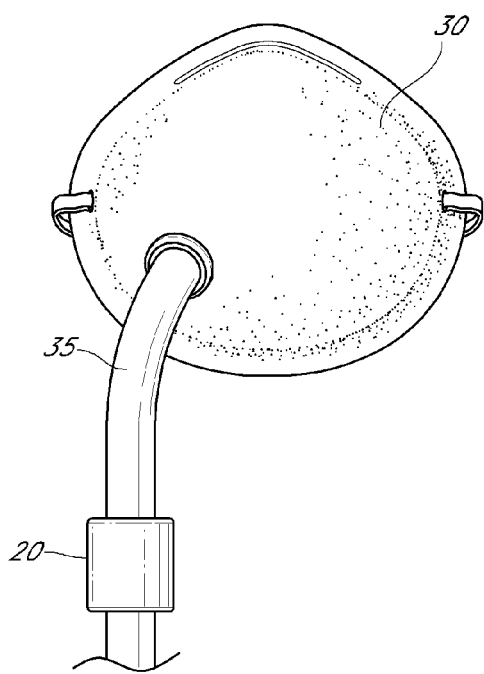
FIG. 9 is a schematic front view of a mask with a hose and a filter according to one embodiment of the invention.
Figure 10:
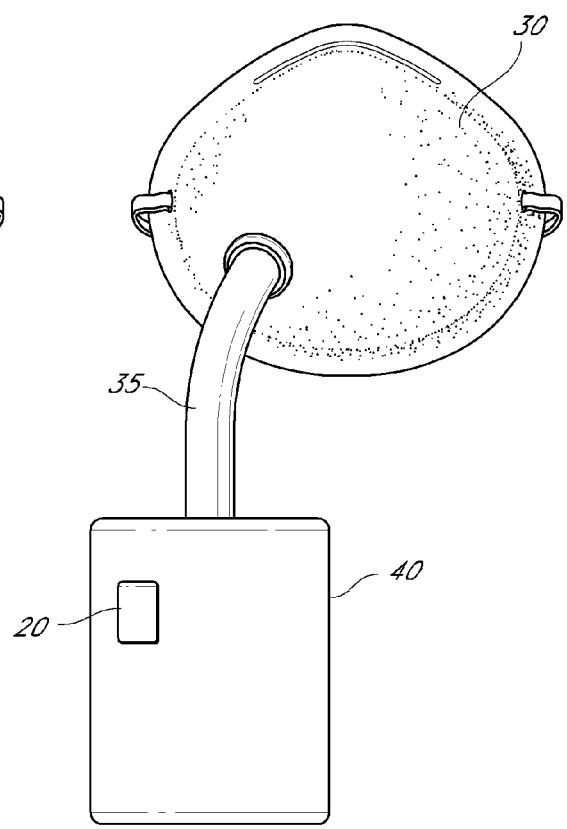
FIG. 10 is a schematic front view of a mask with a hose, ventilator and a filter according to one embodiment of the invention.

One embodiment of a clean air supply assembly 4 is shown schematically in FIG. 9 and comprises a rollable support assembly 19 having wheels 21. Attached to the platform are a power supply unit 5 powering an electronics package 7 providing either DC or AC power depending on the motor selected. In one embodiment, the power supply unit 5 comprises a battery with a charger. An internal or external chemical and/or odor filter and adsorbent cartridge 9 containing an adsorbent 10 is mounted on platform 19 adjacent power supply unit 5 and electronics package 7.

In one embodiment, the adsorbent cartridge 9 follows the air moving assembly and is capable of removing metabolites of DMSO and other related compounds, and may incorporate visual indication of depletion of such metabolites. The adsorbent may be augmented or replaced by ultraviolet lamps and/or ozone (e.g., ozone injection) to further or fully remove odors, DMS, methyl mercaptan and/or hydrogen sulfide and other chemicals.

In one embodiment, clean air supply assembly 4 directs a controlled amount of clean grade air through an adjustably oriented top hood assembly 11 which contains a pre-filter 13 and a sealed final filter 15 (e.g., high efficiency particle arrestor (HEPA) filter) which may be mounted within the lower portion of the base 14 or within the top final filter hood assembly 11. This final filter 15 filters the air and allows the discharge of the air at minimal-eddy creating air velocities for improved air quality levels, which creates certifiable cleanrooms, clean zones, improved recirculated air quality within an given area, where a patient is being treated with DMSO. The clean air supply assembly 4 is shown optionally attached to a patient isolation unit 17.

Figure 13:
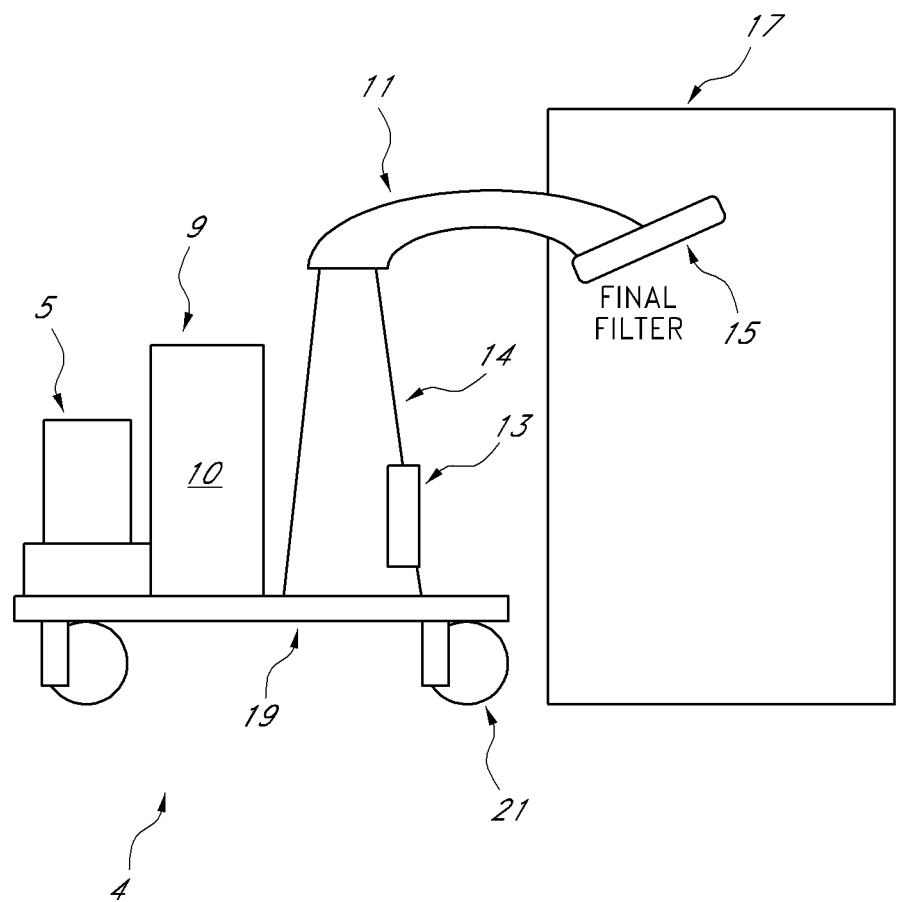
FIG. 13 is a schematic diagram of a rollably positionable, adjustably directable clean air delivery supply assembly and enclosure according to one embodiment.

In one embodiment, the clean air supply assembly is a modification of the clean air supply assembly shown in FIG. 2 of U.S. Pat. No. 6,099,607, the entire contents of which are incorporated herein by reference. In this device, the rollable support assembly in U.S. Pat. No. 6,099,607 is extended in a direction opposite the hood top assembly 328, and the battery/power module/adsorbent cartridge assembly shown in FIG. 13 of the present application is placed on, or attached to, the rollable support assembly. This device may be attached to a wheelchair or gurney via a wheelchair/gurney attachment, and filters odors and chemicals resulting from DMSO treatment of a patient.

The clean air supply assembly according to one embodiment of the present invention may also be attached to a patient isolation unit comprising a frame body foldable and/or capable of being disassembled; and a flexible envelope adapted to be detachably attached to the frame body as assembled as described in U.S. Pat. No. 6,099,607. The patient isolation unit may also comprise a collapsible framework constructed of rods pivotally joined at their ends to hubs to form a self-standing unit when expanded and to fold into a small set of nearly parallel rods when folded as described in U.S. Pat. Nos. 4,986,016 and 5,125,205, the entire contents of which are incorporated herein by reference.

In another embodiment, the exhauster device 5 shown in FIG. 1 of U.S. Pat. No. 6,966,937, herein incorporated by reference, is modified by extending the rollable support assembly in a direction opposite exhaust duct 4 and the battery/power module/adsorbent cartridge assembly shown in FIG. 13 of the present application is placed on, or attached to, the rollable support assembly. The device may then be attached to a patient isolation unit to filter odors and chemicals resulting from DMSO treatment of a patient.

The patient isolation unit may include an integral patient isolation curtain rod, or a separate foldable frame body, and a flexible envelope made of a natural or polymeric porous or nonporous film, knit, woven or non-woven sheet which can be attached to the assembled frame body, which may or may not include a bottom.

In one embodiment, the patient isolation assembly includes a low cost disposable curtain to be affixed to the patient privacy curtain, or to an inexpensive plastic frame.

Fabrics

In several embodiments of the present invention, a fabric that reduces or eliminates the odor of DMSO and associated compounds is provided. In several embodiments, the fabric comprises at least one layer of activated carbon, which may or may not be encompassed in a mesh enclosure. In one embodiment, the fabric comprises odor adsorbing woven or non-woven fabric suitable for the manufacture of masks, gloves, socks, clothing, bedding and other protective items capable of the partial or complete capture of the metabolites of DMSO and others. Adsorption may include chemical oxidation, reduction, physical entrapment in fissures, or other means. The adsorbent fabric may include adsorbent fibers or fibers coated with an adsorbent or it may be layered with adsorbent material between the layers. Finally, the fabric may incorporate any or all of these modes of odor capture simultaneously.

In one embodiment, the fabric comprises a three dimensional web. In one embodiment, the basic fiber support structure of the three dimensional web comprises woven or nonwoven web of the fibers of polyethylene, polypropylene, polyvinyl chloride, polyurethane, polyamide, nylon, polyacrilan, rayon, silk, ramey, cellulosic material and any other suitable fibrous material or material which may be made fibrous. Intermediate layers may comprise knit or randomly formed copper, aluminum, iron, glass, carbon, or other inorganic fibers. Each layer may be formed on a knitting, weaving, moving web, fluid dispersion, or other device. Layers may be combined following the forming of each or one or more layers may be formed as they are layered. Layers may be adhered together by crosslinking, hot melt stitching, sewing, gluing, or other methods well known in the art.

In one embodiment, the odor adsorbing fibers of the fabric may comprise a modified polyamine which comprises a hybrid inorganic/organic material comprising a polyamine and an inorganic oxide. The polyamine may comprise one or more of the following: amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, poly (lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, poly(lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups., poly(lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly (vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, polyethylenimine, polyethylenimine derivatives, poly(vinylamine), polymers containing diallylamine, and polymers containing allylamine or a nanostructured polyamine which comprises a polyamine reacted with one or more crosslinkers. MSM (methyl sulfonyl methane) adsorbents may also be included as coatings, admixtures of the above or alone. In one embodiment, MSM is both a metabolite of DMSO and used as an adsorbent. In this embodiment, the MSM used as the adsorbent is substantially odorless and can adsorb odorous DMS (which can be obtained from DMSO through reduction, potentially in an anaerobic metabolic environment), and other odorous compounds that result from DMSO metabolism. In embodiments where the two main metabolites of DMSO are DMS and MSM, exogenous MSM can be used as an adsorbent alone or in combination with other adsorbents. MSM may also be used to adsorb sulfur contain compounds that are related or unrelated to DMSO.

In one embodiment, the odor adsorbing coatings of the fibers, the cross linking members or the intermediate layers of a multilayer fabric may comprise one or more of the following: activated carbon, an inorganic oxide, a compound having ion exchange capacity, a modified compound thereof, an ion exchange resin, a chemical deodorizer, silica gel, alumina gel, zeolite, a molecular sieve, diatomaceous earth, copper oxide, iron oxide, chitosan, dextran sulfate, polyallylamine, sulfonated polystyrene resins, polyacrylic acid, polymethacrylic acid or a derivative thereof. Further, these odor adsorbing coatings may comprise a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin and a copolymer thereof, and a derivative thereof or polytetrafluoroethylene, polyhexafluoropropylene, polydifluoroethylene, polyvinyliden fluoride, polyvinyl fluoride, and a copolymer thereof. They may also consist partially or fully of the oxide, hydroxide, carbonate, sulfates, phosphate, metasilicate, borate, oxalate, tungstate, molybdate, vanadate, chromate, selenate, and manganate of a metal or the metal itself selected from the group consisting of: titanium, zirconium, silicon, zinc, iron, manganese, aluminum, magnesium, nickel, copper, silver, barium, calcium, scandium, bismuth, molybdenum, niobium, neodymium, antimony, selenium, stannum, strontium, terbium, tellurium, thorium, yttrium, and combinations thereof. MSM adsorbents may also be included as coatings, admixtures of the above or alone.

In one embodiment, the invention comprises a modified polyamine comprising: a hybrid inorganic/organic material comprising a polyamine and an inorganic material having one or more characteristics selected from the group consisting of: amorphous structures, high surface areas, large pore volumes, and nanocrystalline structures. In one embodiment, the inorganic material is an inorganic oxide material.

In one embodiment, the invention comprises a modified polyamine comprising a polyamine impregnated into or attached to a porous inorganic or organic microbead. In one embodiment, the polyamine is coupled to one or more microbeads.

In one embodiment, the invention comprises a modified polyamine which comprises a polyamine having inorganic molecules or organic molecules, or both, chemically attached to it.

In one embodiment, the invention comprises a modified polyamine which comprises a bio-compatible copolymer of a polyamine and a dermatologically compatible aqueous-soluble and/or oil-soluble polymer.

In one embodiment, the invention comprises a nanostructured polyamine which comprises a polyamine reacted with one or more crosslinkers.

In one embodiment, the polyamine is selected from the group consisting of one or more of the following: amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups.

In another embodiment, the polyamine is selected from the group consisting of one or more of the following: poly(lysine), polyethylenimine, polyethylenimine derivatives, poly (vinylamine), polymers containing diallylamine, and polymers containing allylamine.

In one embodiment, the invention comprises an article comprising: a liquid pervious topsheet; a backsheet; and an absorbent core intermediate between said backsheet and said topsheet. In one embodiment, the absorbent core comprises from about 0.5 $g/m^2$ to about 500 $g/m^2$ of a cationic polysaccharide comprising an aminopolysaccharide selected from the group consisting of one or more of the following: chitosan, chitosan salt, crosslinked chitosan and a mixture thereof; and from about 0.1 $g/m^2$ to about 250 $g/m^2$ of an acidic pH buffering means having a pH in the range of from about 3.5 to about 6.5 and comprises a weak acid having its pKa or at least one of its pKas in the range from about 3.5 to about 6.5 and its conjugate base; and from about 5 $g/m^2$ to about 250 $g/m^2$ of absorbent gelling material.

In one embodiment, the cationic polysaccharide is selected from the group consisting of one or more of the following: chitosan, chitosan salt, crosslinked chitosan and a mixture thereof having a degree of deacetylation of more than about 75%.

In one embodiment, the chitosan salt is selected from the group consisting of one or more of the following: citric acid, formic acid, acetic acid, N-acetylglycine, acetylsalicylic acid, tlimaric acid, glycolic acid, iminodiacetic acid, itaconic acid, lactic acid, maleic acid, inalic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, tryptophan, methionine, glycine, serine, cysteine, tyrosine, asparagine, glutamine, lysine, arginine, hydroxyproline, pyrrolidone carboxylic acid, chitosonium pyrrolidone carboxylate and mixtures thereof.

In one embodiment, the pH buffering means is selected from the group consisting of one or more of the following: citric acid/sodium hydroxide, citric acid/sodium citrate, citric acid/potassium citrate, oxalic acid/sodium oxalate, tartaric acid/potassium hydrogen tartarate, oxalic acid/potassium tetra oxalate dihydrate, phthalic acid/potassium phthalate, phthalic acid/sodium phthalate acetic acid/sodium acetate, benzoic acid/sodium benzoate, glutaric acid/sodium glutarate, adipic acid/sodium adipate, carbonic acid/sodium carbonate and mixture thereof and in other embodiments is citric acid/sodium citrate, citric acid/sodium hydroxide and/or citric acid/potassium citrate.

In one embodiment, the invention comprises an additional odor control agent selected from the group consisting of one or more of the following: zeolites, silicates, activated carbons, diatomaceous earth, cyclodextrine, clay, chelating agents, ion exchange resins, perfumes and mixture thereof. In one embodiment, the level of the additional odor control agent or a mixture thereof is from about 0.5 g/m² to about 600 g/m².

In one embodiment, the invention comprises a method of controlling odor associated with DMSO and related odorous metabolites wherein said bodily fluids are contacted with an odor control system comprising a cationic polysaccharide, selected from the group consisting of one or more of the following: chitosan, chitosan salt, crosslinked chitosan and a mixture thereof, and an acid pH buffering means typically having a pH in the range of about 3.5 to 6.5.

In one embodiment, the invention comprises an odor eliminating fiber structure having an indicator comprising a fiber substrate containing odor eliminating fibers, a surface thereof being visibly determined for change of odor eliminating power with a difference between a color of the fiber substrate discoloring through adsorption of a smelling gas and a color of a standard color display part.

In one embodiment, the color of the standard color display part provided on the surface of the fiber substrate becomes difficult to be distinguished by discoloration of the fiber substrate through adsorption of a smelling gas.

In one embodiment, the color difference between the color of the fiber substrate upon losing the odor eliminating power and the color of the standard color display part provided on the surface of the fiber substrate is 4 or more grades upon evaluation with gray scale for assessing change in color.

In one embodiment, the odor eliminating fibers contain at least one odor eliminating component selected from silver, copper and a metallic compound thereof, and a content of silver and/or copper is 0.1% by weight or more of the total fiber substrate.

In one embodiment, the odor eliminating fibers comprises an odor eliminating component-containing crosslinked acrylate fibers containing at least one odor eliminating component selected from silver, copper and a metallic compound thereof, and content of a silver and/or copper is 0.1% by weight or more of the total acrylate fibers.

In one embodiment, one surface of the fiber substrate has an easy-sticking and easy-releasing function.

The odor-absorbing fabric may be used in the manufacture of a disposable absorbent article selected from the group consisting of one or more of the following: a patient bedcover, patient gown, caregiver scrubs, gowns, masks, or any other required item to be worn or used to protect the patient or staff or visitors. The odor-absorbing fabric according to any of the embodiments herein may absorb or adsorb odors.

The patient bedding may comprise one or more of the following: suitably large sheets of odor absorbing material which may be coated partially or fully with slightly adhering material to prevent slippage. They may be assembled using methods well known in the art of clothing manufacture, including thermal, ultrasonic or electronic sealing, hot melt, adhesives, sewing, multineedle sewing, serging, basting, binding, or other joining methods. Seams may be folded, lapped, flat felled, straight stitched, frenched, overcast, enclosed, bound, hemmed, reinforced, top stitched, or other suitable seaming method. This bedding can be used at all times while the patient is undergoing treatment using DMSO and related compounds.

The clothing and mask items for the patient and for the caregivers may be shaped and formed to provide the maximum freedom of movement and access. These items may be constructed of cut sheets of odor absorbing material and may include ties, belts, snaps, or other fasteners to maintain the position of the article. These items may be assembled using thermal, ultrasonic or electronic sealing, hot melt, adhesives, sewing, multineedle sewing, serging, basting, binding, or other joining methods. Seams may be folded, lapped, flat felled, straight stitched, frenched, overcast, enclosed, bound, hemmed, reinforced, top stitched, or other suitable seaming method. These items can be used at all times while the patient is undergoing treatment using DMSO and related compounds. The clothing and mask items described herein may comprise any or all of the DMSO and related odorous metabolite capturing capabilities and features of embodiments described herein.

In one embodiment, the invention comprises a method of providing disposable, strong, absorbent DMSO and related odorous metabolite capturing health care bedding which comprises providing DMSO and related odorous metabolite capturing fabric plus a non-woven fabric comprised of randomly entangled mixtures of natural and synthetic fibers interconnected so that the individual fibers are held in place to form a coherent, stable, strong fabric having a high absorbency capacity; cutting the fabric to the desired length in the cross direction; and converting said fabric to a desired size and shape. Such material may also comprise any or all of the DMSO and related odorous metabolite capturing capabilities and features of embodiments described herein.

In one embodiment, the natural fiber is cellulosic wood pulp. In one embodiment, the synthetic fiber is selected from the group consisting of one or more of the following: a polyester, a nylon, a rayon, a polypropylene and mixtures thereof. In one embodiment, the synthetic fiber is polyester.

In one embodiment, the invention comprises a method of providing disposable strong, absorbent DMSO and related odorous metabolite capturing health care bedding which comprises employing as the bedding material DMSO and related odorous metabolite capturing fabric principally composed of polyester fibers combined with cellulosic wood pulp fibers, said fibers locked into place by a three-dimensional fiber entanglement wherein the individual fibers are intertwined, tangled and interconnected to each other so as to be virtually inseparable, said fabric having an absorptive capacity of at least that of woven fabric made of natural fibers, cutting the fabric to a desired length in the cross direction, and converting said cut fabric to a desired size and shape. Such material may also comprise any or all of the DMSO and related odorous metabolite capturing capabilities and features of embodiments described herein.

In one embodiment, the fabric has a weight of about 0.5 to about 10 ounces per square yard.

In one embodiment, after cutting said bedding material in the cross (CD) direction, a strip of elastic is attached along the edges to provide a close fit to a platform it is to cover. The platform may be a six-sided gurney.

In one embodiment, the invention comprises a method of providing disposable, strong, moisture absorbent DMSO and related odorous metabolite capturing health care bed and gurney coverings comprising: employing as the bedding material DMSO and related odorous metabolite capturing fabric principally composed of polyester fibers combined with cellulosic wood pulp fibers, said fibers interlocked by a three-dimensional fiber entanglement, wherein the individual fibers are intertwined, tangled and interconnected to each other so as to be virtually inseparable, and wherein said fabric has an absorptive capacity higher than that of conventional bedding made from cotton-polyester blends. In another embodiment, the method further comprises cutting across the fabric and converting said bedding material to a desired shape suitable for a gurney covering, so that its strongest direction is along the cut direction of the covering. Such material may also comprise any or all of the DMSO and related odorous metabolite capturing capabilities and features of embodiments described herein.

A breathable DMSO and related odorous metabolite capturing composite having hydrostatic head according to IST 80.4-92 of at least about 4 inches comprising a laminate of at least one fibrous, nonwoven web layer and at least one thermoplastic film layer, the laminate being stretched no more than about 5% in a lengthwise and widthwise direction, and wherein the film layer comprises at least one thermoplastic resin, a finely divided particulate material capable of promoting breathability, and a plurality of point-like deformations which provide breathability of the composite, wherein the breathable composite has a breathability of at least about 500 $g/m^2/day$. Such material may also comprise any or all of the DMSO and related odorous metabolite capturing capabilities and features of embodiments described herein.

In one embodiment, the composite has a MVTR of at least about 500 $g/m^2/day$, wherein the laminate can be stretched to less than about 5% lengthwise or widthwise stretching.

In one embodiment, the fibrous nonwoven web layer comprises filaments comprising at least one polyolefin resin.

In one embodiment, the thermoplastic film layer comprises at least one polyolefin resin.

In one embodiment, the thermoplastic film layer comprises at least one polyolefin resin and the nonwoven web layer comprises filaments comprising at least one polyolefin resin.

In one embodiment, the nonwoven web layer has substantial segments of filaments unadhered to the film layer whereby a cloth texture suitable for diaper and apparel uses is provided on at least one surface of the composite.

In one embodiment, the composite has a hydrostatic head of at least about 7 inches.

In one embodiment, the polyolefin resin of the thermoplastic film layer comprises at least one polyethylene resin. In one embodiment, the polyolefin resin of the thermoplastic, breathable film layer comprises at least one polypropylene resin.

In one embodiment, the polyolefin resin of the filaments comprises at least one polyethylene or polypropylene resin. In one embodiment, the polyolefin resin of the filaments comprises at least one polyethylene resin.

In one embodiment, the invention comprises a breathable composite DMSO and related odorous metabolite capturing material comprising a laminate comprising at least one film layer and at least one nonwoven web layer, the laminate being no more than insignificantly stretched in a lengthwise and widthwise direction, and wherein the nonwoven web layer comprises filaments of at least one polyolefin resin, and the film layer comprises a polyolefin resin, a finely divided particulate material capable of promoting breathability, and a plurality of embossed, point-like deformations, such deformations providing breathability of the composite by occupying about 8 to about 40% of the area of a surface of the composite and being present on such surface at a density of about 100 to 500 points per square inch. Such material may also comprise any or all of the DMSO and related odorous metabolite capturing capabilities and features of embodiments described herein.

In one embodiment, the polyolefin resin of the film layer comprises at least one polyethylene resin.

In one embodiment, the nonwoven web layer comprises a web of substantially continuous filaments.

In one embodiment, the filaments comprise at least one polypropylene resin. In one embodiment, the filaments of the web of substantially continuous filaments provide a cloth texture to said nonwoven web layer on at least one surface of the composite. In one embodiment, the filaments comprise at least one polyethylene resin. In one embodiment, the filaments of the web of substantially continuous filaments provide a cloth texture to said nonwoven web layer on at least one surface of the composite.

In one embodiment, the nonwoven web layer comprises a web of staple fibers.

In one embodiment, the staple fibers comprise at least one polypropylene resin. In one embodiment, the staple fibers of the web of staple fibers provide a cloth texture to said nonwoven web layer on at least one surface of the composite. In one embodiment, the staple fibers comprise at least one polyethylene resin. In one embodiment, the staple fibers of the web of staple fibers provide a cloth texture to said nonwoven web layer on at least one surface of the composite.

In one embodiment, the polyolefin resin of the film layer comprises at least one polypropylene resin.

In one embodiment, the nonwoven web layer comprises a web of substantially continuous filaments comprising at least one polypropylene resin. In one embodiment, the nonwoven web layer comprises staple fibers comprising at least one polypropylene resin. In one embodiment, the nonwoven web layer comprises a web of substantially continuous filaments comprising at least one polyethylene resin. In one embodiment, the nonwoven web layer comprises staple fibers comprising at least one polyethylene resin.

In another embodiment, the adsorbent materials/fibers described herein are incorporated into one or more portions of a disposable gown for DMSO treated medical patients, such as the gown described in U.S. Pat. No. 4,819,275, the entire contents of which are incorporated herein by reference. This patent describes a disposable, double-breasted gown for medical patients formed, without sewing, of non-woven synthetic plastic fabric sheeting which is soft and ultrasonically sealable, said gown comprising: a body formed from a rectangular blank having a straight upper long edge that is die cut to form chamfered corners on either side, an off-center arcuate neck indentation and isosceles triangular arm hole indentations on the left and right sides of the arcuate indentation, the resultant straight edge shoulder segments formed between the corners and the indentations all having the same length and a common line, the peaks of the triangular indentations being aligned with parallel left and right transverse fold lines that define between the lines a rear gown section on one side of which is a relatively narrow left-front section and on the other side of which is a broad right-front section, the left-front section being folded over the rear section and the right-front section being folded over the folded left-front section to overlap this section, the straight edge segments of the left and right front sections being ultrasonically seamed to the corresponding segments of the rear section to define left and right arm holes; and a pair of sleeves whose inlets are ultrasonically seamed to the arm holes of the body, each sleeve being formed of a relatively small rectangular blank having at its upper edge an isosceles triangular indentation whose peak is aligned with a center transverse fold line, and having a straight lower edge, such that when this blank is folded in half, and the folded over lower straight edge is ultrasonically seamed, this creates a tubular sleeve having an inlet which is ultrasonically seamed to the arm holes of the body of the gown.

In one embodiment, the adsorbent materials/fibers described herein are incorporated into one or more portions of a surgical gown or scrubs for caregivers of DMSO treated patients, such as the type described in U.S. Pat. No. 4,171, 542, the entire contents of which are incorporated herein by reference.

The gown described in U.S. Pat. No. 4,171,542 has sleeves, a front portion having a chest area covering the chest of the user and side portions which close and overlap at the back of the user, a bib affixed about its periphery to the inside surface of the surgical gown at the chest area with a portion of the bib inwardly of the periphery remaining unsecured to the gown, the chest area having a pair of spaced, substantially vertical slits formed therein within the confines of the peripheral portions of the bib, the slits communicating with the unsecured portion of the bib and being of a length to allow passage of the user's hands therethrough whereby the bib provides a sterile hand support pocket maintaining the user's hands in the aseptic zone bounded by the user's neck, shoulders and waist line.

In another embodiment, the adsorbent materials/fibers described herein are incorporated into one or more portions of a disposable face mask for caregivers of DMSO treated patients. Exemplary masks include those described in U.S. Pat. Nos. 6,055,982; 5,765,556 and 5,322,061, herein incorporated by reference. In general, the masks described in these patents comprise a filter body having an opening sized to cover the nose and mouth of a wearer, the body having top and bottom edges with the top edge arranged to extend across the nose of the wearer and the bottom edge arranged to extend under the chin of the wearer; the top edge having ends opposite from each other and the bottom edge having ends opposite from each other; first securing means attached to the filter body adjacent to each end of the top edge and arranged to extend generally about the back of the head of the wearer in an approximate linear continuation from the top edge, the first securing means for urging the top edge into tight engagement with the wearer to prevent fluid flow between the top edge and the wearer; second securing means attached to the filter body adjacent to each end of the bottom edge and arranged to extend generally over the top of the head of the wearer in an approximate linear continuation from the bottom edge, the second securing means for urging the bottom edge into tight engagement with the wearer to prevent fluid flow between the bottom edge and the wearer; the filter body comprising an upper portion of generally trapezoidal configuration having a longer side forming the top edge and a lower portion of generally trapezoidal configuration having a longer side forming the bottom edge; the upper and lower portions being joined along all remaining sides; a plurality of radii formed on opposite sides of the filter body extending from the opening; a first strip of sealing material disposed within the filter body adjacent to the opening and extending along the top edge; a second strip of sealing material disposed within the filter body adjacent to the opening and extending along the bottom edge; and the first sealing strip and the second sealing strip cooperating with each other to form a fluid barrier between the opening of the filter body and the face of the wearer.

In one embodiment, color changes indicate adsorption. Color changes upon adsorbing odors may be tested as follows based on several methods, including but not limited to that described in US Patent Publication No. 2003/0190266, herein incorporated by reference. See FIG. 14.

Indicators

In one embodiment, the present invention also provides a visual color indicator, particularly a metal permanganate visual color indicator material suitable for the detection of DMS and other metabolites of DMSO. In one embodiment, sulfides such as DMS are oxidized by potassium permanganate to produce sulfone with the resulting reduction of the permanganate ion eliminating its characteristically intense purple color. The indicator may be included in any one of the layers of the adsorbent described herein, or in an additional layer on a base layer having one, two, or three parts. In one embodiment, an indicator for DMS and the metabolites of DMSO and other related compounds includes core particles containing an adsorbing material as described herein in which the intermediate layer comprises one or more indicators and a metal or other compound, and is disposed between the core particles and the porous coating layer. The structure and components of the core particles are described in detail above. Visual indicators other than color may also be used. One or more indicators may be included within a layer, on the inner surface of a layer, on an outer surface of a layer, or integral with one of the layers.

In another embodiment, the present invention comprises a system which includes a transparent container with a packed bed containing the detecting indicator of the present invention. In one embodiment, the packed bed functions as a holder for the indicator material and may be separate from, or included in, an indicating adsorbent bed utilized for the removal of DMS and other DMSO metabolites. In one embodiment, as the indicator is exposed to DMS, methyl mercaptan and related materials, it becomes progressively lighter and the lightening progresses through the bed.

In a further embodiment, the present invention includes a personal monitor comprising one or more detecting indicators to sample airborne contaminants by the process of diffusion. Exposure levels may then be compared to permissible exposure limits published in health and safety standards. In one embodiment, the lighter the personal monitoring patch, the greater exposure is indicated.

In yet another embodiment, the present invention includes a standard format ambient air sampling tube for a standard air sampling pump such tube containing the detecting indicator. In one embodiment, the longer the lightened area, the more DMS, methyl mercaptan or other sulfide detected.

In one embodiment, the invention comprises a functional ambiance odor or sulfur chemical or DMS indicating and/or regulating member comprising the ambiance odor or sulfur chemical regulating member.

In one embodiment, the invention comprises an ambiance odor or sulfur chemical or DMS indicating and/or regulating member, comprising core particles containing at least one odor or sulfur chemical regulating material of an acid salt, and a porous coating layer including a polymer material that coats said core particles, wherein the acid salt is at least one of an alkali metal salt, an alkaline earth metal salt, and an ammonium salt.

In one embodiment, the odor or sulfur chemical regulating material is selected from the group consisting of one or more of the following: sodium sulfate, an alkali metal salt of phosphoric acid, an alkali metal salt of hydrogen phosphate, an ammonium salt of phosphoric acid, and an ammonium salt of hydrogen phosphate.

In one embodiment, the core particles further contains a hydrophilic polymer compound. In one embodiment, the hydrophilic polymer compound is selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the invention comprises any or all of the above indicting absorbents incorporated into a personal monitor sampling, detecting, and indicating airborne DMS and other odorous compounds resulting from the metabolism of DMSO and associated compounds by the process of diffusion.

In one embodiment, the invention comprises any or all of the above indicting absorbents incorporated into a standard format ambient air sampling tube for a standard air sampling pump such tube containing the detecting indicator for indicating airborne DMS and other odorous compounds resulting from the metabolism of DMSO and associated compounds.

Compositions Comprising DMSO

In one embodiment, DMSO is used alone to treat a patient. In other embodiments, DMSO is used in combination with other compounds. The use of the activated carbon filters described herein will facilitate the treatment of patients with DMSO and/or DMSO related compounds.

In one embodiment, the composition is provided as a pharmaceutical formulation which is used to treat a patient with brain injury or stroke. In one embodiment, the pharmaceutical formulation is provided intravenously at a rate of about 1 ml/min to about 30 ml/min, or about 10 ml/min administered. Administration at a rate less than 1 ml/min or greater than 30 ml/min can also be used. Other pathologies may also benefit from this combination, including traumatic brain injury, ischemic stroke, atherosclerosis, neurodegeneration, and spinal cord trauma.

In one embodiment, the invention provides a combination of DMSO (about 1 gram in a 28% solution) and L-arginine (about 1.0 to 8.0 g dissolved in the DMSO solution). In other embodiments, about 10 grams to about 200 grams, e.g., about 40 grams to 100 grams or about 70 grams of DMSO is administered to an individual in a dose. In several embodiments, a concentration of about 5% to about 50%, e.g., about 15% to about 40% or about 30% DMSO in solution (such as dextrose, water or physiological saline) is provided in a dose. Doses may be administered daily, weekly, monthly, or as needed. Other time intervals for dosing may also be appropriate. In one embodiment, the invention provides a pharmaceutical formulation comprising DMSO, L-arginine, and L-lysine. In one embodiment, the invention comprises a pharmaceutical formulation comprising DMSO and L-lysine. In another embodiment, one or more additional amino acids are included.

In one embodiment, the combination of DMSO, L-arginine (about 1.0 to 8.0 g dissolved in the DMSO solution), and L-lysine (about 200 to 900 mg dissolved in the DMSO solution) is provided. In one embodiment, the combination is provided intravenously a rate of about 10 ml/min and is administered for traumatic brain injury or for stroke. In some embodiments, DMSO (alone or in combination) is provided in a concentration of about 20%-40%.

In one embodiment, the invention comprises a pharmaceutical composition comprising DMSO and L-aspartate. In one embodiment, the invention comprises a pharmaceutical composition comprising DMSO, L-arginine, and L-aspartate. In some embodiments, DMSO is provided in a concentration of about 20%-40%.

In one embodiment, a combination of DMSO, L-arginine (about 1.0 to 8.0 g dissolved in the DMSO solution), and L-aspartate (about 100 to 1,200 mg dissolved in the DMSO solution) is given intravenously at a rate of 10 ml/min and administered for traumatic brain injury or for stroke. In some embodiments, DMSO is provided in a concentration of about 20%-40%.

The safety of intravenous DMSO is well-established. L-arginine has been shown in numerous studies to be safe at doses up to 30 grams/day, or intravenously at doses up to 15 g/day. The typical dietary intake of L-arginine is 3.5 to 5 grams daily. This semi-essential amino acid has not been used extensively for intravenous administration and its use is mainly through the oral route. L-aspartate and L-lysine have been given in doses of 250 mg/Kg without adverse effects. All of these compounds are commercially available.

Supplemental L-arginine may have anti-atherogenic, antioxidant and immunomodulatory actions. It may also have wound-repair activity. Thus, in one embodiment, L-arginine is administered in combination with DMSO (or DMSO metabolites or derivatives) to treat pathologies in which antiatherogenic, antioxidant, immunomodulatory actions, and/or wound-repair activity would be desirable. Such pathologies include atherosclerosis, cancer, systemic lupus erythematosus, arthritis, inflammation, and autoimmune disease.

In one embodiment, the invention comprises a combination of DMSO, L-arginine, and one or more of the following: fructose 1,6-diphosphate, L-lysine, L-aspartate, and urea. In another embodiment, DMSO and urea is used together or in combination with L-arginine, fructose 1,6-diphosphate, L-lysine, L-aspartate. A DMSO associated compound may be used in addition to, or instead of DMSO, in any of the embodiments described herein.

The compositions and combinations described herein may be used to prevent or treat one or more of the following pathologies: traumatic brain injury, ischemic stroke, atherosclerosis, spinal cord trauma, and other dementias, and as a neuronal protector to prevent brain damage, for example, during coronary artery bypass graft (CABG). These compositions may also be used to treat neurodegenerative disorders including, but not limited to, Alzheimer's disease, Parkinson's disease, subacute sclerosing panencephalitis, vascular dementia, multiple sclerosis, assorted neuropathies, Huntington's disease, amyotrophic lateral sclerosis (ALS) and leukodystrophies.

The amounts of L-arginine, fructose 1,6 diphosphate and L-asparate to be combined with the DMSO will vary depending of the disorder to be treated, severity of the disorder and age of the patient, but in general the amounts of these compounds will range from about 0.5% w/v to about 10% w/v.

Several embodiments of the present invention is also directed to the use of any of the DMSO-containing compositions described hereinabove for treatment of any of the disorders disclosed herein. In addition, other embodiments are directed to the use of any of the DMSO-containing compositions described above in the preparation of a medicament for treatment of any of the disorders described herein.

The pharmaceutical compositions described herein can be administered to a human or non-human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in several embodiments of the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions according to several embodiments of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. A suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 6000 mg of each ingredient, or between 1 mg and 5000 mg, e.g. 25 to 5000 mg or an intravenous, subcutaneous, or intramuscular dose of each ingredient between 0.01 mg and 100 mg, e.g., between 0.1 mg and 60 mg or 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, at a dose of each ingredient up to 400 mg per day. Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for several days, a week or more, or for months or years. DMSO alone or in combination with the compounds described herein may be administered as a one-time therapy immediately upon affliction of injury. A low dose of DMSO alone or in combination with the compounds described may be administered on a regular basis to individuals susceptible to stroke, and thereby serve as a preventative measure or as a measure that would lower the risk of having a stroke or other illnesses that are related to cerebral blood flow.

EXAMPLES

The following examples describe non-limiting uses of the compositions, methods and apparatus described herein.

In one embodiment, a device to remove the odors and compounds resulting from the metabolism of DMSO and associated compounds directly from the patient's exhaled respiratory air is provided. In a preferred embodiment, the device (e.g., the adsorbent) is directly connected to the patient's mask. In one embodiment, this may require treating the highest concentration of odor bearing material.

In one embodiment, an apparatus to remove the odors and compounds resulting from the metabolism of DMSO and associated compounds from the exhaust outlet of a medical respiratory ventilator is provided. In another embodiment, the device is connected to the ventilator's exhaust outlet through a gas scavenging device. In one embodiment, the apparatus comprises a gas scavenging device comprising the adsorbent described herein, wherein the gas scavenging device is connected to the exhaust outlet. Thus, the DMSO metabolite-containing exhaust leaving the ventilator passes through the adsorbent which filters out the metabolites and odors, resulting in air that does not contain the odors associated with the metabolites.

In one embodiment, a device to remove the odors and compounds resulting from the metabolism of DMSO and associated compounds from the recirculated or vented stream a room sized HVAC or clean room system is provided. In one embodiment, the device (e.g., the adsorbent) is connected to the system's ductwork.

In one embodiment, an adsorbent to be adhered to or sandwiched between three dimensional fiber material as in fabric, cloth, felt, nonwoven or other flexible material to become part of clothing, bedding, masks and other items used by the patient or the medical staff is provided.

An article of patient bed covering to capture the odors and compounds emanating from the dermal areas of the patient and resulting from the metabolism of DMSO (dimethyl sulfoxide) and associated compounds is provided.

An article of patient clothing to capture the odors and compounds emanating from the dermal areas of the patient's body and resulting from the metabolism of DMSO (dimethyl sulfoxide) and associated compounds is also provided.

An article of caregiver clothing to capture the odors and compounds emanating from all areas of the patient including respiration and resulting from the metabolism of DMSO (dimethyl sulfoxide) and associated compounds is provided.

A caregiver mask to reduce and/or prevent the breathing by the caregiver of the odors and compounds emanating all areas of the patient including respiration and resulting from the metabolism of DMSO (dimethyl sulfoxide) and associated compounds is provided.

A device to remove the odors, DMS, methyl mercaptan and/or hydrogen sulfide and compounds resulting from the metabolism of DMSO and associated compounds directly from the area around a patient (e.g., the patient's upper torso) is provided. The flexible patient isolation assembly may or may not be connected to the clean air delivery assembly's top final filter hood assembly.

A device to remove the odors and compounds resulting from the metabolism of DMSO and associated compounds from the entire patient bed area with or without enough space for caregiver occupancy of the patient isolation assembly is provided. The clean air delivery assembly device may be connected to the patient isolation assembly sized to enclose only the bed or to provide caregiver access.

A device to remove the odors and compounds resulting from the metabolism of DMSO and associated compounds from the entire patient room is provided. The clean air delivery assembly may positioned with the top final filter hood assembly over the patient or preferably within the room should the patient be served by another unit.

A device to remove the odors and compounds resulting from the metabolism of DMSO and associated compounds directly from the area around the patient's wheelchair or gurney is provided. The portable clean air delivery assembly device may be connected to the wheelchair or gurney by means of clamps, straps or other suitable means. The flexible patient isolation assembly may or may not be connected to the clean air delivery assembly's top final filter hood assembly.

A device to indicate the presence of DMS and other odorous compounds resulting from the metabolism of DMSO and associated compounds directly from the patient's exhaled respiratory air is provided. Such compounds may be detected in concentrations of about 1 to about 10,000 parts per million. The device may be directly connected to the patient's mask.

A device to indicate the presence of DMS and other odorous compounds resulting from the metabolism of DMSO and associated compounds from the exhaust of a medical respiratory ventilator is provided. Such compounds may be detected in concentrations of about 1 to about 1,000 parts per million. The device may be integral to or connected to an adsorber located on the ventilator's discharge or directly on the ventilator's discharge through a gas scavenging device.

A device to indicate the presence of DMS and other odorous compounds resulting from the metabolism of DMSO and associated compounds from the recirculated or vented stream from a room sized HVAC or clean room system is provided. Such compounds may be detected in concentrations of about 1 to about 10 parts per million. The device may be connected to the system's ductwork.

An indicating adsorbent included in a personal monitor containing the detecting indicator and sampling airborne contaminants by the process of diffusion is provided. Such compounds may be detected in concentrations of about 1 to about 1,000 parts per million. In some embodiments, such personal monitor may be pinned, clipped, or otherwise affixed to the clothing or person of the staff, visitors or patients in the medical facility.

An indicating adsorbent included in a standard format ambient air sampling tube for a standard air sampling pump such tube containing the detecting indicator is provided. Such compounds may be detected in concentrations of about 1 to about 10,000 parts per million. Such sampling may be from the patient's bed area, the room, the respiratory ventilator, the room's HVAC system, or other location.

Examples of Filter Experiments with Ventilators

The examples disclosed below are non-limiting examples of uses of filters, ventilators, systems and compositions disclosed herein. Various embodiments of filters 20 were tested in conjunction with various embodiments of ventilators 40. In some tests, experimentation was undertaken in order to determine the immediate and long-term effects of the addition of an embodiment of an odor-reduction filter 20 to a ventilator 40. In one embodiment the ventilator 40 was a Drager ventilator. In one embodiment the ventilator 40 was a Puritan ventilator. In various embodiments, any ventilator 40 could be used in any setting, such as a hospital, treatment setting, or other location.

The testing done on an embodiment of the odor-reduction filter 20 with a ventilator 40 took place in two sessions. The first session was a series of short-term tests to determine the effect, if any, on the ventilation of a patient with the filter 20 placed in a downstream configuration 50 as compared to an upstream configuration 52 with respect to embodiments of accessories. In various embodiments, the location of the filter 20 with respect to the ventilator 40 can have little effect on the air flow. In some embodiments, the location of the filter 20 with respect to other accessories could have effects on the air flow. In various embodiments, the accessories could be a contaminant filter, a bio-filter, a HEPA filter, a heating element, a cooling element, a heat sink, a humidifier, a water trap, a sensor, a monitor, a flow meter, or any other type of accessory for monitoring or modifying the fluid (such as air) flow in the system.

In one embodiment, the downstream configuration 50 comprises the filter 20 disposed at a portion of a fluidly connected system, line or tube that is downstream of one or more accessories with respect to the odor-source. For example, in one embodiment a downstream configuration 50 can comprise an odor-source fluidly connected via a tube or port to a ventilator 40, where the ventilator 40 fluidly connects the odor-source (such as a patient) through any number of accessories (such as, but not necessarily limited to a HEPA filter, a water trap, or other accessories), wherein the filter 20 is placed downstream of (or farther away along the fluid connection from the odor-source) any of the other accessories. In some embodiments of downstream configurations 50, the filter 20 is located next to or at the exhaust port of the ventilator 40 as the last component through which the odor travels before being released in to the environment, open air or atmosphere. In one embodiment, the odor can be DMSO and/or a related compound or metabolite of DMSO.

In one embodiment, the upstream configuration 52 comprises the filter 20 disposed at a portion of a fluidly connected system, line or tube that is upstream or proximal to one or more accessories with respect to the odor-source. In one embodiment, the upstream configuration 52 comprises the filter 20 at a portion of an exhaust line or hose 35 of a ventilator 40, upstream of components such as a HEPA filter and/or a water trap with respect to the exit or exhaust port of the ventilator 40. In various embodiments, the placement of a filter 20 can be at any location, upstream, downstream, inside or outside any of the components of a ventilator 40, including but not limited to any other filter, water trap, heater, humidifier, media, metabolite, etc. The second session was a long-term test, observing how the system would behave with the filter 20 in place over a full six-hour test interval, complete with humidification, heating, and the presence of DMS.

The first round of testing took place on two different embodiments of ventilators 40, the Drager and Puritan models. On each ventilator 40, trials were run with both a test lung and with a volunteer subject breathing into an airflow system in fluid communication with an embodiment of the filter 20. The measurements were recorded before the filter 20 was put in place in the downstream configuration 50 or the upstream configuration 52, immediately after the filter 20 was put in place in the downstream configuration 50 or the upstream configuration 52, and again after ten minutes with the filter 20 in place in the downstream configuration 50 or the upstream configuration 52.

The second round of testing was a full, six-hour long trial of an embodiment of the filter 20 in an embodiment of the system using a test lung. Humidity and heat were applied to the system using various embodiments of accessories, as they would be in a hospital or medical treatment setting, and a full amount of DMS (the odor-causing metabolite in DMSO treatment) was also inserted into the system over the course of the six-hour trial, in order both to test the effectiveness of the filter 20 and to determine whether its characteristics would change as the filter 20 absorbed the compound/odor.

Example 1

Test Lung-Square Function

Using a test-lung, one embodiment of the experimental breathing system was set up according to the parameters listed in FIG. 15, using a Square function breathing simulation. In some of the experiments the downstream configuration 50 and upstream configuration 52 terms are used to describe the placement of the filter 20. In one embodiment, the downstream configuration 50 placement refers to the filter 20 being placed downstream in a fluidly connected breathing system, more distal from the subject than any HEPA filter, heat sink, water trap, or other accessory in breathing system. In one embodiment, the upstream configuration 52 placement refers to the filter 20 being placed upstream, or more proximal to the subject with respect to accessories. In one embodiment of the testing, the data showed no significant changes in maximum pressure (P(max)), mean pressure (P(mean)), or Positive end-expiratory pressure (PEEP) when the filter 20 was placed in the downstream configuration 50, as the last item in the system. However, in one embodiment, when the filter 20 was placed at an upstream configuration 52, an increase in both the mean pressure and the PEEP was observed. In some embodiments having both the upstream configuration 52 and a downstream configuration 50, there was no significant increase in the air flow resistance noted, indicating that the filter 20 did not gradually become more of a hindrance to the flow as the testing proceeded.

Example 2

Test Lung-Ramp Function

One embodiment of the experimental breathing system test reflected at FIG. 16 was similar to the previous test reflected at FIG. 15, with one difference being the breathing function selected to the Ramp Function, rather than the Square function. Again, no significant difference was noted with the embodiment of the filter 20 in the downstream configuration 50 location. The mean pressure increased very slightly, but the maximum pressure and PEEP either stayed constant or decreased during the testing. The increase in pressure was more notable when an embodiment of the filter 20 was placed at the upstream configuration 52.

Example 3

Human Trial

With respect to an example of one embodiment of the experimental breathing system summarized at FIG. 17, the ventilator 40 was placed by a respiratory therapist at a setting allowing a patient subject to breathe through a mask 30. A test subject used the ventilator 40 to breathe for several minutes before the initial reading was taken, and then an embodiment of the filter 20 was applied. The subject continued breathing with the help of an embodiment of a ventilator 40.

While the human element introduced greater fluctuation in the observed data, even when the filter 20 was not applied, the data showed that there was not a significant increase in the pressure the test volunteer felt, or an increase in the resistance due to moisture build-up over time. The subject reported feeling a slight increase in the difficulty of exhaling in the first two breaths after the filter 20 was applied, but the effect did not continue, and breathing was not reported to be any more difficult with the filter 20 in the downstream configuration 50 than it was without the filter 20.

Example 4

Humidifier

With respect to an example of one embodiment of the experimental breathing system summarized at FIG. 18, in order to ascertain the effect of a great deal of moisture in the line on the filter 20, a large heating canister filled with heated water was used to simulate the system with humidification. A test lung was used, and the system was compared with the filter 20 placed both at the downstream configuration 50 and at the upstream configuration 52 in this scenario. The test was run for 10 minutes to give the moisture time to accumulate.

The heated water added moisture to the system, but an embodiment of the filter 20, when positioned at the downstream configuration 50, was not affected even after the system had been running for ten minutes with a great deal of water vapor in the system. However, both the mean pressure and the PEEP did increase slightly when the filter 20 was placed in the upstream configuration 52 position. According to one embodiment, no residual moisture was noted in either case with the filter 20 after the testing was concluded.

Example 5

Drager Human Test

With respect to an example of one embodiment of the experimental breathing system summarized at FIG. 19, a test using a volunteer subject was performed using the Drager system. The ventilator 40 was set by a respiratory therapist and the data was taken with the filter 20 in both at the downstream configuration 50 and at the upstream configuration 52 position. The test subject noted that breathing was made much more difficult with the filter 20 in the upstream configuration 52, such as being placed between the patient and embodiments of the accessories, such as a HEPA filter and water traps. The experimental data shows no drop in PEEP when the filter 20 is positioned at the downstream configuration 50, where in one embodiment the filter 20 was placed at the distal end of the exhaust system away from the subject.

Example 6

DMS Six-Hour Test

In one experiment with an embodiment of a ventilator 40 and a test lung, a test was performed according to the settings at FIG. 20. In one embodiment, a test was run for six hours, the entire life-span of one embodiment of a given filter 20. A full amount of DMS that will pass through the system in six hours was also added at two-hour intervals to determine the effect of the odor on the system, as well as determining whether any characteristics of the filter 20 would change as it absorbed the compound. A humidifier accessory was included in one embodiment of the experiment to add moisture to the ventilator system. After the experiment was concluded, the system was disassembled and inspected for odor.

The filter 20 was placed in the downstream configuration 50 position, at the end of the exhaust system, after any other in-line filters and water traps.

According to one embodiment, the system was run for six hours, with moisture, heat, and DMS (the odor-causing agent) added to the system, without any variations in pressure or PEEP. A full dose of DMS was put through the system and the odor was contained by the filter 20. No detrimental effects were noted in the six hours the test was run. In fact, pressure actually began to decrease, slowly but noticeably, as the testing progressed. After the testing was completed, the system was disassembled and tested for lingering odor. A faint odor was detectable in the HEPA filter, but only when held inches away from the nose. The odor was slight enough that it dissipated quickly and was soon undetectable. No odor was detected at the exhaust port, and the room was odor-free throughout the testing.

According to one embodiment, the filter 20 does not demonstrate any detrimental effects on the system when positioned at the downstream configuration 50. According to several embodiments, breathing systems including a filter 20 and a ventilator 40 were tested with both a test lung and a human subject. According to certain embodiments where filters 20 are positioned at the downstream configuration 50, breathing systems were subjected to heat, moisture, and DMS, and did not cause a significant change in maximum pressure, mean pressure, or PEEP.

In some embodiments, experiments with a filter 20 positioned at the upstream configuration 52 caused an increase in mean pressure. According to several embodiments, increase in mean pressure was about 5.2%. This increase in pressure was not seen in embodiments of the experimental testing system when the filter 20 was placed at the downstream configuration 50. Thus, in several embodiments, filters placed in a downstream configuration result in no pressure increase or less than 10%, 7%, 5%, 3% or 1% pressure increase.

In one embodiment, when the filter 20 was at the upstream configuration 52, while testing on the Drager unit with a human volunteer, a drop in PEEP was noted. In other embodiments, no adverse effects were seen on the system when the filter 20 was placed in the downstream configuration 50. In one embodiment of an experiment, the drop in PEEP was reversed as soon as the filter 20 was moved from the upstream configuration 52 location (prior to or upstream of an accessory, such as a HEPA filter) to the downstream configuration 50 location. In some embodiments, PEEP remained relatively constant and unaffected, irrespective of the placement of the filter 20.

In one embodiment, the system was tested over six hours, the full life-span of one embodiment of the filter 20, with heat, humidity, and the full dosage of DMS odor added to the system. According to one embodiment, there was no drop-off in the performance of the system as time passed, no accumulation of moisture in the filter, no changes in the maximum pressure, mean pressure, or PEEP. Further, the odor reduction filter was extremely effective in removing the DMS odor from the system. The residual odor in the system was slight and very quickly dissipated after the testing was concluded. Thus, in several embodiments, the invention comprises the use of a filter system that is characterized by no (or less than 1%, 2%, 3%, 4% or 5%): (i) drop-off in the performance of the system, (ii) accumulation of moisture in the filter; (iii) change in maximum pressure; (iv) change in mean pressure; and/or (v) change in PEEP.

In some embodiments, testing was performed with both human volunteers and test lungs showed no difference in the performance of the filter 20 or the ventilator 40. In some embodiments, moisture build-up or increased resistance in the system as time passed were not observed in any of the testing, either with human volunteers or with humidity and water vapor added to the system over six hours.

Example 7

DMS Filter Test

In one embodiment, testing was performed with an activated carbon filter 20 that was fluidly attached to a ventilator 40 or other breathing system. According to one embodiment, doses of DMSO were administered every six hours. The filter 20 removed the odor from the airflow for at least that amount of time before being replaced. A mass spectrometer can be used to determine the concentration of DMS in the system.

Figure 21:
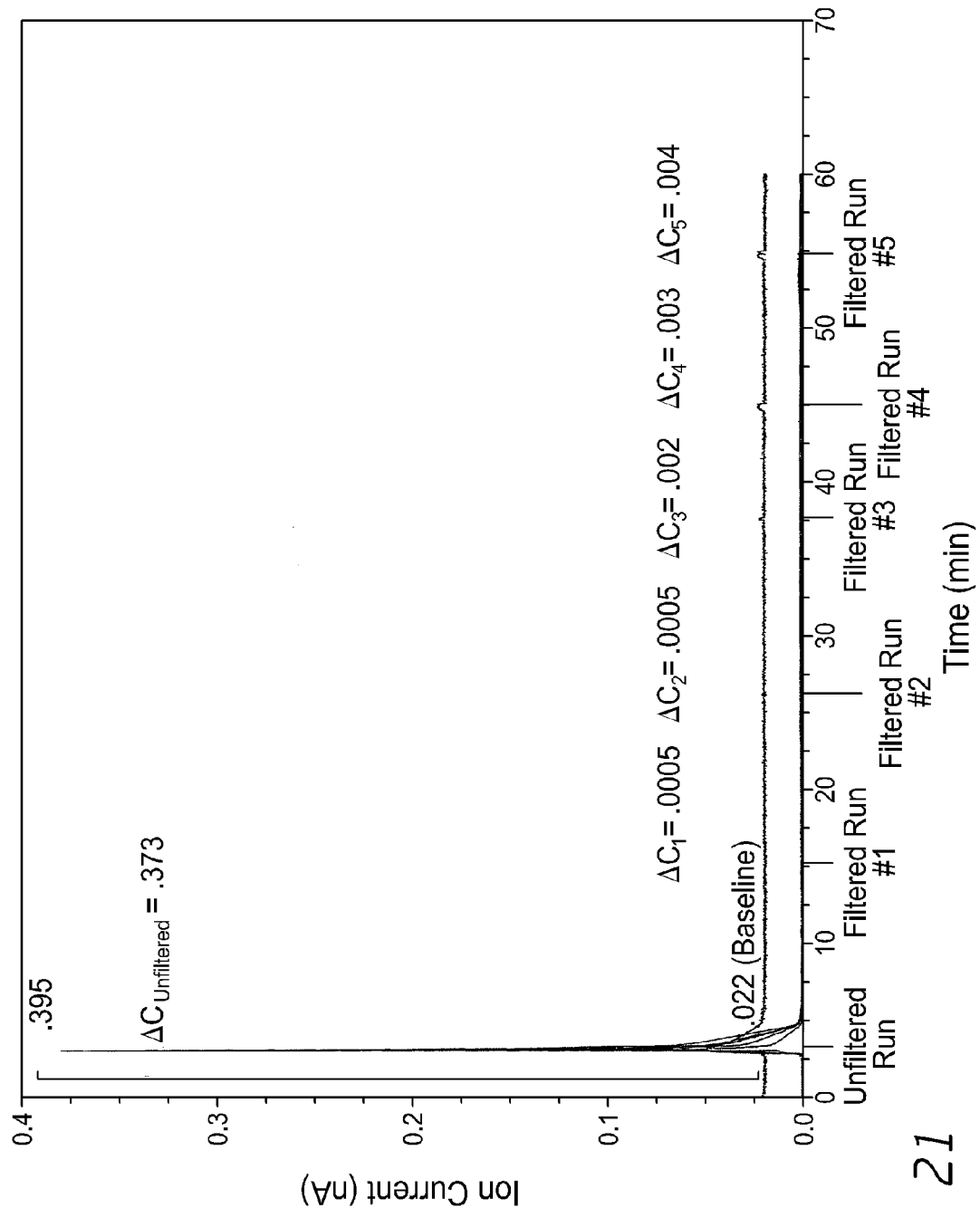
FIG. 21 is a chart reflecting experimental odor measurements according to one embodiment of the present invention.
Figure 22:
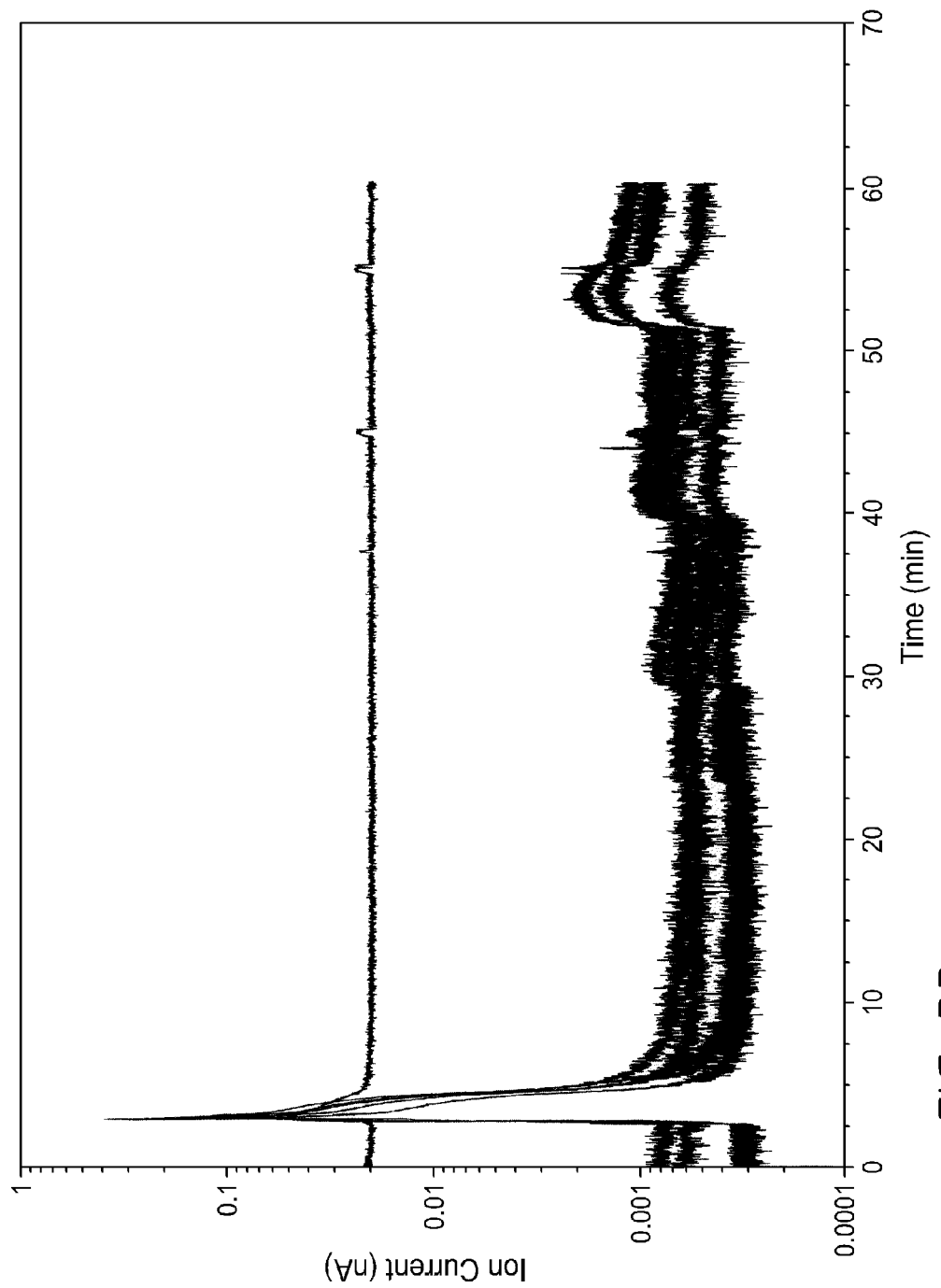
FIG. 22 is a chart reflecting experimental odor measurements according to one embodiment of the present invention.

In one embodiment, an unfiltered test run provided a baseline number for DMS concentration. In one embodiment, results were monitored in the percentage of DMS removed, relative to this baseline. In one embodiment, the baseline is 0.022. See FIGS. 21 and 22. In one embodiment, additional steps were taken to neutralize the combination of the DMS particles that escaped through the patient's pores and any DMS that passed through the filter 20. In one embodiment, a room canister system used a fan to force the DMS-laden air through an activated carbon mesh for odor reduction. In various embodiments, materials that were used in experiments included a mass spectrometer, ventilator tubing, a variable-speed air pump, DMS, a filter with a known amount of activated carbon, a fume hood, 1 mL syringes, and one or more odor masks.

In one embodiment, testing included the following steps or instructions. The air pump was set to blow at 120 liters per minute (1 pm) through the ventilator tubing, with the mass spectrometer connected to the system by a t-junction in the tubing. The tubing could be configured to terminate outside the room or in a well-ventilated room to prevent the odor from building up to noxious levels. 1 mL of DMS was drawn into the syringe within the confines of a fume hood. The DMS was injected into the ventilator tubing before it reached the mass spectrometer, where the level of DMS detected was recorded. After waiting for the amount of DMS to drop to the pre-injection level, a filter 20 was added to the system between the mass spectrometer and the air pump. 1 mL of DMS was injected into the tubing before the filter 20 and the levels on the mass spectrometer were recorded. In one embodiment, the DMS levels can rise slightly and then become relatively constant as the filter removes the majority from the airflow. The relatively constant level can be called the "effective-filtration" level. After most or all of the DMS from the first dose has moved through the system, DMS was added to the system in 0.5 mL dosages until the level of DMS rises above the effective-filtration level. The amount of DMS that has been put through the system was recorded at the saturation point of the system.

In various embodiments, filter calculations were undertaken. For example, in one experiment the following calculations were undertaken for the filter 20. A calculation for conversion to moles DMS for a single dose (6 hours worth) revealed that 56 g DMSO×(1 mol/78 g)×3% (conversion to DMS)=0.0215 mol DMS. A calculation of a ration of moles to grams DMS revealed that 0.0215 mol DMS×(62 g/1 mol)= 1.335 g DMS (per 6 hours). A calculation for conversion from g to mL of DMS (Specific Gravity of 0.85) revealed that 1.335 g×(0.85 g/mL)=1.13 mL DMS (per 6 hours). A calculation for determining a DMS to Carbon Ratio for Filter 1 (Carbon Mesh) revealed that 1 mL DMS×(0.85 g/1 mL)=0.85 g DMS, 35 g carbon:0.85 g DMS, or a ratio of 41.2 g carbon:1 g DMS. A calculation for a DMS to Carbon Ratio for Filter 2 (Granulated) revealed that 1 mL DMS×(0.85 g/1 mL)=4.34 g DMS, 150 g carbon:4.34 g DMS, or a ration of 34.6 g carbon:1 g DMS. A calculation to determine the Granulated Activated Carbon Needed revealed that 1.335 g DMS×(34.6 g carbon/1 g DMS)=46 g activated carbon.

In various embodiments, canister calculations were undertaken. For example, in one experiment the following calculations were undertaken for the room canister. A calculation for determining an amount of DMS expected post-filtration involved calculating Room DMS=(Amount escaping the filter)+(amount escaping through pores)=(0.1% of 95% of total)+(5% of total)=[001×(0.95×1.335 g DMS)]+(0.05×1.335 g DMS)=(0.00126 g DMS)+(0.067 g DMS)=0.068 g DMS. A calculation for determining an amount of Carbon Mesh needed to neutralize expected room DMS involved calculating 0.0794 g DMS×(41.2 g carbon/1 g DMS)=3.27 g carbon mesh (per 6 hours)=6.54 g carbon mesh (per 12 hours).

In one embodiment, the filter 20 contained 150 grams of granulated carbon. A total of 5.1 mL of DMS was passed through this filter 20 in five different trial runs without saturating the activated carbon. Each trial run put an entire six hour dose of DMS through the filter 20 in less than 30 seconds. The filter 20 proved able to handle nearly 5 times the amount of DMS that is needed for each dose of DMSO administered. In a series of trials in one experiment at FIGS. 21 and 22, the results included:

Trial 1: Unfiltered, resulting in a change in concentration of DMS of 0.373.

Trial 2: Filtered #1, resulting in a change in concentration of DMS of 0.0005, and a percentage removed of 99.87%.

Trial 3: Filtered #2, resulting in a change in concentration of DMS of 0.0005, and a percentage removed of 99.87%.

Trial 4: Filtered #3, resulting in a change in concentration of DMS of 0.002, and a percentage removed of 99.47%.

Trial 5: Filtered #4, resulting in a change in concentration of DMS of 0.003, and a percentage removed of 99.20%.

Trial 6: Filtered #5, resulting in a change in concentration of DMS of 0.004, and a percentage removed of 98.93%.

In one test, an entire dose was pushed through the system in less than 30 seconds, and the filter 20 was able to eliminate at least 99.87% of the DMS in the system. In one embodiment, the amount of DMS in a six hour period emitted from a patient in the experiment was roughly 1.335 grams, indicating that 0.00173 grams of DMS could escape the filter into the hospital room every six hours. In one test, the combination of DMS seeping through the filter and escaping from the patient's pores produces 0.08 g of DMS in the room. In a test of the carbon mesh, it was determined based on the DMS ratio found in the filtration experiment that a total of 6.54 g of carbon mesh could neutralize these molecules for a period of 12 hours.

In one embodiment, testing was conducted with two separate filters. The first filter 20 tested was composed of 35 g of an activated carbon mesh. With this first filter 20, more than 99% of the DMS was eliminated when the first filter 20 was operating at peak capacity. The filter was found to be saturated after slightly less than 1 mL of DMS was filtered out, giving an estimate of approximately 41 g of carbon per 1 gram of DMS.

In one embodiment, testing with an off-the-shelf odor mask was qualitatively evaluated during the course of the experimentation. It was concluded that at low concentrations of DMS the off-the-shelf odor mask could prove effective in minimizing the amount of odor detected, but at higher, unfiltered concentrations the masks would be nearly useless.

In one set of experiments, the activated carbon to DMS ratio was found to be 34.6 g:1 g DMS. In one embodiment, the minimum amount of carbon to neutralize a full, 6-hour dose of DMS was 46 g of granulated, activated carbon. With a 100% safety margin to reduce DMS odor, one embodiment of the filter 20 can be constructed with 100 g of activated carbon to capture the DMS.

In one embodiment, the carbon mesh can be replaced every 12 hours. In one embodiment, calculations show that 6.5 g of carbon mesh was able to handle all of the DMS in a room for that period. With a 100% safety margin, two canisters can be placed in the room at the same time, each having at least 6.5 g of activated carbon mesh in place. Based on various experiments with the odor of DMS, it appears that very low concentrations of the compound, while noticeable, are not extremely unpleasant or noxious.

It will be understood by those of skill in the art that numerous and various modifications can be made without departing from the spirit of the present invention. Therefore, it should be clearly understood that the forms of the present invention are illustrative only and are not intended to limit the scope of the invention.

What is claimed is:

1. A system for reducing the concentration of a dimethyl sulfoxide (DMSO) metabolite having an undesired odor, wherein the system comprises:
    a breathing system suitable for placement in fluid communication with a subject comprising:
    a first filter;
    a ventilator;
    and a HEPA filter,
    wherein said first filter, said ventilator, and said HEPA filter are suitable for placement in fluid communication with one another,
    wherein the ventilator is suitable for transporting moist air comprising said DMSO metabolite from a subject to an exhaust port,
    wherein the HEPA filter is positioned between the subject and the filter,
    wherein the first filter is positioned downstream of the HEPA filter,
    wherein said first filter causes no more than a 10% decrease in air flow and no more than a 10% change in pressure in said ventilator,
    wherein the first filter comprises an adsorber and at least one sieve screen,
    wherein the adsorber comprises about 10 grams to about 100 grams of activated carbon,
    wherein said at least one sieve screen is configured to allow said DMSO metabolite to flow through the first filter while containing the adsorber within the filter, and
    wherein contact of the DMSO metabolite with the first filter allows the first filter to capture at least 75% of the DMSO metabolite, thereby reducing the concentration of said DMSO metabolite having an undesired odor.

2. The system of claim 1, wherein the at least one sieve screen comprises polyester.

3. The system of claim 2, wherein the at least one sieve screen comprises a polyester-based lofted material.

4. The system of claim 1, wherein the at least one sieve screen further comprises a tackifier applied to at least a portion of one side of the at least one sieve screen.

5. The system of claim 1, wherein said first filter causes no more than 5 mm Hg change in pressure in said ventilator.

6. The system of claim 1, wherein said breathing system is suitable for placement in fluid communication with the lungs of said subject.

7. The system of claim 6, wherein said breathing system is suitable for fluid communication with the lungs of said subject through a face mask.

8. The system of claim 6, wherein said breathing system is suitable for fluid communication with the lungs of said subject through an endotracheal tube.

9. The system of claim 1, further comprising at least one accessory.

10. The system according to claim 9, wherein the at least one accessory is a biological filter configured to reduce viruses or bacteria.

11. The system according to claim 9, wherein the at least one accessory is a liquid trap to remove liquid from the breathing system.

12. The system according to claim 9, wherein the at least one accessory is a heat sink configured to cool the breathing system.

13. A system for reducing the concentration of a dimethyl sulfoxide (DMSO) metabolite having an undesired odor, wherein the system comprises:
    a gas-line configured for fluid communication with the lungs of a patient;
    wherein the gas-line comprises a filter suitable for fluid connection to a gas exchange device; and
    at least one accessory,
    wherein the filter comprises:
    an adsorber comprising about 10 g to 100 g of activated carbon; and
    at least one sieve screen configured to allow an odor to pass through the filter while preventing the adsorbent from entering or exiting the filter,
    wherein the at least one sieve screen comprises a polyester based lofted material; and
    wherein said filter causes no more than a 10% decrease in flow in said fluid-line.

14. The system according to claim 13, wherein the at least one accessory is a biological filter configured to reduce viruses or bacteria.

15. The system according to claim 13, wherein the at least one accessory is a liquid trap to remove liquid from the gas-line.

16. The system according to claim 13, wherein the at least one accessory is a heat sink configured to cool the gas-line.

* * * * *